(12) United States Patent
Lee et al.

(10) Patent No.: US 7,196,112 B2
(45) Date of Patent: Mar. 27, 2007

(54) CELL ADHESION INHIBITORS

(75) Inventors: Wen-Cherng Lee, Lexington, MA (US); R. Blake Pepinsky, Arlington, MA (US); Mark Cornebise, Watertown, MA (US); Daniel Scott, Weston, MA (US); Russell C. Petter, Stow, MA (US)

(73) Assignee: Biogen Idec MA Inc., Cambridge, MA (US)

( * ) Notice: Subject to any disclaimer, the term of this patent is extended or adjusted under 35 U.S.C. 154(b) by 0 days.

(21) Appl. No.: 10/892,400

(22) Filed: Jul. 16, 2004

(65) Prior Publication Data

US 2006/0014966 A1    Jan. 19, 2006

(51) Int. Cl.
A61K 31/4025 (2006.01)
A61K 31/401 (2006.01)
C07D 207/48 (2006.01)

(52) U.S. Cl. ............ 514/422; 514/423; 548/519; 548/537

(58) Field of Classification Search ......... 514/422, 514/423; 548/519, 537
See application file for complete search history.

(56) References Cited

U.S. PATENT DOCUMENTS

| | | | |
|---|---|---|---|
| 4,725,583 A | 2/1988 | Luly et al. | |
| 4,826,815 A | 5/1989 | Luly et al. | |
| 4,908,360 A | 3/1990 | Martin et al. | |
| 5,260,277 A | 11/1993 | McKenzie | |
| 5,314,902 A | 5/1994 | Tjoeng et al. | |
| 5,399,570 A | 3/1995 | Klingler et al. | |
| 5,403,836 A | 4/1995 | Blackburn et al. | |
| 5,434,188 A | 7/1995 | Boschelli et al. | |
| 5,770,573 A | 6/1998 | Arrhenius et al. | |
| 5,922,755 A * | 7/1999 | Tanaka et al. | 514/456 |
| 6,630,503 B1 * | 10/2003 | Scott et al. | 514/423 |
| 2002/0015999 A1 * | 10/2002 | Mundy et al. | 424/143.1 |
| 2002/0159998 A1 * | 10/2002 | Mundy et al. | 424/143.1 |

FOREIGN PATENT DOCUMENTS

| | | |
|---|---|---|
| EP | 0 021 234 B1 | 1/1981 |
| EP | 0 460 679 B1 | 12/1991 |
| EP | 0 357 192 B1 | 5/1992 |
| EP | 0 519 748 B1 | 12/1992 |
| WO | WO 89/09786 | 10/1989 |
| WO | WO 91/02750 | 3/1991 |
| WO | WO 91/09837 | 7/1991 |
| WO | WO 92/00995 | 1/1992 |
| WO | WO 92/08464 | 5/1992 |
| WO | WO 92/22323 | 12/1992 |
| WO | WO 93/08823 | 5/1993 |
| WO | WO 93/09795 | 5/1993 |
| WO | WO 93/12809 | 7/1993 |
| WO | WO 94/02445 | 2/1994 |
| WO | WO 94/15958 | 7/1994 |
| WO | WO 95/15973 | 6/1995 |
| WO | WO 96/22966 | 8/1996 |
| WO | WO 97/03094 | 1/1997 |
| WO | WO 98/04913 | 2/1998 |
| WO | WO98/53814 | 12/1998 |
| WO | WO98/53817 | 12/1998 |
| WO | WO98/53818 | 12/1998 |
| WO | WO99/06432 | 2/1999 |
| WO | WO 99/06433 | 2/1999 |
| WO | WO99/06434 | 2/1999 |
| WO | WO99/10312 | 3/1999 |
| WO | WO 99/26921 | 6/1999 |
| WO | WO99/26922 | 6/1999 |
| WO | WO99/26923 | 6/1999 |
| WO | WO 99/61421 | 12/1999 |
| WO | WO 00/47564 | 8/2000 |

OTHER PUBLICATIONS

Theien, et al., Blood, vol. 102(13), pp. 4464-4471 (2003).*
Leone, et al., J. of Pharmacology and Experimental Therapeutics, vol. 305(3), pp. 1150-1162 (2003).*
Egger, et al., J. of Pharmacology and Experimental Therapeutics, vol. 306(3), pp. 903-913(2003).*
Abraham et al., "$\alpha_4$-Integrins Mediate Antigen-induced Late Bronchial Responses and Prolonged Airway Hyperresponsiveness in sheep", J Clin. Invest., vol. 93, pp. 776-787, (1994).
Bajusz et al., "Design and Synthesis of Peptide Inhibitors of Blood Coagulation", Folia Haematol., Leipzig, vol. 109, pp. 16-21, (1982).
Baldwin et al., "An Efficient Substitute for the $\alpha$-aminoadipoyl Moiety of $\lambda$-(L-$\alpha$-amimoadipoyl)-L-cysteinyl-D-valine in the Enzymatic Synthesis of Penicillins", Tetrahedron, vol. 43, No. 18, pp. 4217-4220, (1987).
Chen et al., "Facile synthesis of N-protected peptide fragments using polymer-bound 1-hydroxybenzotriazole as an active ester", Chemical Abstracts, vol. 115, p. 1003, 115:159756r (1991).
Chisholm et al., "Monoclonal antibodies to the integrin $\alpha$-4 subunit inhibit the murine contact hypersensitivity response", European Journal of Immunology, vol. 23, pp. 682-688, (1993).
Elices et al., "Expression and Functional Significance of Alternatively Spliced CSI Fibronectin in Rheumatoid Arthritis Microvasculature", The Journal of Clinical Investigation, vol. 93, pp. 405-416, (1994).
Ferguson et al. "Antigen-Independent Processes in Antigen-Specific Immunity", The Journal of Immunology, vol. 150, No. 4, pp. 1172-1182, (1993).

(Continued)

*Primary Examiner*—James O. Wilson
*Assistant Examiner*—Nyeemah Grazier
(74) *Attorney, Agent, or Firm*—Steptoe & Johnson LLP

(57) ABSTRACT

Cell adhesion inhibitors can interact with VLA-4 molecules and inhibits VLA-4 dependent cell adhesion. An inhibitor including a polyethylene glycol moiety can have advantageous pharmaceutical properties.

87 Claims, 4 Drawing Sheets

OTHER PUBLICATIONS

Ferguson et al., "Two integrin-binding peptides abrogate T cell-mediated immune responses *in vivo*", Proceedings of the National Academy of Sciences USA, vol. 88, pp. 8072-8076, (1991).

Goodman et al., "Synthesis and Conformation of Sequential Polypeptides of L-Alanine and beta-Aminobutyric Acid", Macromolecules, vol. 9, No. 1, pp. 1-6, (1976).

Greenstein et al., "Chemistry of the Amino Acids," John Wiley and Sons, Inc., vol. 2, pp. 1162-1186.

Gruszecki et al., "Diacylamine-perfekte Acylierungsmittel fur die Peptidsynthese", Liebigs Ann. Chem., pp. 331-336, (1988).

Hemler, "VLA Proteins in the Integrin Family: Structures. Functions. and Their Role on Leukocytes", Annual Review of Immunology, vol. 8, pp. 365-400, (1990).

Jiang et al., "Approaches Toward the Total Synthesis of Astins A, B, And C", Tetrahedron Letters, vol. 35, No. 14, pp. 2121-2124, (1994).

Kim et al., "Inhibition of $^{125}$I-Labeled Ristocetin Binding to *Micrococcus luteus* Cells by the Peptides Related to Bacterial Cell Wall Mucopeptide Precursors: Quantitative Structure-Activity Relationships", Journal of Medical Chemistry, vol. 32, No. 1, pp. 84-93, (1989).

Komoriya et al., "The Minimal Essential Sequence for a Major Cell Type-specific Adhesion site (CSI) within the Alternatively Spliced . . . ", Journal of Biological Chemistry, vol. 266, No. 23, pp. 15075-15079, (1991).

Lampi, et al., "Comparison of Cell-Permeable Calpain Inhibitors and E64 in Reduction of Cataract in Cultured Rat Lenses", Toxicology and Applied Pharmacology, vol. 117, pp. 53-57, (1992).

Lin, Ko-Chung, et al., "Selective, Tight Binding Inhibitors of Integrin α4β1 That Inhibit Allergic Airway Responses", Journal of Medicinal Chemistry, vol. 42, No. 5, pp. 920-934, (1999).

Lobb et al., "The Pathophysiologic Role of α4 Integrins in Vivo", The Journal of Clinical Investigation, vol. 94, pp. 1722-1728, (1994).

Melmon et al., "III Drug Interactions", The Pharmacological Basis of Therapeutics, 6$^{th}$ Edition, MacMillan Publishing Co., Inc. © 1980, pp. 1738-1740.

Molossi et al., "Blockade of Very Late Antigen-4 Integrin binding to Fibronectin with Connecting Segment-1 Peptide Reduces Accelerated Coronary Arteriopathy . . . ", Journal of Clinical Investigation, vol. 95, pp. 2601-2610, (1995).

Morales-Ducret et al., "α$_4$/ β1 INTEGRIN (VLA-4) Ligands In Arthritis Vascular Cell Adhesion Molecule-1 Expression in Synovium and on . . . ", The Journal of Immunology, vol. 149, No. 4, pp. 1424-1431, (1992).

Narumiya et al., "Pre-B cells adhere to fibronectin via interactions of integrin α5/αv with RGDS as well as of integrin α4 with two distinct V region sequences at its different biding sites", Intl. Immun., vol. 6, No. 1, pp. 139-147, (1994).

Nowlin et al., "A Novel Cyclic Pentapeptide Inhibits α4β1 Integrin-mediated Cell Adhesion", The Journal of Biological Chemistry, vol. 25, No. 27, pp. 20352-20359, (1993).

Sawyer, T. K., "Peptidomimetic Design and Chemical Approaches to Peptide Metabolism", Peptide-Based Drug Design: controlling transport and metabolism © 1995, ACS Professional Reference Book, pp. 387-442.

Subasinghe et al., "Synthesis of Acyclic and Dehydroaspartic Acid Analogues of Ac-Asp-Glu-OH and Their Inhibition of Rat Brain N-Acetylated α-Linked Acidic Dipeptidase (NAALA Dipeptidase)", Journal of Medicinal Chemistry, vol. 33, No. 10, pp. 2734-2744, (1990).

Thierry et al., "Synthesis and Activity of NAcSerAspLysPro Analogues on Cellular Interactions between T-Cell and Erythrocytes in Rosette Formation," Jouranl of Medical Chemistry, vol. 33, pp. 2122-2127, (1990).

Wayner et al., "Activation-dependent Recognition by Hematopoietic Cells of the LDV Sequence in the V Region of Fibronectin", The Journal of Cell Biology, vol. 16, No. 2, pp. 489-497, (1992).

Yednock et al., "Prevention of experimental autoimmune encephalomyelitis by antibodies against α4 β1 integrin", Nature, vol. 356, pp. 63-66, (1992).

Zimmerman, Craig N., "Peptide and peptodomimetic inhibitors of VLA-4", Expert Opinion of Therapeutic Patents, Ashley Publication, GB, vol. 9, No. 2, pp. 129-133, (1999).

\* cited by examiner

CELL ADHESION INHIBITORS

TECHNICAL FIELD

This invention relates to compounds that inhibit cell adhesion.

BACKGROUND

Cell adhesion is a process by which cells associate with each other, migrate towards a specific target or localize within the extra-cellular matrix. As such, cell adhesion constitutes one of the fundamental mechanisms underlying numerous biological phenomena. For example, cell adhesion is responsible for the adhesion of hematopoietic cells to endothelial cells and the subsequent migration of those hematopoietic cells out of blood vessels and to the site of injury. Thus, cell adhesion plays a role in pathologies such as inflammation and immune reactions in mammals.

Integrins are a large family of cell surface receptors that mediate cell-cell and cell-matrix interaction. They exist as non-covalent αβ heterodimers of different combinations of α and β chains and share extensive structural homology. There are at least 18 different α subunits (α1α11, α-L, α-M, α-X, α-IIB, α-V and α-E) and at least 9 different β (β1–β9) subunits. Based on the composition of its α and β subunit components, each integrin molecule is categorized into a subfamily. Integrins mediate a wide variety of physiological processes and are relevant to a wide variety of pathological conditions. During inflammatory responses, α4β1 regulates leukocyte migration into the damaged tissues and thus has been recognized as an attractive therapeutic target. α4β1 integrin is also known as very late antigen-4 ("VLA-4") or CD49d/CD29.

SUMMARY

Novel non-peptidic compounds can specifically inhibit the binding of ligands to VLA-4. These compounds can be useful for inhibition, prevention and suppression of VLA-4-mediated cell adhesion and pathologies associated with that adhesion, such as inflammation and immune reactions. The compounds may be used alone or in combination with other therapeutic or prophylactic agents to inhibit, prevent or suppress cell adhesion. Pharmaceutical compositions containing the compounds and methods of using the compounds and compositions for inhibition of cell adhesion are also provided.

In one aspect, a compound has the formula:

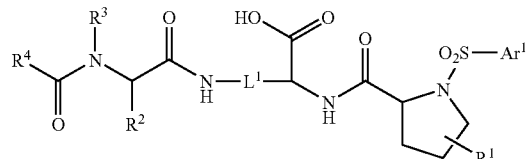

$Ar^1$ can be an aryl group. $L^1$ can be a $C_1$–$C_4$ alkylene group. $R^1$ can be hydrogen or can be a moiety having the formula —$R^5$-$L^2$-(O-$L^3$-)$_n$O$R^6$. $R^2$ can be a $C_1$–$C_{10}$ alkyl, aminoalkyl, thioalkyl, arylalkyl, or hydroxyalkyl group, or can be a moiety having the formula —$R^5$-$L^2$-(O-$L^3$-)$_n$O$R^6$. $R^3$ can be hydrogen or a $C_1$–$C_6$ alkyl group. $R^4$ can be an aralkyl group. At least one of $R^1$ or $R^2$ includes a moiety having the formula —$R^5$-$L^2$-(O-$L^3$-)$_n$O$R^6$. n can be an integer chosen such that the compound has a molecular weight between 400 and 70,000.

Each $R^5$, independently, can be a bond, —C(O)—, —C(O)—O—, —O—C(O)—, —S(O)$_p$—O—, —O—S(O)$_p$—, —C(O)—N($R^a$)—, —O—C(O)—N($R^a$)—, —N($R^a$)—C(O)—, —N($R^a$)—, C(O)—O—, —O—S(O)$_p$—N($R^a$)—, —N($R^a$)—S(O)$_p$—O—, —N($R^a$)—C(O)—N($R^b$)—, —N($R^a$)—S(O)$_p$—N($R^b$)—, —C(O)—N($R^a$)—S(O)$_p$—, —S(O)$_p$—N($R^a$)—C(O)—, —C(O)—N($R^a$)—S(O)$_p$—N($R^b$)—, —C(O)—O—S(O)$_p$—N($R^a$)—, —S(O)$_p$—, —O—, —S—, or —(C($R^a$)($R^b$))$_q$—. Each of $R^a$ and $R^b$, independently, can be hydrogen, hydroxy, alkyl, alkoxy, amino, aryl, aralkyl, heterocycloalkyl, heteroaryl, or heteroaralkyl. p can be 1 or 2, and q can be 1, 2, 3, or 4.

Each $L^2$, independently, can be a bond, aryl, heteroaryl, cycloalkyl, heterocyclyl, or a $C_1$–$C_{20}$ alkylene group, where $L^2$ can be optionally interrupted or terminated by one or more of —C(O)—, —C(O)—O—, —O—C(O)—, —S(O)$_p$—O—, —O—S(O)$_p$—, —C(O)—N($R^a$)—, —O—C(O)—N($R^a$)—, —N($R^a$)—S(O)$_p$—N($R^b$)—, —C(O)—N($R^a$)—S(O)$_p$—, —S(O)$_p$—N($R^a$)—C(O)—, —C(O)—N($R^a$)—S(O)$_p$—N($R^b$)—, —N($R^a$)—S(O)$_p$—N($R^b$)—, —C(O)—N($R^a$)—S(O)$_p$—, —S(O)$_p$—N($R^a$)—C(O)—, —C(O)—N($R^a$)—S(O)$_p$—N($R^b$)—, —C(O)—O—S(O)$_p$—N($R^a$)—, —N($R^a$)—S(O)$_p$—N($R^b$)—C(O)—, —N($R^a$)—S(O)$_p$—O—C(O)—, —S(O)$_p$—N($R^a$)—, —N($R^a$)—S(O)$_p$—, —N($R^a$)—, —S(O)$_p$—, —O—, —S—, or —(C($R^a$)($R^b$))$_q$—. Each of $R^a$ and $R^b$, independently, can be hydrogen, hydroxy, alkyl, alkoxy, amino, aryl, aralkyl, heterocycloalkyl, heteroaryl, or heteroaralkyl. p can be 1 or 2, and q can be 1, 2, 3, or 4.

Each $L^3$, independently, can be a $C_1$–$C_6$ alkylene group.

Each $R^6$, independently, can be hydrogen, a $C_1$–$C_6$ alkyl group, an aryl group, can be a moiety having the formula:

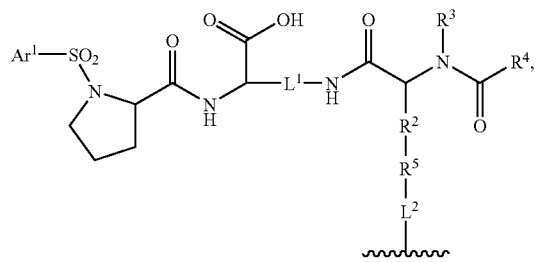

or can be a moiety having the formula:

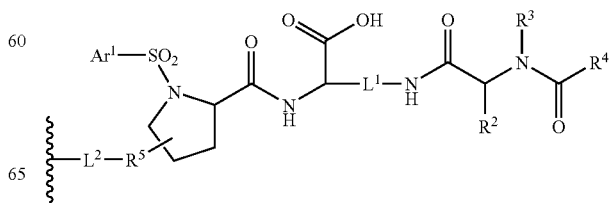

where $R^2$ is a $C_1$–$C_{10}$ alkyl, aminoalkyl, thioalkyl, arylalkyl, or hydroxyalkyl group.

When $Ar^1$ is phenyl, $L^1$ is —$CH_2CH_2$—, $R^2$ is 2-methylpropyl, $R^3$ is methyl, and $R^4$-((N'-2-methylphenyl)ureido)benzyl, $R^1$ is not —N(H)—C(O)—$CH_2CH_2$—(O$CH_2CH_2$)$_n$—O$CH_3$ where n is selected such that $R^1$ has a molecular weight of approximately 20,000, and $R^1$ is not —N(H)—C(O)—($CH_2$)$_5$—N(H)—C(O)—$CH_2CH_2$—(O$CH_2CH_2$)$_n$—O$CH_3$, where n is selected such that $R^1$ has a molecular weight of approximately 20,000, 30,000 or 50,000.

In one embodiment, $R^4$ can a N-arylurea-substituted aralkyl group. $R^4$ can have the formula:

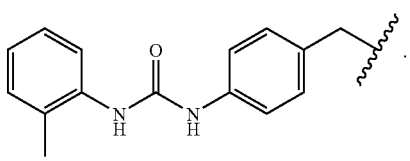

$L^1$ can be a $C_1$, $C_2$ or $C_3$ alkylene group. $Ar^1$ can be phenyl optionally substituted by 1, 2, 3, 4 or 5 halo groups.

In another embodiment, $R^1$ can have the formula —$R^5$-$L^2$-(O-$L^3$-)$_n$O$R^6$. Each $L^3$ can be —$CH_2$—$CH_2$—. $R^5$ can be —N($R^a$)—C(O)—. $R^1$ can be in an anti configuration or in a syn configuration. In other words, $R^1$ can be anti (i.e. on opposite faces of the pyrrolidine ring) or syn (i.e. on the same face of the pyrrolidine ring) with respect to the carbamoyl substituent at the 2-position of the pyrrolidine ring.

In another embodiment, $R^6$ can be $C_1$–$C_6$ alkyl.

In another embodiment, $R^2$ can be 2-methylpropyl. $L^1$ can be —$CH_2$—$CH_2$—. $R^1$ can have the formula —$R^5$-$L^2$-(O-$L^3$-)$_n$O$R^6$. Each $L^3$ can be —$CH_2$—$CH_2$—. $R^6$ can be —$CH_3$.

In another embodiment, $R^1$ can be hydrogen and $R^2$ has the formula —$R^5$-$L^2$-(O-$L^3$-)$_n$O$R^6$. —$R^5$-$L^2$- can be —($CH_2$)$_4$—N(H)—C(O)—($CH_2$)$_5$—N(H)—C(O)—($CH_2$)$_2$—. Each $L_3$ can be —$CH_2$—$CH_2$—. $R^6$ can be —$CH_3$.

In another aspect, a compound has the formula:

$Ar^1$ can be an aryl group. $R^1$ can be a moiety having the formula —$R^5$-$L^2$-(O-$L^3$-)$_n$O$R^6$. n can be an integer chosen such that the compound has a molecular weight between 400 and 70,000.

$R^5$ can be a bond, —C(O)—, —C(O)—O—, —O—C(O)—, —S(O)$_p$—O—, —O—S(O)$_p$—, —C(O)—N($R^a$)—, —O—C(O)—N($R^a$)—, —N($R^a$)—C(O)—, —N($R^a$)—C(O)—O—, —O—S(O)$_p$—N($R^a$)—, —N($R^a$)—S(O)$_p$—O—, —N($R^a$)—C(O)—N($R^b$)—, —N($R^a$)—S(O)$_p$—N($R^b$)—, —C(O)—N($R^a$)—S(O)$_p$—, —S(O)$_p$—N($R^a$)—C(O)—, —C(O)—N($R^a$)—S(O)$_p$—N($R^b$)—, —C(O)—O—S(O)$_p$—N($R^a$)—, —N($R^a$)—S(O)$_p$—N($R^b$)—C(O)—, —N($R^a$)—S(O)$_p$—O—C(O)—, —S(O)$_p$—N($R^a$)—, —N($R^a$)—S(O)$_p$—, —N($R^a$)—, —S(O)$_p$—, —O—, —S—, or —(C($R^a$)($R^b$))$_q$—. Each of $R^a$ and $R^b$, independently, can be hydrogen, hydroxy, alkyl, alkoxy, amino, aryl, aralkyl, heterocycloalkyl, heteroaryl, or heteroaralkyl. p can be 1 or 2, and q can be 1, 2, 3, or 4.

$L^2$ can be a bond, aryl, heteroaryl, cycloalkyl, heterocyclyl, or a $C_1$–$C_{20}$ alkylene group. $L^2$ can be optionally interrupted or terminated by one or more of —C(O)—, —C(O)—O—, —O—C(O)—, —S(O)$_p$—O—, —O—S(O)$_p$—, —C(O)—N($R^a$)—, —O—C(O)—N($R^a$)—, —N($R^a$)—C(O)—, —N($R^a$)—C(O)—O—, —O—S(O)$_p$—N($R^a$)—, —N($R^a$)—S(O)$_p$—O—, —N($R^a$)—C(O)—N($R^b$)—, —N($R^a$)—S(O)$_p$—N($R^b$)—, —C(O)—N($R^a$)—S(O)$_p$—, —S(O)$_p$—N($R^a$)—C(O)—, —C(O)—N($R^a$)—S(O)$_p$—N($R^b$)—, —C(O)—O—S(O)$_p$—N($R^a$)—, —N($R^a$)—S(O)$_p$—N($R^b$)—C(O)—, —N($R^a$)—S(O)$_p$—O—C(O)—, —S(O)$_p$—N($R^a$)—, —N($R^a$)—S(O)$_p$—, —N($R^a$)—, —S(O)$_p$—, —O—, —S—, or —(C($R^a$)($R^b$))$_q$—. Each of $R^a$ and $R^b$, independently, can be hydrogen, hydroxy, alkyl, alkoxy, amino, aryl, aralkyl, heterocycloalkyl, heteroaryl, or heteroaralkyl. p can be 1 or 2, and q can be 1, 2, 3, or 4.

Each $L^3$, independently, can be a $C_1$–$C_6$ alkylene group.

$R^6$ can be hydrogen, a $C_1$–$C_6$ alkyl group, an aryl group, or can be a moiety having the formula:

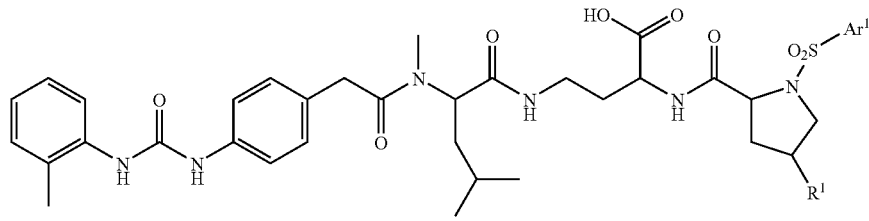

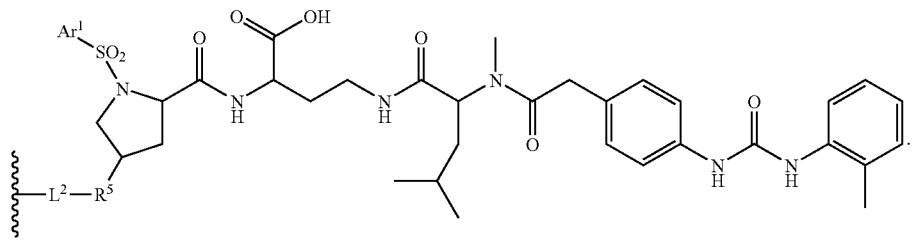

When $Ar^1$ is phenyl, $R^1$ is not —N(H)—C(O)—$CH_2CH_2$—$(OCH_2CH_2)_n$—$OCH_3$ where n is selected such that $R^1$ has a molecular weight of approximately 20,000, and $R^1$ is not —N(H)—C(O)—$(CH_2)_5$—N(H)—C(O)—$CH_2CH_2$—$(OCH_2CH_2)_n$—$OCH_3$, where n is selected such that $R^1$ has a molecular weight of approximately 20,000, 30,000 or 50,000.

In one embodiment, $Ar^1$ can be phenyl optionally substituted by 1, 2, 3, 4 or 5 halo groups. $R^5$ can be —N($R^a$)—C(O)—.

In another embodiment, each $L^3$ can be —$CH_2$—$CH_2$—. $R^6$ can be $C_1$–$C_6$ alkyl. $R^6$ can be —$CH_3$.

In another aspect, a compound has the formula:

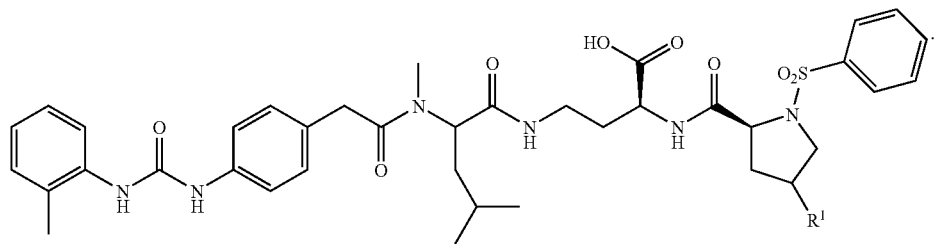

$R^1$ can be a moiety having the formula —$R^5$-$L^2$-$(O-L^3-)_n$ $OR^6$. n can be an integer chosen such that the compound has a molecular weight between 400 and 70,000.

$R^5$ can be a bond, —C(O)—, —C(O)—O—, —O—C(O)—, —S(O)$_p$—O—, —O—S(O)$_p$—, —C(O)—N($R^a$), —O—C(O)—N($R^a$)—, —N($R^a$)—C(O)—, —N($R^a$)—C(O)—O—, —O—S(O)$_p$—N($R^a$)—, —N($R^a$)—S(O)$_p$—O—, —N($R^a$)—C(O)—N($R^b$)—, —S(O)$_p$—N($R^a$)—, —N($R^a$)—S(O)$_p$—, —N($R^a$)—, —S(O)$_p$—, —O—, —S—, or —$(C(R^a)(R^b))_q$—. Each of $R^a$ and $R^b$, independently, can be hydrogen, hydroxy, alkyl, alkoxy, amino, aryl, aralkyl, heterocycloalkyl, heteroaryl, or heteroaralkyl. p can be 1 or 2, and q can be 1, 2, 3, or 4.

$L^2$ can be a bond, aryl, heteroaryl, cycloalkyl, heterocyclyl, or a $C_1$–$C_{20}$ alkylene group. $L^2$ can be optionally interrupted or terminated by one or more of —C(O)—, —C(O)—O—, —O—C(O)—, —S(O)$_p$—O—, —O—S(O)$_p$—, —C(O)—N($R^a$)—, —O—C(O)—N($R^a$)—, —N($R^a$)—C(O)—, —N($R^a$)—C(O)—O—, —O—S(O)$_p$—N($R^a$)—, —N($R^a$)—S(O)$_p$—O—, —N($R^a$)—C(O)—N($R^b$)—, —S(O)—N($R^a$)—, —N($R^a$)—S(O)$_p$—, —N($R^a$)—, —S(O)$_p$—, —O—, —S—, or —$(C(R^a)(R^b))_q$—. Each of $R^a$ and $R^b$, independently, can be hydrogen, hydroxy, alkyl, alkoxy, amino, aryl, aralkyl, heterocycloalkyl, heteroaryl, or heteroaralkyl. p can be 1 or 2, and q can be 1, 2, 3, or 4.

Each $L^3$, independently, can be a $C_1$–$C_6$ alkylene group.

$R^6$ can be hydrogen, a $C_1$–$C_6$ alkyl group, or an aryl group.

$R^1$ is not —N(H)—C(O)—$CH_2CH_2$—$(OCH_2CH_2)_n$—$OCH_3$ where n is selected such that $R_1$ has a molecular weight of approximately 20,000, and $R^1$ is not —N(H)—C(O)—$(CH_2)_5$—N(H)—C(O)—$CH_2CH_2$—$(OCH_2CH_2)_n$—$OCH_3$, where n is selected such that $R^1$ has a molecular weight of approximately 20,000, 30,000 or 50,000.

In another aspect, a compound has the formula:

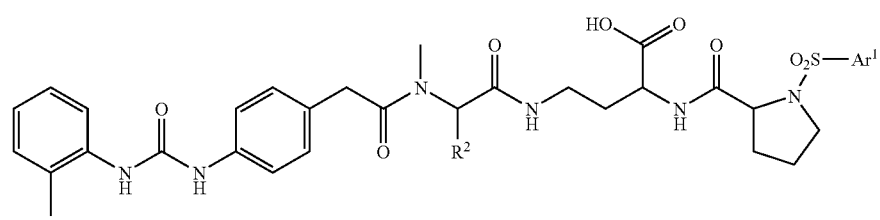

Ar$^1$ can be an aryl group. R$^2$ can be a moiety having the formula —R$^5$-L$^2$-(O-L$^3$-)$_n$OR$^6$. n can be an integer chosen such that the compound has a molecular weight between 400 and 70,000.

R$^5$ can be a bond, —C(O)—, —C(O)—O—, —O—C(O)—, —S(O)$_p$—O—, —O—S(O)$_p$—, —C(O)—N(R$^a$)—, —O—C(O)—N(R$^a$)—, —N(R$^a$)—C(O)—, —N(R$^a$)—C(O)—O—, —O—S(O)$_p$—N(R$^a$)—, —N(R$^a$)—S(O)$_p$—O—, —N(R$^a$)—C(O)—N(R$^b$)—, —N(R$^a$)—S(O)$_p$—N(R$^b$)—, —C(O)—N(R$^a$)—S(O)$_p$—, —S(O)$_p$—N(R$^a$)—C(O)—, —C(O)—N(R$^a$)—S(O)$_p$—N(R$^b$)—, —C(O)—O—S(O)$_p$—N(R$^a$)—, —N(R$^a$)—S(O)$_p$—N(R$^b$)—C(O)—, —N(R$^a$)—S(O)$_p$—O—C(O)—, —S(O)$_p$—N(R$^a$)—, —N(R$^a$)—S(O)$_p$—, —N(R$^a$)—, —S(O)$_p$—, —O—, —S—, or —(C(R$^a$)(R$^b$))$_q$—. Each of R$^a$ and R$^b$, independently, can be hydrogen, hydroxy, alkyl, alkoxy, amino, aryl, aralkyl, heterocycloalkyl, heteroaryl, or heteroaralkyl. p can be 1 or 2, and q can be 1, 2, 3, or 4.

L$^2$ can be a bond, aryl, heteroaryl, cycloalkyl, heterocyclyl, or a C$_1$–C$_{20}$ alkylene group. L$^2$ can be optionally interrupted or terminated by one or more of —C(O)—, —C(O)—O—, —O—C(O)—, —S(O)$_p$—O—, —O—S(O)$_p$—, —C(O)—N(R$^a$)—, —O—C(O)—N(R$^a$)—, —N(R$^a$)—C(O)—, —N(R$^a$)—C(O)—O—, —O—S(O)$_p$—N(R$^a$)—, —N(R$^a$)—S(O)$_p$—O—, —N(R$^a$)—C(O)—N(R$^b$)—, —N(R$^a$)—S(O)$_p$—N(R$^b$)—, —C(O)—N(R$^a$)—S(O)$_p$—, —S(O)$_p$—N(R$^a$)—C(O)—, —C(O)—N(R$^a$)—S(O)$_p$—N(R$^b$)—, —C(O)—O—S(O)$_p$—N(R$^a$)—, —N(R$^a$)—S(O)$_p$—N(R$^b$)—C(O)—, —N(R$^a$)—S(O)$_p$—O—C(O)—, —S(O)$_p$—N(R$^a$)—, —N(R$^a$)—S(O)$_p$—, —N(R$^a$)—, —S(O)$_p$—, —O—, —S—, or —(C(R$^a$)(R$^b$))$_q$—. Each of R$^a$ and R$^b$, independently, can be hydrogen, hydroxy, alkyl, alkoxy, amino, aryl, aralkyl, heterocycloalkyl, heteroaryl, or heteroaralkyl; p can be 1 or 2, and q can be 1, 2, 3, or 4.

Each L$^3$, independently, can be a C$_1$–C$_6$ alkylene group.

R$^6$ can be hydrogen, a C$_1$–C$_6$ alkyl group, or an aryl group.

Ar$^1$ can be phenyl optionally substituted by 1, 2, 3, 4 or 5 halo groups. R$^5$ can be —N(R$^a$)—C(O)—. Each L$^3$ can be —CH$_2$—CH$_2$—. R$^6$ can be C$_1$–C$_6$ alkyl. R$^6$ can be —CH$_3$. R$^2$ can have the formula:

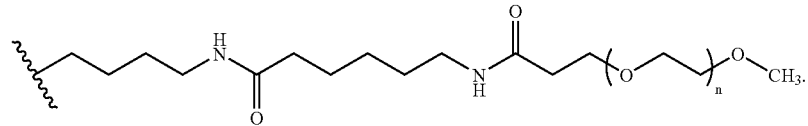

In another aspect, a compound has the formula:

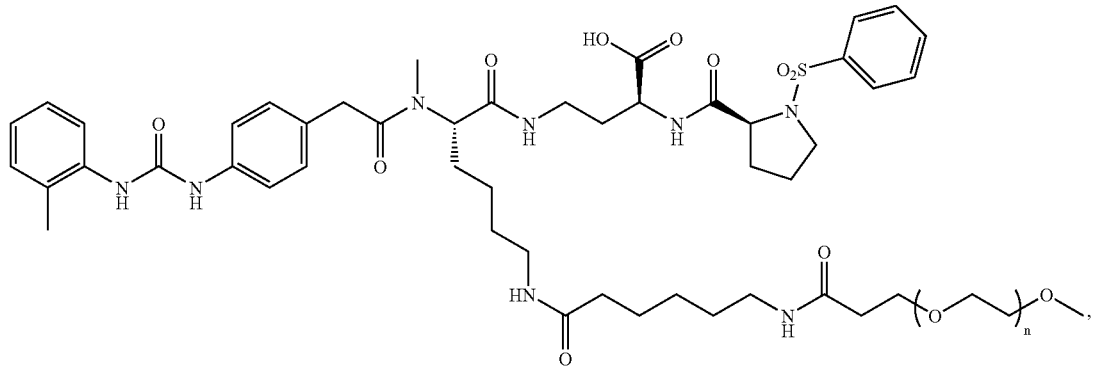

where n is an integer selected so that the compound has a molecular weight between 400 and 70,000.

In another aspect, a pharmaceutical composition can include a pharmaceutical carrier and the compound, or a pharmaceutically acceptable salt thereof.

In another aspect, a method of inhibiting VLA-4-dependent cell adhesion includes administering to a patient in need thereof an effective amount of the compound or a pharmaceutically acceptable salt thereof.

In another aspect, a method of inhibiting VLA-4-dependent cell adhesion includes administering to a patient in need thereof an effective amount of a compound capable of inhibiting the binding of a ligand to VLA-4, or a pharmaceutically acceptable salt thereof, wherein the compound includes a poly(ethylene glycol) moiety.

The compound can be water soluble. The compound can have a molecular weight between 1,000 and 60,000, or the compound can have a molecular weight between 10,000 and 30,000.

In another aspect, a method of making a cell adhesion inhibitor includes modifying a compound with a water soluble polymer. The method can include converting the modified compound to a cell adhesion inhibitor. The compound can be a cell adhesion inhibitor. The water soluble polymer includes a poly(oxyalkylene) moiety. The water soluble polymer can includes a poly(ethylene glycol) moiety or a poly(propylene glycol) moiety. The compound can include a nucleophilic group and the water soluble polymer can include an electrophilic group. The electrophilic group can be an activated ester group. The nucleophilic group can be an amine.

In another aspect, a method of making a cell adhesion inhibitor includes converting a 4-hydroxyproline moiety to a 4-aminoproline moiety. The conversion can be a stereospecific conversion. The 4-aminoproline moiety can be incorporated in a cell adhesion inhibitor. The 4-aminoproline moiety can be modified with a water soluble polymer. The water soluble polymer can include a poly(oxyalkylene) moiety. The water soluble polymer can include a poly(ethylene glycol) moiety or a poly(propylene glycol) moiety.

The ability of the compounds to antagonize the actions of VLA-4 makes them useful for preventing, treating, or reversing the symptoms, disorders or diseases induced by the binding of VLA-4 to its ligands. Thus these antagonists can inhibit cell adhesion processes including cell activation, migration, proliferation and differentiation. Accordingly, another aspect provides methods for the treatment, prevention, alleviation, or suppression of diseases or disorders mediated by the VLA-4 pathway. Such diseases and disorders include, for example, asthma, multiple sclerosis, allergic rhinitis, allergic conjunctivitis, inflammatory lung diseases, rheumatoid arthritis, septic arthritis, type I diabetes, organ transplant rejection, inflammatory bowel disease, and others.

A stabilizing group can enhance the pharmacokinetic or pharmacodynamic properties of a VLA-4 inhibitor. A stabilizing group can include a water soluble polymer, such as, for example, a polyethylene glycol (PEG) or polypropylene glycol (PPG) moiety. An inhibitor including a stabilizing PEG moiety can have advantages over a related inhibitor that lacks a PEG moiety in pharmacokinetics, pharmacodynamics, and efficacy in blocking the disease progression in a rat model of experimental autoimmune encephalomyelitis (EAE) responsive to α4-inhibitors. For example, an inhibitor having a PEG moiety can have greater water solubility, longer plasma circulating half-life, and longer elimination half-life than a related compound without a PEG moiety.

The compounds can contain one or more asymmetric centers and thus can occur as racemates and racemic mixtures, single enantiomers, diastereomeric mixtures and individual diastereomers.

The compounds can be prepared as salts, for example as pharmaceutically acceptable salts. The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, copper, ferric, ferrous, lithium, alkaline earth metal salts, such as calcium and magnesium, manganic salts, manganous, alkali metal salts, such as potassium and sodium, zinc, and the like. Particularly preferred are the ammonium, calcium, magnesium, potassium and sodium salts.

Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, dicyclohexylamine, diethylamine, 2-diethylaminoethanol, 2-dimethylaminoethanol, ethanolamine, ethylenediamine, N-ethylmorpholine, N-ethylpiperidine, glucamine, N-methyl-D-glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. Also, the basic nitrogen-containing groups can be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others.

When the compound is basic, salts may be prepared from pharmaceutically acceptable non-toxic acids, including inorganic and organic acids. Included among such acid salts are acetate, adipate, alginate, aspartate, benzenesulfonate, benzoate, bisulfate, butyrate, camphorate, camphorsulfonate, citrate, cyclopentanepropionate, digluconate, dodecylsulfate, ethanesulfonate, fumarate, gluconate, glutamate, glucoheptanoate, glycerophosphate, hemisulfate, hexanoate, hydrobromide, hydrochloride, hydroiodide, 2-hydroxyethanesulfonate, isethionate, lactate, maleate, malate, mandelate, methanesulfonate, mucate, 2-naphthalenesulfonate, nicotinate, nitrate, oxalate, pamoate, pantothenate, pectinate, persulfate, 3-phenyl-propionate, picrate, pivalate, propionate, phosphate, succinate, sulfate, tartarate, thiocyanate, p-toluenesulfonate, undecanoate, and the like. Particularly preferred are citric, hydrobromic, hydrochloric, maleic, phosphoric, sulfuric and tartaric acids.

As used herein, the term "alkyl," alone or in combination, refers to a straight-chain or branched-chain alkyl radical containing from 1 to 10, preferably from 1 to 6 and more preferably from 1 to 4, carbon atoms. Examples of such radicals include, but are not limited to, methyl, ethyl, n-propyl, isopropyl, n-butyl, isobutyl, sec-butyl, tert-butyl, pentyl, iso-amyl, hexyl, decyl, and the like.

The term "alkenyl," alone or in combination, refers to a straight-chain or branched-chain alkenyl radical containing from 2 to 10, preferably from 2 to 6 and more preferably from 2 to 4, carbon atoms. Examples of such radicals include, but are not limited to, ethenyl, E- and Z-propenyl, isopropenyl, E- and Z-butenyl, E- and Z-isobutenyl, E- and Z-pentenyl, decenyl, and the like.

The term "alkynyl," alone or in combination, refers to a straight-chain or branched-chain alkynyl radical containing from 2 to 10, preferably from 2 to 6 and more preferably from 2 to 4, carbon atoms. Examples of such radicals include, but are not limited to, ethynyl (acetylenyl), propynyl, propargyl, butynyl, hexynyl, decynyl, and the like.

The term "hydrocarbon linker moiety" refers to an alkylene moiety which may contain one or more double or triple bonds. For example, a hydrocarbon linker moiety can be 3-methyloctylene (i.e., a straight chain containing 8 carbon chain atoms) interrupted by, or terminally attached to, an amide linkage (—NH—CO—).

The term "cycloalkyl," alone or in combination, refers to a cyclic alkyl radical containing from 3 to 8, preferably from 3 to 6, carbon atoms. Examples of such cycloalkyl radicals include, but are not limited to, cyclopropyl, cyclobutyl, cyclopentyl, cyclohexyl, and the like.

The term "cycloalkenyl," alone or in combination, refers to a cyclic carbocycle containing from 4 to 8, preferably 5 or 6, carbon atoms and one or more double bonds. Examples of such cycloalkenyl radicals include, but are not limited to, cyclopentenyl, cyclohexenyl, cyclopentadienyl, and the like.

The term "aryl" refers to a carbocyclic aromatic group selected from the group consisting of phenyl, naphthyl, indenyl, indanyl, azulenyl, fluorenyl, and anthracenyl; or a heterocyclic aromatic group selected from the group consisting of furyl, thienyl, pyridyl, pyrrolyl, oxazolyly, thiazolyl, imidazolyl, pyrazolyl, 2-pyrazolinyl, pyrazolidinyl, isoxazolyl, isothiazolyl, 1,2,3-oxadiazolyl, 1,2,3-triazolyl, 1,3,4-thiadiazolyl, pyridazinyl, pyrimidinyl, pyrazinyl, 1,3,5-triazinyl, 1,3,5-trithianyl, indolizinyl, indolyl, isoindolyl, 3H-indolyl, indolinyl, benzo[b]furanyl, 2,3-dihydrobenzofuranyl, benzo[b]thiophenyl, 1H-indazolyl, benzimidazolyl, benzthiazolyl, purinyl, 4H-quinolizinyl, quinolinyl, isoquinolinyl, cinnolinyl, phthalazinyl, quinazolinyl, quinoxalinyl, 1,8-naphthyridinyl, pteridinyl, carbazolyl, acridinyl, phenazinyl, phenothiazinyl, phenoxazinyl, and the like.

"Aryl" groups may independently contain one to three substituents which are independently selected from the group consisting of hydrogen, halogen, hydroxyl, amino, nitro, trifluoromethyl, trifluoromethoxy, alkyl, alkenyl, alkynyl, cyano, carboxy, carboalkoxy, Ar'-substituted alkyl, Ar'-substituted alkenyl or alkynyl, 1,2-dioxymethylene, 1,2-dioxyethylene, alkoxy, alkenoxy or alkynoxy, Ar'-substituted alkoxy, Ar'-substituted alkenoxy or alkynoxy, alkylamino, alkenylamino or alkynylamino, Ar'-substituted alkylamino, Ar'-substituted alkenylamino or alkynylamino, Ar'-substituted carbonyloxy, alkylcarbonyloxy, aliphatic or aromatic acyl, Ar'-substituted acyl, Ar'-substituted alkylcarbonyloxy, Ar'-substituted carbonylamino, Ar'-substituted amino, Ar'-substituted oxy, Ar'-substituted carbonyl, alkylcarbonylamino, Ar'-substituted alkylcarbonylamino, alkoxycarbonylamino, Ar'-substituted alkoxycarbonyl-amino, Ar'-oxycarbonylamino, alkylsulfonylamino, mono- or bis-(Ar'-sulfonyl) amino, Ar'-substituted alkyl-sulfonylamino, morpholinocarbonylamino, thiomorpholinocarbonylamino, N-alkyl guanidino, N-Ar' guanidino, N-N-(Ar',alkyl) guanidino, N,N-(Ar',Ar')guanidino, N,N-dialkyl guanidino, N,N,N-trialkyl guanidino, N-alkyl urea, N,N-dialkyl urea, N-Ar' urea, N,N-(Ar',alkyl) urea and N,N-(Ar')$_2$ urea; wherein Ar' is a carbocyclic or heterocyclic aryl group as defined above having one to three substituents selected from the group consisting of hydrogen, halogen, hydroxyl, amino, nitro, trifluoromethyl, trifluoromethoxy, alkyl, alkenyl, alkynyl, 1,2-dioxymethylene, 1,2-dioxyethylene, alkoxy, alkenoxy, alkynoxy, alkylamino, alkenylamino or alkynylamino, alkylcarbonyloxy, aliphatic or aromatic acyl, alkylcarbonylamino, alkoxycarbonylamino, alkylsulfonylamino, N-alkyl or N,N-dialkyl urea.

The term "alkoxy," alone or in combination, refers to an alkyl ether radical, wherein the term "alkyl" is as defined above. Examples of suitable alkyl ether radicals include, but are not limited to, methoxy, ethoxy, n-propoxy, iso-propoxy, n-butoxy, iso-butoxy, sec-butoxy, tert-butoxy, and the like.

The term "alkenoxy," alone or in combination, refers to a radical of formula alkenyl-O—, wherein the term "alkenyl" is as defined above provided that the radical is not an enol ether. Examples of suitable alkenoxy radicals include, but are not limited to, allyloxy, E- and Z-3-methyl-2-propenoxy and the like. The term "alkynyloxy", alone or in combination, refers to a radical of formula alkynyl-O—, wherein the term "alkynyl" is as defined above provided that the radical is not an ynol ether. Examples of suitable alkynoxy radicals include, but are not limited to, propargyloxy, 2-butynyloxy, and the like.

The term "thioalkoxy" refers to a thioether radical of formula alkyl-S—, wherein alkyl is as defined above.

The term "alkylamino," alone or in combination, refers to a mono- or di-alkyl-substituted amino radical (i.e., a radical of formula alkyl-NH— or (alkyl)$_2$-N—), wherein the term "alkyl" is as defined above. Examples of suitable alkylamino radicals include, but are not limited to, methylamino, ethylamino, propylamino, isopropylamino, t-butylamino, N,N-diethylamino, and the like.

The term "alkenylamino," alone or in combination, refers to a radical of formula alkenyl-NH— or (alkenyl)$_2$N—, wherein the term "alkenyl" is as defined above, provided that the radical is not an enamine. An example of such alkenylamino radicals is the allylamino radical.

The term "alkynylamino," alone or in combination, refers to a radical of formula alkynyl-NH— or (alkynyl)$_2$N—, wherein the term "alkynyl" is as defined above, provided that the radical is not an ynamine. An example of such alkynylamino radicals is the propargyl amino radical.

The term "aryloxy," alone or in combination, refers to a radical of formula aryl-O—, wherein aryl is as defined above. Examples of aryloxy radicals include, but are not limited to, phenoxy, naphthoxy, pyridyloxy, and the like.

The term "arylamino," alone or in combination, refers to a radical of formula aryl-NH—, wherein aryl is as defined above. Examples of arylamino radicals include, but are not limited to, phenylamino (anilido), naphthylamino, 2-, 3- and 4-pyridylamino, and the like.

The term "biaryl," alone or in combination, refers to a radical of formula aryl-aryl-, wherein the term "aryl" is as defined above.

The term "thioaryl," alone or in combination, refers to a radical of formula aryl-S—, wherein the term "aryl" is as defined above. An example of a thioaryl radical is the thiophenyl radical.

The term "aryl-fused cycloalkyl," alone or in combination, refers to a cycloalkyl radical which shares two adjacent atoms with an aryl radical, wherein the terms "cycloalkyl" and "aryl" are as defined above. An example of an aryl-fused cycloalkyl radical is the benzo-fused cyclobutyl radical.

The term "aliphatic acyl," alone or in combination, refers to radicals of formula alkyl-CO—, alkenyl-CO— and alkynyl-CO-derived from an alkane-, alkene- or alkyncarboxylic acid, wherein the terms "alkyl", "alkenyl" and "alkynyl" are as defined above. Examples of such aliphatic acyl radicals include, but are not limited to, acetyl, propionyl, butyryl, valeryl, 4-methylvaleryl, acryloyl, crotyl, propiolyl, methylpropiolyl, and the like.

The term "aromatic acyl," alone or in combination, refers to a radical of formula aryl-CO—, wherein the term "aryl" is as defined above. Examples of suitable aromatic acyl radicals include, but are not limited to, benzoyl, 4-halobenzoyl, 4-carboxybenzoyl, naphthoyl, pyridylcarbonyl, and the like.

The terms "morpholinocarbonyl" and "thiomorpholinocarbonyl," alone or in combination with other terms, refer to an N-carbonylated morpholino and an N-carbonylated thiomorpholino radical, respectively.

The term "alkylcarbonylamino," alone or in combination, refers to a radical of formula alkyl-CONH, wherein the term "alkyl" is as defined above.

The term "alkoxycarbonylamino," alone or in combination, refers to a radical of formula alkyl-OCONH—, wherein the term "alkyl" is as defined above.

The term "alkylsulfonylamino," alone or in combination, refers to a radical of formula alkyl-SO$_2$NH—, wherein the term "alkyl" is as defined above.

The term "arylsulfonylamino," alone or in combination, refers to a radical of formula aryl-SO$_2$NH—, wherein the term "aryl" is as defined above.

The term "N-alkylurea," alone or in combination, refers to a radical of formula alkyl-NH—CO—NH—, wherein the term "alkyl" is as defined above.

The term "N-arylurea," alone or in combination, refers to a radical of formula aryl-NH—CO—NH—, wherein the term "aryl" is as defined above.

The term "halogen" means fluorine, chlorine, bromine or iodine.

The term "leaving group" generally refers to groups readily displaceable by a nucleophile, such as an amine, and alcohol or a thiol nucleophile. Such leaving groups are well known and include carboxylates, N-hydroxysuccinimide, N-hydroxybenzotriazole, halogen (halides), triflates, tosylates, mesylates, alkoxy, thioalkoxy and the like.

The terms "activated derivative of a suitably protected α-amino acid" and "activated substituted-phenylacetic acid derivative" refer to the corresponding acyl halides (e.g. acid fluoride, acid chloride and acid bromide), corresponding activated esters (e.g. nitrophenyl ester, the ester of 1-hydroxybenzotriazole, HOBT, or the ester of hydroxysuccinimide, HOSu), and other conventional derivatives within the skill of the art.

The term "patient" refers to mammals, including humans. And the term "cell" refers to mammalian cells, including human cells.

In view of the above definitions, other chemical terms used throughout this application can be easily understood by those of skill in the art. Terms may be used alone or in any combination thereof. The preferred and more preferred chain lengths of the radicals apply to all such combinations.

The details of one or more embodiments are set forth in the accompanying drawings and the description below. Other features, objects, and advantages will be apparent from the description and drawings, and from the claims.

DETAILED DESCRIPTION

Figure 1:
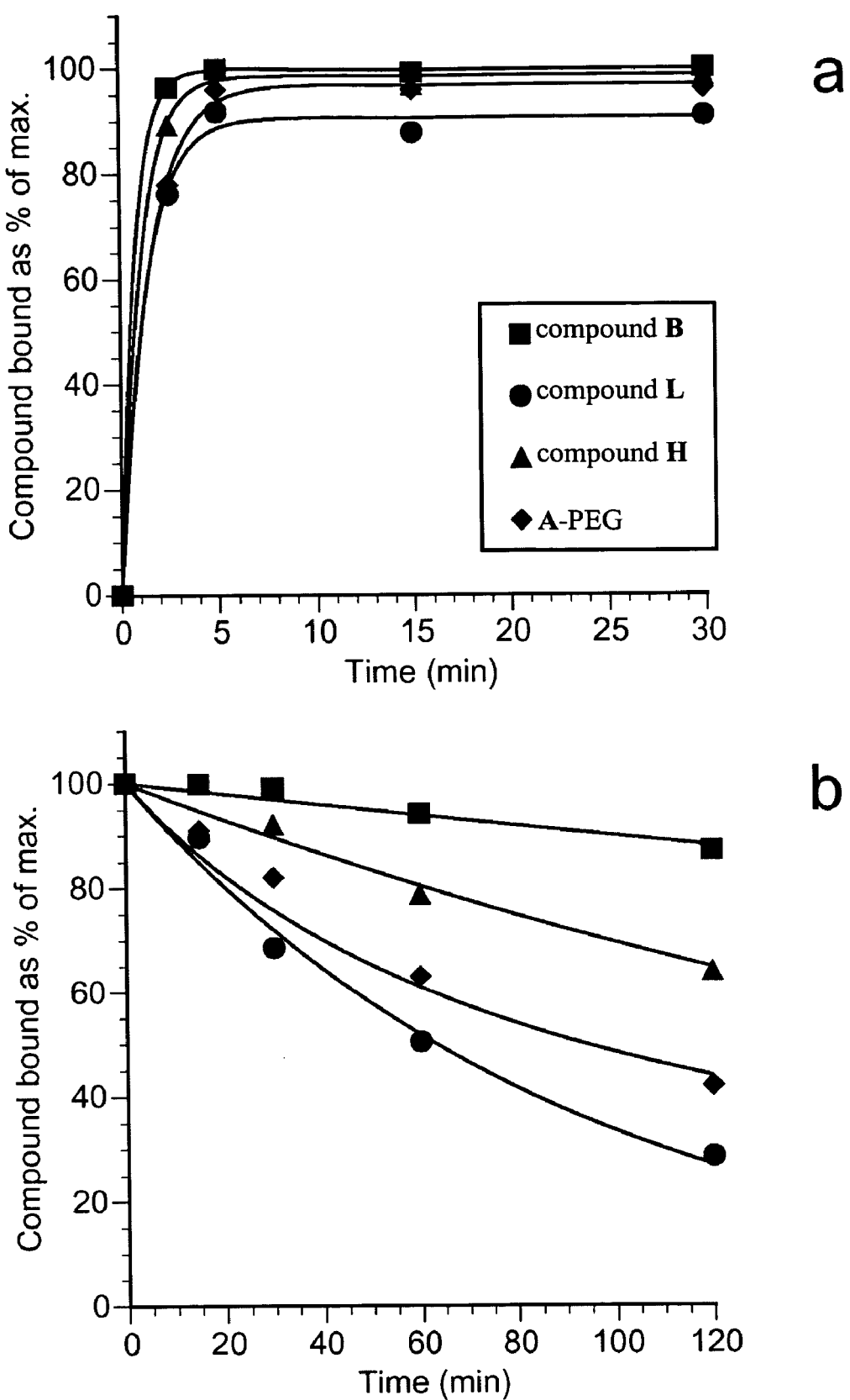
FIGS. 1a and 1b are graphs depicting the fraction of compounds bound to α4β1 as a function of time.

The integrin α4β1 regulates normal leukocyte trafficking and provides a key co-stimulatory signal supporting cell activation. See, for example, Lobb, R. R., et al. (1995) *Cell Adhes. Commun.* 3:385–397; Clark, E. A. and Brugge, J. S. (1995) *Science* 268:233–239, each of which is incorporated by reference in its entirety. During inflammatory responses, α4β1 regulates leukocyte migration into the damaged tissues and thus has been recognized as an attractive therapeutic target. In vivo studies using blocking monoclonal antibodies, inhibitory peptides, and small molecule antagonists have verified the critical role of α4β1 integrins in leukocyte-mediated inflammation and have implicated α4β1 inhibitors as potential treatments for diseases such as asthma and arthritis. See, for example, Lobb, R. R. and Hemler, M. E. (1994) *J. Clin. Invest.* 94:1722–1728; Issekutz, A. C., et al. (1996) *Immunology* 88:569–576; Enders, U., et al. (1998) *Brain* 121:1257–1266; Hojo, M., et al. (1998) *Am. J. Respir. Crit. Care Med.* 158:1127–1133; Schneider, T., et al. (1999) *Am. J. Respir. Cell Mol. Biol.* 20:448–457; Ramos-Barbon, D., et al. (2001) *Am. J. Respir. Crit. Care Med.* 163: 101–108; Molossi, S., et al. (1995) *J. Cell Physiol.* 164: 620–633; Abraham, W. M. (1997) *Am. J. Respir. Crit. Care Med.* 156:696–703; van der Laan, L. J., et al. (2002) *J. Neurosci. Res.* 67:191–199; Lin, K., et al. (1999) *J. Med. Chem.* 42:920–934; and Kudlacz, E., et al. (2002) *JPET* 301:747–752, each of which is incorporated by reference in its entirety.

Numerous EAE models that recapitulate important aspects of human multiple sclerosis are also responsive to both monoclonal antibodies (mAbs) and small molecule α4 inhibitors (see Yednock, T. A., et al. (1992) *Nature* 356: 63–66; Piraino, P. S., et al. (2002) *J. Neuroimmunol.* 131: 147–159; Kanwar, J. R., et al. (2000) *Immunol. Cell Biol.* 78:641–645; and Leone, D. R., et al. (2003) *J. Pharmacol. Exp. Ther.* 305:1150–1162, each of which is incorporated by reference in its entirety). Recent positive phase II data using the anti-α4 antibody Natalizumab in patients with multiple sclerosis have validated α4β1 as an important clinical target (see Miller, D. H., et al. (2003) *N. Eng. J. Med.* 348:15–23 which is incorporated by reference in its entirety).

Integrin α4β1 mediates cell adhesion by binding to either of two protein ligands, vascular cell adhesion molecule-1 (VCAM-1), or the alternatively spliced connecting segment 1 (CS1)-containing fibronectin variant (see Osborn, L., et al. (1989) *Cell* 59:1203–1211; and Wayner, E. A., et al. (1989) *J. Cell. Biol.* 109:1321–1330, each of which is incorporated by reference in its entirety). More recently, other potential ligands have been identified; however, the biological significance of these interactions is less clear (see Bayless, K. J., et al. (1998) *J. Cell Sci.* 111:1165–1174; and Takahashi, H., et al. (2000) *J. Biol. Chem.* 275:23589–23595, each of which is incorporated by reference in its entirety). The interactions between α4β1 and its ligands are of low affinity and binding presumably is modulated through multivalent interactions. While expression of α4β1 is constitutive, its interactions with ligands are strongly enhanced in an activated state that can be induced by various stimuli including antigen, anti-T-cell receptor mAbs, phorbol esters, the divalent cation $Mn^{2+}$, and certain β1-specific antibodies. These changes in affinity and/or avidity ultimately determine whether an interaction is productive and stabilizes the ligand/integrin complex (see Humphries, M., (1996) *Curr. Opin. Cell Biol.* 8:632–640; Chen, L. L., et al. (2001) *J. Biol. Chem.* 276:36520–36529, each of which is incorporated by reference in its entirety). The key residues in VCAM-1 (QIDSP) and CS1 (EILDVP) necessary for their interactions with α4β1 have been defined by molecular and biochemical techniques (see Wayner, E. A. and Kovach, N. L. (1992) *J. Cell Biol.* 116:489–497; and Wang, J. H., et al. (1995) *Proc. Natl. Acad. Sci. USA* 92:5714–5718, each of which is incorporated by reference in its entirety). Many groups have used these sequences as starting points to develop small molecule inhibitors that can block the interaction between α4β1 and its ligands (see, for example, Abraham, W. M. (1997) *Am. J. Respir. Crit. Care Med.* 156:696–703; Lin, K., et al. (1999) *J. Med. Chem.* 42:920–934; Kudlacz, E., et al. (2002) *JPET* 301:747–752; and van der Laan, L. J., et al. (2002) *J. Neurosci. Res.* 67:191–199).

An inhibitor having high affinity for α4β1 under all states of activation, high selectivity for α4β1, and a slow dissociation rate from the bound complex can be efficacious in various animal models of inflammatory disease. If the inhibitor has a relatively short serum half-life, high doses of the compound and daily treatment can be required to achieve therapeutic effects (see, for example, Leone, D. R., et al. (2003) *J. Pharmacol. Exp. Ther.* 305:1150–1162, which is incorporated by reference in its entirety). In order to reduce the amount or frequency of compound needed for activity, polyethylene glycol modification (PEGylation) of the compound can be used to improve its systemic exposure (see, for example, Delgado, C., et al. (1992) *Crit. Rev. Ther. Drug Carrier Sys.* 9: 249–304; Francis, G. E., et al. (1998) *Int. J. Hemat.* 68: 1–18; and Pepinsky, R. B., et al. (2001) *J. Pharmacol. Exp. Ther.* 297:1059–1066, each of which is incorporated by reference in its entirety).

The compounds may be synthesized using any conventional technique, several of which are exemplified herein. Preferably, the compounds are chemically synthesized from readily available starting materials, such as α-amino acids and their functional equivalents. Modular and convergent methods for the synthesis of these compounds are also preferred. In a convergent approach, for example, large sections of the final product are brought together in the last stages of the synthesis, rather than by incremental addition of small pieces to a growing molecular chain. The compounds can be purified by conventional methods such as chromatography or crystallization.

Proper protecting groups are required to prevent certain functionalities from undergoing undesired reactions. For example, common amino protecting groups such as carbamates (e.g., t-butyl carbamate (BOC) and benzyl carbamate (CBZ)) and common carboxylprotecting groups such as substituted esters (e.g., ethyl ester and methoxymethyl ester) can be used. For additional protecting groups, see, for example, T. W. Greene, Protecting Groups in Organic Synthesis, $3^{rd}$ ed., John Wiley & Sons, New York, 1999, which is incorporated by reference in its entirety, and references cited therein.

The compounds may also be modified by appending appropriate functionalities to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion. Examples of these modifications include, but are not limited to, esterification with polyethylene glycols, derivatization with pivolates or fatty acid substituents, conversion to carbamates, hydroxylation of aromatic rings, and heteroatom-substitution in aromatic rings.

In general, a stabilizing group can be added to a compound by reaction of a reactive group on the compound with a complementary reactive group on the stabilizing group. Complementary reactive groups are groups that react with one another, under appropriate conditions to form a new covalent bond. For example, an amine and an activated carbonyl group are complementary reactive groups that can react to form an amide bond. Preferably, the reaction that introduces the stabilizing group occurs under mild conditions that do not alter the structure of the compound. Protecting groups can be used in situations where reaction conditions would otherwise alter the compound. Compounds described in U.S. Pat. No. 6,630,503, (which is incorporated by reference in its entirety) can be modified with a stabilizing group. The synthetic methods described in U.S. Pat. No. 6,630,503 can be used to make a compound including a reactive group that can serve as a site of attachment for the stabilizing group.

The stabilizing group can be a water-soluble polymer. The water soluble polymer can be a polyether, such as, for example, a poly(ethylene glycol) (PEG) or a poly(propylene glycol) (PPG). The polyether can be terminated with a reactive functional group, such as a hydroxy group, or a non-reactive group, such as an alkyl or aryl group. A water soluble polymer can include a reactive functional group to facilitate its attachment to a compound.

Reactive PEGs can include different reactive groups. The reactive groups can react with a nucleophile. Nucleophiles can include an amine and a thiol. Nucleophilic reactive groups include, for example, amine-reactive aldehydes, activated esters or carbonates, such as an N-hydroxysuccinimide ester or a benzotriazole carbonate. Thiol-reactive groups include maleimides, pyridyl thioesters, and vinyl sulfones. Alternatively, the PEG can include a nucleophilic reactive group, such as an amine. A PEG with a nucleophilic reactive group can react with a compound having a complementary reactive group.

PEG polymers of different molecular weights can be prepared or purchased commercially. The number average molecular weight of a PEG can be, for example, less than 500, less than 10,000, less than 20,000, less than 30,000, less than 50,000, or higher. The greater number of ethylene glycol repeats in a PEG, the greater its molecular weight. Attaching a PEG to a compound can make the compound more water soluble.

Once synthesized, the activities and VLA-4 specificities of the compounds may be determined using in vitro and in vivo assays.

For example, the cell adhesion inhibitory activity of these compounds may be measured by determining the concentration of inhibitor required to block the binding of VLA-4-expressing cells to CS1 containing fibronectin- or CS1-coated plates. In this assay, microtiter wells are coated with either fibronectin (containing the CS1 sequence) or the CS1 peptide. If the CS1 peptide is used, it can be conjugated to a carrier protein, such as bovine serum albumin, in order to bind to the wells. Once the wells are coated, varying concentrations of the test compound are then added together with appropriately labeled, VLA-4-expressing cells. Alternatively, the test compound may be added first and allowed to incubate with the coated wells prior to the addition of the cells. The cells are allowed to incubate in the wells for at least 30 minutes. Following incubation, the wells are emptied and washed. Inhibition of binding is measured by quantitating the fluorescence or radioactivity bound to the plate for each of the various concentrations of test compound, as well as for controls containing no test compound.

VLA-4-expressing cells that may be utilized in this assay include Ramos cells, Jurkat cells, A375 melanoma cells, K562 cells transfected with integrin α4 gene, as well as mammalian (e.g., mouse, rat or human) peripheral blood lymophocytes (PBLs). The cells used in this assay may be fluorescently or radioactively labeled.

A direct binding assay may also be employed to quantitate the inhibitory activity of the compounds. In this assay, a VCAM-IgG fusion protein containing the first two immunoglobulin domains of VCAM (D1D2) attached above the hinge region of an IgG1 molecule ("VCAM 2D-IgG"), is conjugated to a marker enzyme, such as alkaline phosphatase ("AP"). The synthesis of this VCAM-IgG fusion is described in PCT publication WO 90/13300, which is incorporated by reference in its entirety. The conjugation of that fusion to a marker enzyme is achieved by cross-linking methods well-known in the art.

The VCAM-IgG enzyme conjugate is then placed in the wells of a multi-well filtration plate, such as that contained in the Millipore Multiscreen Assay System (Millipore Corp., Bedford, Mass.). Varying concentrations of the test inhibitory compound are then added to the wells followed by addition of VLA-4-expressing cells. The cells, compound and VCAM-IgG enzyme conjugate are mixed together and allowed to incubate at room temperature. Following incubation, the wells are vacuum drained, leaving behind the cells and any bound VCAM. Quantitation of bound VCAM is determined by adding an appropriate calorimetric substrate for the enzyme conjugated to VCAM-IgG and determining the amount of reaction product. Decreased reaction product indicates increased binding inhibitory activity.

Potency also can be measured on Jurkat cells using a radiolabeled ligand as a competitor. See Chen, L. L., et al. (2001) *J. Biol. Chem.* 276:36520–36529. Using the radiolabeled ligand, the potency can be assessed using a thermodynamic or a kinetic binding assay.

In order to assess the VLA-4 inhibitory specificity of the compounds, assays for other major groups of integrins, i.e., β2 and β3, as well as other β1 integrins, such as VLA-5, VLA-6 and α4β7 can be performed. These assays may be similar to the adhesion inhibition and direct binding assays described above, substituting the appropriate integrin-expressing cell and corresponding ligand. For example, polymorphonuclear cells (PMNs) express β2 integrins on their surface and bind to ICAM. β3 integrins are involved in platelet aggregation and inhibition may be measured in a standard platelet aggregation assay. VLA-5 binds specifically to Arg-Gly-Asp sequences, while VLA-6 binds to laminin. α4β7 is a homologue of VLA-4, which also binds fibronectin and VCAM. Specificity with respect to α4β7 is determined in a binding assay that utilizes the above-described VCAM-IgG-enzyme marker conjugate and a cell line that expresses α4β7, but not VLA-4, such as RPMI-8866 cells.

Once VLA-4-specific inhibitors are identified, they may be further characterized in in vivo assays. One such assay tests the inhibition of contact hypersensitivity in an animal, such as described by P. L. Chisholm et al., "Monoclonal Antibodies to the Integrin α-4 Subunit Inhibit the Murine Contact Hypersensitivity Response", *Eur. J. Immunol.*, 23, pp. 682–688 (1993) and in "Current Protocols in Immunology", J. E. Coligan, et al., Eds., John Wiley & Sons, New York, 1, pp. 4.2.1–4.2.5 (1991), each of which is incorporated by reference in its entirety. In this assay, the skin of the animal is sensitized by exposure to an irritant, such as dinitrofluorobenzene, followed by light physical irritation, such as scratching the skin lightly with a sharp edge. Following a recovery period, the animals are re-sensitized following the same procedure. Several days after sensitization, one ear of the animal is exposed to the chemical irritant, while the other ear is treated with a non-irritant control solution. Shortly after treating the ears, the animals are given various doses of the VLA-4 inhibitor by subcutaneous injection. In vivo inhibition of cell adhesion-associated inflammation is assessed by measuring the ear swelling response of the animal in the treated versus untreated ear.

Swelling is measured using calipers or other suitable instrument to measure ear thickness. In this manner, one may identify those inhibitors that are best suited for inhibiting inflammation.

Another in vivo assay that may be employed to test the compounds is the sheep asthma assay. This assay is performed essentially as described in W. M. Abraham et al., "α-Integrins Mediate Antigen-induced Late Bronchial Responses and Prolonged Airway Hyperresponsiveness in Sheep", *J. Clin. Invest.*, 93, pp. 776–87 (1994), which is herein incorporated by reference in its entirety. This assay measures inhibition of *Ascaris* antigen-induced late phase airway responses and airway hyperresponsiveness in asthmatic sheep.

Yet another in vivo test is EAE, an animal model of multiple sclerosis. This assay is performed essentially as previously described (Leone, D. R., et al. (2003) *J. Pharmacol. Exp. Ther.* 305:1150–1162) and measures disease progress that is the result of mounting an immune response to myelin basic protein. A rat is immunized with an emulsion of Guinea pig Mylein Basic Protein (MBP) peptide in complete Freund's adjuvant. Test compounds or control compounds can be administered (for example, by s.c. or i.v. injection), and the animal is then observed for signs of paralysis starting on day 7 post immunization and daily thereafter.

The compounds may be formulated into pharmaceutical compositions that may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques.

The pharmaceutical compositions can include any of the compounds, or pharmaceutically acceptable derivatives thereof, together with any pharmaceutically acceptable carrier. The term "carrier" as used herein includes acceptable adjuvants and vehicles. Pharmaceutically acceptable carriers that may be used in the pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The pharmaceutical compositions may be in the form of a sterile injectable preparation, for example a sterile injectable aqueous or oleaginous suspension. This suspension may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as do natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol. A compound including a PEG moiety can be soluble in water or an isotonic saline solution.

The pharmaceutical compositions can be administered parenterally by injection. In particular, if the composition includes a compound having a PEG moiety, a parenteral administration may be preferred. Suitable formulations for parenteral administration include aqueous solutions of the active compounds in water-soluble form, e.g., water-soluble salts. These aqueous formulations may contain inert ingredients such as water, ethyl alcohol, ethyl carbonate, ethyl acetate, benzyl alcohol, benzyl benzoate, propylene glycol, 1,3-butylene glycol, dimethylformamide, oils, glycerol, tetrahydrofurfuryl alcohol, polyethylene glycols, and fatty acid esters of sorbitan. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances that increase the viscosity of the suspension, for example, sodium carboxymethyl cellulose, sorbitol and dextran. Optionally, the suspension may also contain stabilizers. Liposomes also can be used to encapsulate the active compounds for delivery into cells or interstitial spaces. Exemplary pharmaceutically acceptable carriers are physiologically compatible solvents, dispersion media, coatings, antibacterial and antifungal agents, isotonic and absorption delaying agents, water, saline, phosphate buffered saline, dextrose, glycerol, ethanol and the like. In some embodiments, the composition comprises isotonic agents, for example, sugars, polyalcohols such as mannitol, sorbitol, or sodium chloride. In some embodiments, the compositions include pharmaceutically acceptable substances such as wetting or emulsifying agents, preservatives or buffers.

In addition to parenteral administration, other routes of administration, such as nasal or suppository, may be preferred for the treatment of a selective disease such as asthma or a bowel disease.

The pharmaceutical compositions may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

The active ingredient can also be formulated with a controlled-release formulation or device. Examples of such formulations and devices include implants, transdermal patches, and microencapsulated delivery systems. Biodegradable, biocompatible polymers can be used, for example, ethylene vinyl acetate, polyanhydrides, polyglycolic acid, collagen, polyorthoesters, and polylactic acid. Methods for the preparation of such formulations and devices are known in the art. See e.g., Sustained and Controlled Release Drug Delivery Systems, J. R. Robinson, ed., Marcel Dekker, Inc., New York, 1978.

Injectable depot formulations can be made by forming microencapsulated matrices of the drug in biodegradable polymers such as polylactide-polyglycolide. Depending on the ratio of drug to polymer, and the nature of the polymer employed, the rate of drug release can be controlled. Other exemplary biodegradable polymers are polyorthoesters and polyanhydrides. Depot injectable formulations also can be prepared by entrapping the drug in liposomes or microemulsions.

Alternatively, the pharmaceutical compositions may be administered in the form of suppositories for rectal administration. These can be prepared by mixing the agent with a suitable non-irritating excipient which is solid at room temperature but liquid at the rectal temperature and therefore will melt in the rectum to release the drug. Such materials include cocoa butter, beeswax and polyethylene glycols.

The pharmaceutical compositions may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions may also be administered by nasal aerosol or inhalation through the use of a nebulizer, a dry powder inhaler or a metered dose inhaler. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of active ingredient that may be combined with the carrier materials to produce a single dosage form will vary depending upon the host treated, and the particular mode of administration. It should be understood, however, that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of active ingredient may also depend upon the therapeutic or prophylactic agent, if any, with which the ingredient is co-administered.

An effective amount of a pharmaceutical composition is the amount which is required to confer a therapeutic effect on the treated patient, and will depend on a variety of factors, such as the nature of the inhibitor, the size of the patient, the goal of the treatment, the nature of the pathology to be treated, the specific pharmaceutical composition used, and the judgment of the treating physician. For reference, see Freireich et al., *Cancer Chemother. Rep.* 1966, 50, 219 and Scientific Tables, Geigy Pharmaceuticals, Ardsley, N.Y., 1970, 537. Dosage levels of between about 0.001 and about 1000 mg/kg body weight per day, such as between about 0.1 and about 100 mg/kg body weight per day, or between about 0.1 and about 10 mg/kg body weight per day of the active ingredient compound are useful.

Compositions containing a compound can also include an additional agent selected from the group consisting of corticosteroids, bronchodilators, antiasthmatics (mast cell stabilizers), antiinflammatories, antirheumatics, immunosuppressants, antimetabolites, immunonodulators, antipsoriatics and antidiabetics. Specific compounds within each of these classes may be selected from any of those listed under the appropriate group headings in "Comprehensive Medicinal Chemistry", Pergamon Press, Oxford, England, pp. 970–986 (1990), which is incorporated by reference in its entirety. Also included within this group are compounds such as theophylline, sulfasalazine and aminosalicylates (antiinflammatories); cyclosporin, FK-506, and rapamycin (immunosuppressants); cyclophosphamide and methotrexate (antimetabolites); and interferons (immunomodulators).

The compounds, or pharmaceutical formulations including the compounds, can be used in methods for preventing, inhibiting or suppressing cell adhesion-associated inflammation and cell adhesion-associated immune or autoimmune responses. VLA4-associated cell adhesion plays a central role in a variety of inflammation, immune and autoimmune diseases. Thus, inhibition of cell adhesion by the compounds may be utilized in methods of treating or preventing inflammatory, immune and autoimmune diseases. Preferably the diseases to be treated with the methods are selected from asthma, arthritis, psoriasis, transplantation rejection, multiple sclerosis, diabetes and inflammatory bowel disease.

These methods may employ the compounds in a monotherapy or in combination with an anti-inflammatory or immunosuppressive agent. Such combination therapies include administration of the agents in a single dosage form or in multiple dosage forms administered at the same time or at different times.

Methods for preparing precursors of the compounds are described below, and in U.S. Pat. No. 6,630,503. In general, the precursor are inhibitors that have a reactive group suitable for the attachment of a water soluble polymer, for example, a PEG moiety. The reactive group can be a nucleophilic group such as an amine, and the PEG moiety can include an electrophilic group, such as an activated ester or a vinyl sulfone. A succinimidyl ester is one example of an activated ester. The inhibitor can include a linker group to which the PEG moiety is attached. The PEG moiety can include reactive groups at one or more ends. In one example, a PEG moiety has one end including a reactive succinimidyl ester, and another end including a non-reactive methyl group. The precursors can be PEGylated by reaction with an appropriate PEGylating reagent.

EXAMPLES

Synthesis of Compounds

One general method of making cell adhesion inhibitors is described below. Other general methods can be found, for example, in U.S. Pat. No. 6,630,503, which is incorporated by reference in its entirety.

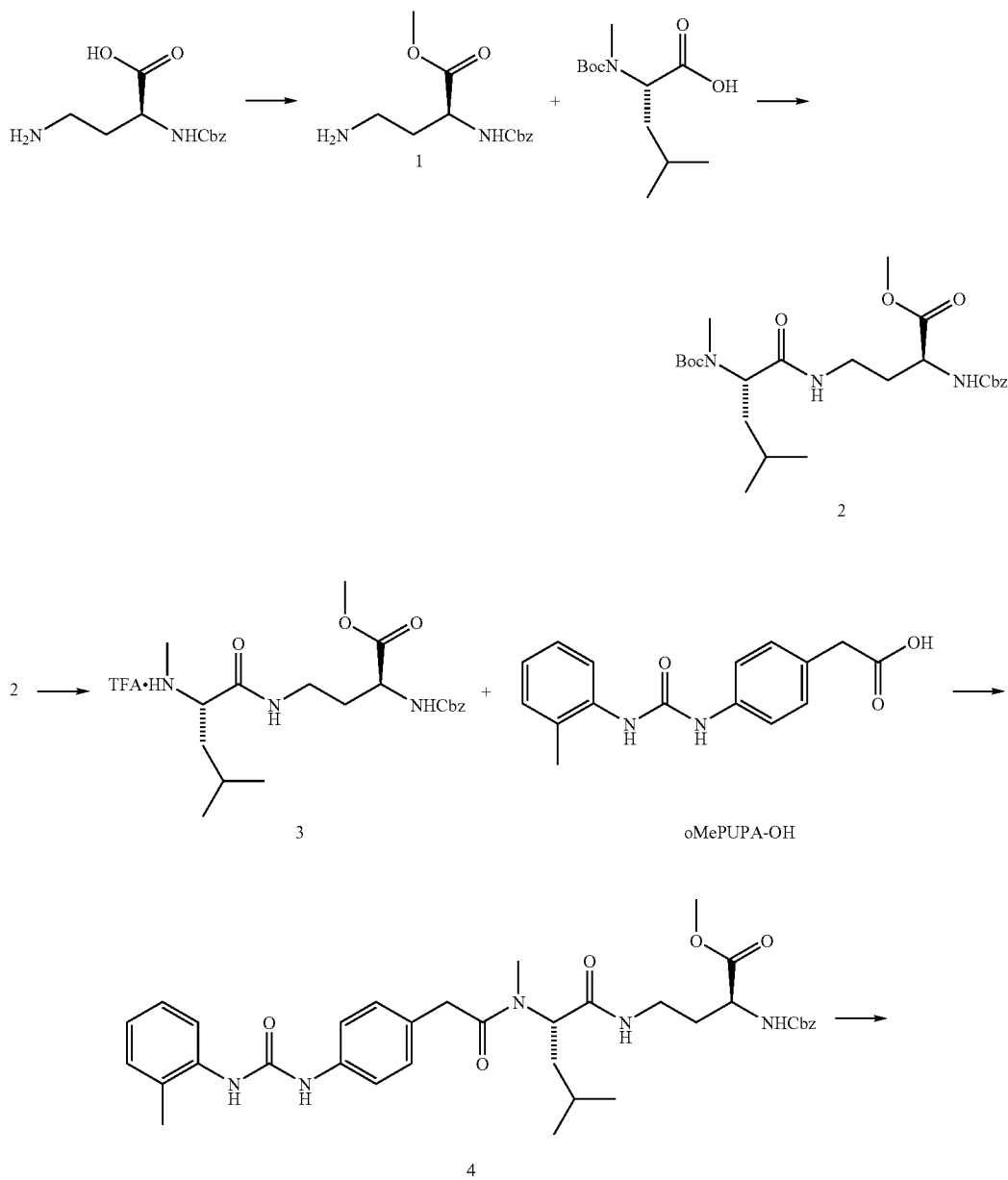

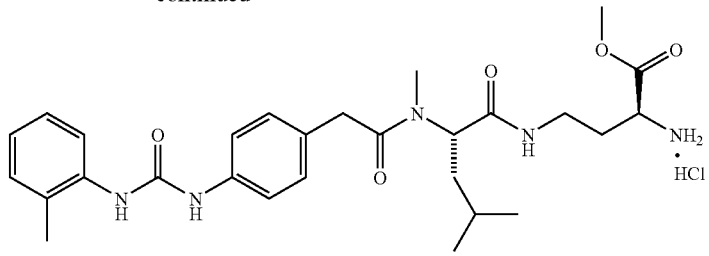

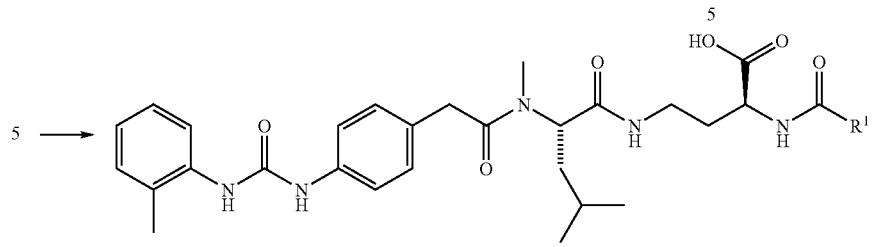

N-α-CBZ-L-2,4-diaminobutyric acid methyl ester hydrochloride (1): In a 500 mL round bottom flask 8.4 g (33.3 mmol) of N-α-CBZ-L-2,4-diaminobutyric acid was suspended in 200 mL methanol with stirring. This was cooled to 0° C. (ice bath), and then 14.6 mL (200 mmol) $SOCl_2$ was added dropwise over 15 minutes to give a colorless solution. The solution was allowed to warm to room temperature and stirred overnight. The solution was concentrated, redissolved in methanol and concentrated twice, then dissolved in $CH_2Cl_2$, concentrated, and placed under high vacuum for 16 hours to give 10.33 g (34.2 mmol, 103%) of compound 1 as a slightly yellow foam. M/z=267.1 (M+H$^+$).

BOC-N-methyl-Leucinyl-(N-α-CBZ)-GABA methyl ester (2): In a 500 mL round bottom flask was dissolved 10.33 g (33.3 mmol) of 1 (MW=302) in 100 mL dry dimethylformamide (DMF) with stirring to give a colorless solution. To this was added 17.4 mL (100 mmol) of diisopropylethylamine (DIEA), then 7.96 g (32.5 mmol) of Boc-N-Me-Leucine, and finally 14.83 g (39.0 mmol) of O-(7-azabenzotriazol-1-yl)-1,1,3,3-tetramethyluronium hexafluorophosphate (HATU) to give a yellow solution. This was stirred overnight, after which HPLC showed no starting material. The solution was diluted with ethyl acetate (EtOAc, 500 mL) and washed with 1N HCl (twice), 1N NaOH (twice), and brine (once). The organic phase was dried over anhydrous $MgSO_4$, filtered, and concentrated to a red oil. Chromatography with 2:1 hexanes/EtOAc vs. silica gave 12.56 g (25.5 mmol, 78%) of 2 ($R_f$=0.46 with 1:1 Hex/EtOAc vs. silica) as a yellow syrup (HPLC, >99%). M/z=494.3 (M+H$^+$).

H—N-methyl-Leucinyl-(N-α-CBZ)-GABA methyl ester trifluoroacetate salt (3): In a 50 mL round bottom flask was dissolved 0.50 g (1.01 mmol) of 2 (MW=493) in 10 mL $CH_2Cl_2$ with stirring to give a colorless solution. To this was added 2 mL (26 mmol, large excess) of trifluoroacetic acid and the resulting solution was stirred for four hours, after which HPLC showed no starting material. The solution was concentrated, redissolved in $CH_2Cl_2$ and concentrated (twice), then placed under high vacuum overnight to give 0.52 g (~quantitative) of 3 as a very pale yellow oil. M/z=394.4 (M+H$^+$). Material carried through.

oMePUPA-N-methyl-Leucinyl-(N-α-CBZ)-GABA methyl ester (4): In a 10 mL vial was dissolved 0.52 g (1.01 mmol) of 3 (MW=507) in 5 mL DMF with stirring to give a pale yellow solution. To this was added 525 μL (3.0 mmol) of DIEA, then 284 mg (1.0 mmol) of oMePUPA-OH (Ricerca; MW=284; see also below), and finally 0.42 g (1.1 mmol) of HATU to give a yellow solution. This was stirred overnight, after which HPLC showed no starting material remaining. The solution was diluted with EtOAc (75 mL) and washed with 1N HCl (three times), 1N NaOH (three times), and brine (once). The organic phase was dried with $MgSO_4$, filtered, and the filtrate concentrated to a yellow oil/solid mixture. Chromatography with 1:2 acetonitrile/$CH_2Cl_2$ vs. silica gave 0.49 g (0.74 mmol, 74%) of 4 ($R_f$=0.56 with 1:1 acetonitrile/$CH_2Cl_2$ vs. silica) as a bright white, foamy solid (HPLC, >99%). M/z=660.1 (M+H$^+$).

oMePUPA-N-methyl-Leucinyl-(N-α-H)-GABA methyl ester Hydrochloride (5): In an 85 mL high-pressure vessel was dissolved 400 mg (0.61 mmol) of 4 (MW=659) in 10 mL methanol with stirring to give a colorless solution. The vessel was flushed with nitrogen, and ~50 mg (catalytic) of 10% palladium on carbon was added. The sides of the vessel were washed with additional methanol, and the vessel capped with a hydrogenation head. The vessel was charged with 60 psi $H_2$ and the mixture stirred overnight, after which the vessel was purged to ambient atmosphere. The mixture was filtered through Celite 545, the filter pad washed with additional (10 mL) methanol, and the filtrate concentrated. The residue was dissolved in minimal (2 mL) methanol and dripped into ice-cold 1.0 M HCl in diethyl ether to give a white precipitate. The solid was triturated in the HCl/ether for 20 minutes, then filtered, the solid washed with ether, and air-dried for one hour. The white solid was then crushed into a powder with a spatula, washed with additional ether, and air-dried overnight to give 336 mg (0.60 mmol, 98%) of 5 as a white powder (HPLC, >99%). ESMS m/z=526.6 (M+H$^+$).

Acylation and final hydrolysis: Crude amine 5 was dissolved in N,N-dimethylformamide along with R¹CO₂H (1 equivalent) and HBTU (1.1 equivalent). With stirring was added N,N-diisopropylethylamine (4 equivalents). After stirring overnight, the reaction was partitioned between 5% aqueous citric acid and ethyl acetate. The organic layer was washed with saturated sodium chloride solution, then dried over sodium sulfate. Filtration of the drying agent and evaporation of the solvent gave crude amide, which could be purified by reverse-phase HPLC. Methyl ester was dissolved in 1:1 tetrahydrofuran and methanol. With stirring was added aqueous lithium hydroxide (2 N). After stirring for one hour, the reaction mixture was concentrated to dryness. The residue was partitioned between 1 N aqueous hydrogen chloride and ethyl acetate, and the organic layer was washed with saturated sodium chloride. Drying over sodium sulfate, filtering and evaporating gave crude acid. Purification by preparative reverse-phase high performance liquid chromatography gave pure product.

4-(2-methylphenylaminocarbonylamino)phenylacetic Acid (oMePUPA-OH): To a suspension of p-aminophenylacetic acid (56.8 g, 376 mmol) in DMS (150 mL) was added o-tolyl isocyanate (50 g, 376 mmol) dropwise. The reaction mixture was allowed to stir 1 hour, and was poured into EtOAc (1.75 L) with stirring. The precipitate was collected and washed with EtOAc (400 mL) and MeCN (400 mL) to provide oMePUPA (80 g, 75%). ESMS m/z (M+H⁺) 285.1.

oMePUPA-Leu-OH: oMePUPA-OH (0.78 g) was combined with leucine methyl ester hydrochloride (0.50 g, 1.0 eq), HATU (1.10 g, 1.05 eq), and diisopropylethylamine (1.9 mL, 4 eq) in 10 mL dry DMF. The reaction was stirred for 16 hours at room temperature after which it was diluted with 50 mL EtOAc, which was washed with 5% citric acid, water, saturated sodium bicarbonate and brine. The resulting organic solution was dried over sodium sulfate filtered and concentrated to yield 1.13 g of white solid. This product was dissolved in 10 mL THF. 5 mL 2N LiOH was added and the reaction was stirred for 16 h. THF was removed under reduced pressure and the solution was diluted with 40 mL water and washed with EtOAc. The aqueous layer was acidified with 1N HCl and was extracted with EtOAc. The organic extracts were washed with dilute HCl and brine, were dried over sodium sulfate, filtered and concentrated under reduced pressure yielding 0.77 g of white solid. ESMS m/z (M+H⁺) 398.5.

N-(3,5-dichlorobenzenesulfonyl)-Proline Methyl Ester: To a solution of 24.8 g (0.15 mol) of L-Proline methyl ester hydrochloride in 500 mL of CH₂Cl₂ was added 70 mL (0.5 mol) of triethylamine with stirring to give copious white precipitate. The mixture was filtered, and the filtrate cooled to 0° C. (ice bath) with stirring. To the cooled solution was added a solution of 36.8 g (0.15 mol) of 3,5-dichlorobenzenesulfonyl chloride in 70 mL of CH₂Cl₂ dropwise quickly over five minutes. The addition funnel was rinsed with an additional 30 mL of CH₂Cl₂, and the cloudy yellow mixture was allowed to warm to room temperature with stirring overnight. The mixture was washed twice with 400 mL of 1 N HCl, twice with 400 mL of 1 N NaOH, then brine, then dried (MgSO₄), filtered, and concentrated to a yellow oil which crystallized on standing. The material was recrystallized three times from ethyl acetate/hexanes to give 39.3 g (0.116 mol, 77%) of N-(3,5-dichlorobenzenesulfonyl)-Proline methyl ester (MW=338) as white needles (TLC on silica vs. 2:1 hexanes/ethyl acetate, R_f=0.51). M/z=339.3 (M+H⁺).

N-(3,5-dichlorobenzenesulfonyl)-Proline: To a solution of 39.3 g (0.116 mol) of the above methyl ester in 250 mL methanol was added 115 mL (0.23 mol) of freshly-prepared 2 M aqueous LiOH with stirring to give a colorless solution. This was stirred for three hours, after which HPLC showed no starting material. The solution was reduced by 50% in vacuo and partitioned between 1 N HCl and CH₂Cl₂ (~200 mL each). The phases were separated and the aqueous layer was washed again with CH₂Cl₂. The organic phases were combined, dried (MgSO₄), and concentrated to a white, foamy solid. This was recrystallized twice from ethyl acetate/hexanes to give 33.8 g (0.104 mol, 90%) of the title compound as colorless, broad, flat needles. M/z=325.2 (M+H⁺).

Compound A Synthesis

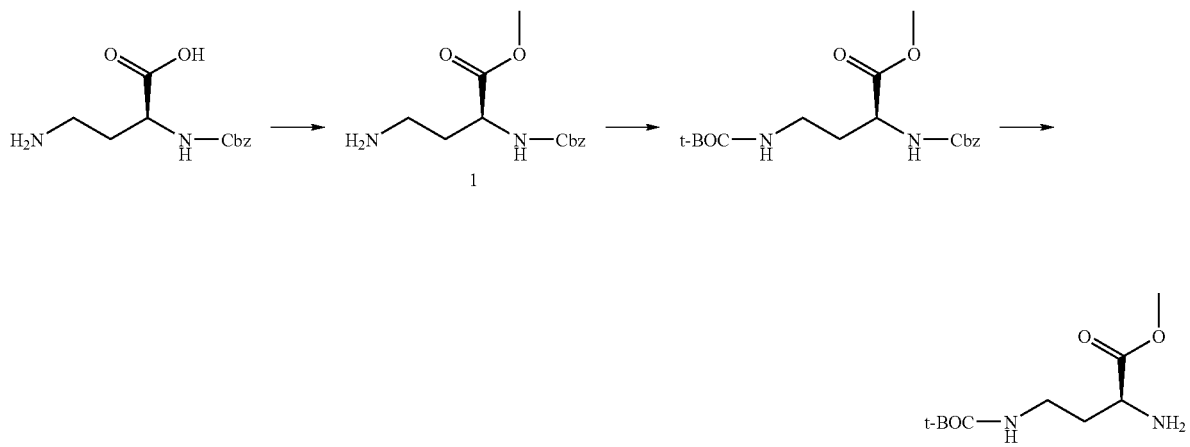

-continued
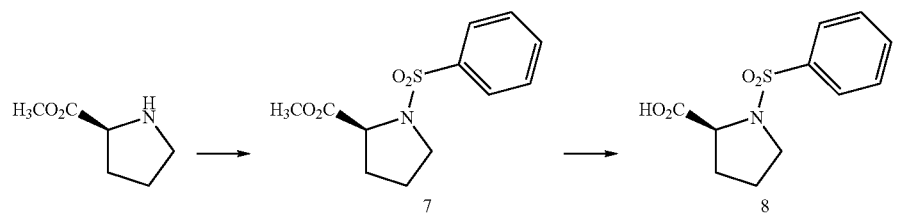
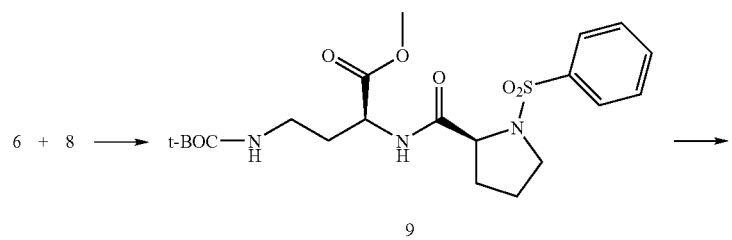
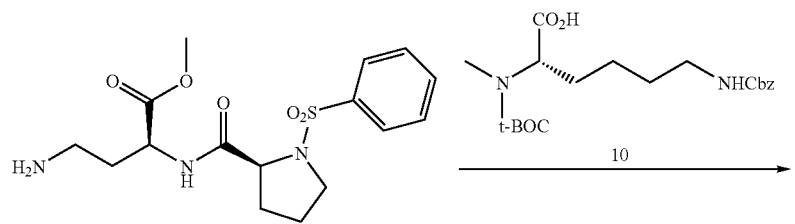
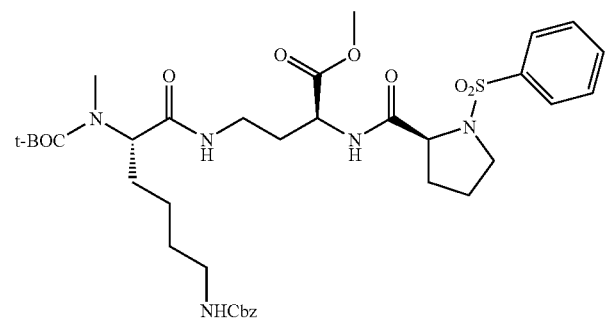
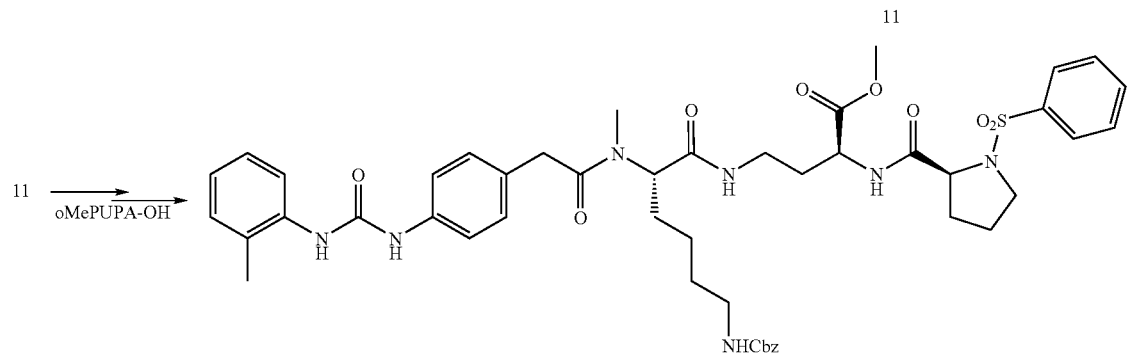

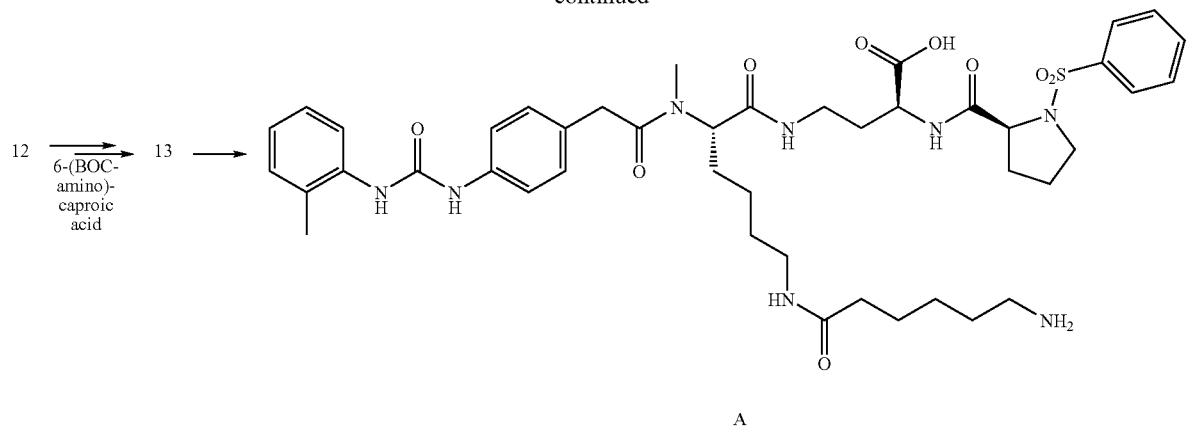

14.6 mL (200 mmol) of SOCl₂ was added dropwise over a period of 15 minutes to a suspension of 8.4 g (33.3 mmol) Nα-CBZ-L-2,4-diaminobutyric acid in 200 mL of methanol at 0° C. and stirred overnight at 23° C. The solution was concentrated and redissolved in methanol 3 times, then dissolved in CH₂Cl₂, concentrated, and placed under high vacuum to give 10.33 g of the methyl ester 1. The crude ester was dissolved in 200 mL CH₂Cl₂ and 16.2 mL (116.6 mmol) triethylamine was added followed by 8.96 g (41 mmol) di-tert-butyl dicarbonate. After stirring at 23° C. for 4 hours, the solution was washed once with 1 N HCl, once with saturated NaHCO₃ solution, and once with saturated NaCl, then dried (Na₂SO₄), filtered and concentrated to give a yellow syrup. Purification by flash column chromatography gave 9.6 g (26.3 mmol, 79%) of the t-butoxycarbonyl (BOC) protected amine as a colorless syrup. The solution of this BOC protected amine in 100 mL of methanol was stirred overnight under 60 psi of H₂. The mixture was filtered through a plug of Celite and concentrated. 6.0 g (26 mmol, 78% yield) of compound 6 (Nγ-Boc-L-2,4-diaminobutyric acid methyl ester) as a colorless oil was recovered, which was used without further purification. MS: m/z 232 (M+H⁺).

N-(benzenesulfonyl)-Proline Methyl Ester (7): To a solution of 25 g (0.15 mol) of L-Proline methyl ester hydrochloride in 500 mL of CH₂Cl₂ was added 70 mL (0.5 mol) of triethylamine with stirring to give copious white precipitate. The mixture was filtered and the filtrate cooled to 0° C. (ice bath) with stirring. To the cooled solution was added a solution of 20 mL (0.15 mol) of benzenesulfonyl chloride in 50 mL of CH₂Cl₂ dropwise over fifteen minutes. The addition funnel was rinsed with an additional 25 mL of CH₂Cl₂, and the cloudy, colorless mixture was allowed to warm to room temperature with stirring overnight. The solution was washed twice with 400 mL of 1 N HCl, twice with 400 mL of 1 N NaOH, once with brine, then dried (MgSO₄), filtered, and concentrated to a pale yellow solid. This material was recrystallized three times from ethyl acetate/hexanes to give 38.2 g (0.142 mol, 95%) of N-(benzenesulfonyl)-Proline methyl ester 7 (MW=269) as broad white needles (TLC vs. 2:1 hexanes/ethyl acetate, $R_f$=0.35). M/z=270.2 (M+H⁺).

N-(benzenesulfonyl)-Proline (8): To a solution of 38.2 g (0.142 mol) of the above methyl ester 7 in 500 mL methanol was added 140 mL (0.28 mol) of freshly-prepared 2 M aqueous LiOH with stirring to give a colorless solution. This was stirred overnight, after which HPLC showed no starting material. The solution was reduced by 50% in vacuo and partitioned between 1 N HCl and CH₂Cl₂ (~200 mL each). The phases were separated and the aqueous layer was washed again with CH₂Cl₂. The organic phases were combined, dried (MgSO₄), and concentrated to a white solid. This was recrystallized twice from ethyl acetate/hexanes to give 34.7 g (0.136 mol, 96%) of 8 as fine white needles. M/z=256.2 (M+H⁺).

To a solution of 62 mg (0.27 mmol) of compound 6 and 77 mg (0.30 mmol) of compound 8 in 3 mL of dimethyl formamide (DMF) was added 137 mg (0.36 mmol) of O-(7-Azabenzotriazol-1-yl)-N,N,N',N'-tetramethyluronium hexafluorophosphate (HATU), followed by 175 μL (1.0 mmol) of diisopropylethylamine to give a yellow solution. After stirring at 23° C. for 2 hours, the solution was diluted with ethyl acetate, washed with 1 N HCl, then with 1 N NaOH, followed by a wash with saturated NaCl, and dried using Na₂SO₄. The filtered solution was concentrated by vacuum to give 128 mg of compound 9 (2(S)-{[1-benzenesulfonyl-pyrrolidine-2(S)-carbonyl]-amino-4-tertbutoxycarbonylamino-butyric acid methyl ester) as a yellow oil, which was used without further purification. MS: m/z 470 (M+H⁺), 370 (M–BOC+H⁺). 75 mg (0.16 mmol) of compound 9 was dissolved in 3 mL CH₂Cl₂ and 1 mL of trifluoroacetic acid was added. After stirring for 2 hours at 23° C., the solution was concentrated in CH₂Cl₂ 3 times, and then dissolved in 2 mL of DMF. 56 mg (0.14 mmol) of amino acid 10 (Boc-N-Me-Lys(Z)-OH.DCHA (BACHEM, cat# A-3690)), 64 mg (0.17 mmol) of HATU, and 175 μL (1.0 mmol) of diisopropylethylamine were added to give a yellow solution. This mixture was stirred for 4 hours at 23° C., then diluted with ethyl acetate, washed with 1 N HCl, 1 N NaOH, then with saturated NaCl and dried (Na₂SO₄). The filtered solution was concentrated by vacuum to give 100 mg (0.13 mmol, 96%) of compound 11 (2(S)-{[1-Benzenesulfonyl-pyrrolidine-2(S)-carbonyl]-amino}-4-[6-benzyloxycarbonylamino-2(S)-(tert-butoxycarbonyl-methyl-amino)-hexanoylamino]-butyric acid methyl ester) as a yellow oil, which was used without further purification. MS: m/z 746

(M+H⁺), 646 (M–BOC+H⁺). 100 mg (0.13 mmol) of compound 11 was dissolved in 3 mL of CH₂Cl₂, a 1 mL aliquot of trifluoroacetic acid was added with stirring. After 2 hours, the solution was redissolved in CH₂Cl₂ and concentrated 3 times, then dissolved in 3 mL of DMF. 43 mg (0.15 mmol) of o-Methyl tolyl-ureido-phenyl-acetic acid oMePUPA-OH, 64 mg (0.17 mmol) of HATU, and 175 µL (1.0 mmol) of diisopropylethylamine were added to give a yellow solution. After stirring at 23° C. for 4 hours, the solution was diluted with ethyl acetate and processed as described above for compound 11 to give a yellow foamy solid. Chromatography in (2:1 CH₂Cl₂/acetonitrile, then 1:1 CH₂Cl₂/acetonitrile, then 5% methanol in CH₂Cl₂ vs. SiO₂) was performed to give 83 mg (0.09 mmol, 65%) of compound 12 (2(S)-[(1-Benzenesulfonyl-pyrrolidine-2(S)-carbonyl)-amino]-4-[6-benzyloxycarbonylamino-2(S)-(methyl-{2-[4-(3-o-tolyl-ureido)-phenyl]-acetyl}-amino)-hexanoylamino]-butyric acid methyl ester) as a foamy, white solid (R$_f$=0.17 in 1:1 CH₂Cl₂/acetonitrile). MS: m/z 912 (M+H⁺). 83 mg (0.09 mmol) of compound 12 was hydrogenated as above for compound 16. Filtration through Celite and vacuum concentration gave a white, foamy solid. The solid was dissolved in 2 mL of DMF, and then 21 mg (0.09 mmol) of 6-(BOC-amino)caproic acid, 41 mg (0.11 mmol) of HATU, and 175 µL (1.0 mmol) of diisopropylethylamine were added. After stirring for 2 hours at 23° C., the solution was diluted with ethyl acetate and processed as for compound 11. 52 mg (0.05 mmol, 60%) of compound 13 (2(S)-[(1-Benzenesulfonyl-pyrrolidine-2(S)-carbonyl)-amino]-4-[6-(6-tert-butoxycarbonylamino-hexanoylamino)-2(S)-(methyl-{2-[4-(3-o-tolyl-ureido)-phenyl]-acetyl}-amino)-hexanoylamino]-butyric acid methyl ester) was recovered as a yellow solid that was used without further purification. MS: m/z 991 (M+H⁺), 891 (M–BOC+H⁺).

To a solution of 52 mg (0.05 mmol) of compound 13 in 3 mL of methanol, 265/L (0.53 mmol) of 2 N LiOH was added while stirring. After 2 hours, the solution was redissolved in acetone and concentrated. The residue was dissolved in 2 mL CH₂Cl₂. 2 mL of trifluoroacetic acid was added. The sample was stirred for 90 minutes at 23° C., and then concentrated. The residue was dissolved in minimal methanol and purified by reverse-phase high pressure liquid chromatography (5 to 95% acetonitrile in water with 0.1% trifluoroacetic acid) to give 26 mg (0.026 mmol, 50%) of compound A (4-[6-(6-Amino-hexanoylamino)-2(S)-(methyl-{2-[4-(3-o-tolyl-ureido)-phenyl]-acetyl}-amino)-hexanoylamino]-2(S)-[(1-benzenesulfonyl-pyrrolidine-2(S)-carbonyl)-amino]-butyric acid) as a white solid. MS: m/z 878 (M+H⁺).

Compound B (2S-[(1-benzenesulfonyl-pyrrolidine-2S-carbonyl)-amino]-4-[4-methyl-2S-(methyl-{2-[4-(3-o-tolyl-ureido)-phenyl]-acetyl}-amino)-pentanoylamino]-butyric acid), ³⁵S-B, and compounds C, D, E, and F (see Scheme 1 below) can be synthesized according to the method described above for compound A, except that Boc-N-methyl-leucine was used in place of amino acid 10. In the preparation of compounds C, D, E, and F, proline was replaced with anti-4-aminoproline (C), syn-4-(6-aminohexanoyl)aminoproline (D), anti-4-(6-aminohexanoyl)aminoproline (E), or with syn-4-aminoproline (F). See also Chen, L. L., et al. (2001) J. Biol. Chem. 276:36520–36529; Leone, D. R., et al. (2003) J. Pharmacol. Exp. Ther. 305: 1150–1162; and U.S. Pat. No. 6,630,503, each of which is incorporated by reference in its entirety.

Derivatives of 4-aminoproline can be prepared from 4-hydroxyproline or from 4-aminoproline.

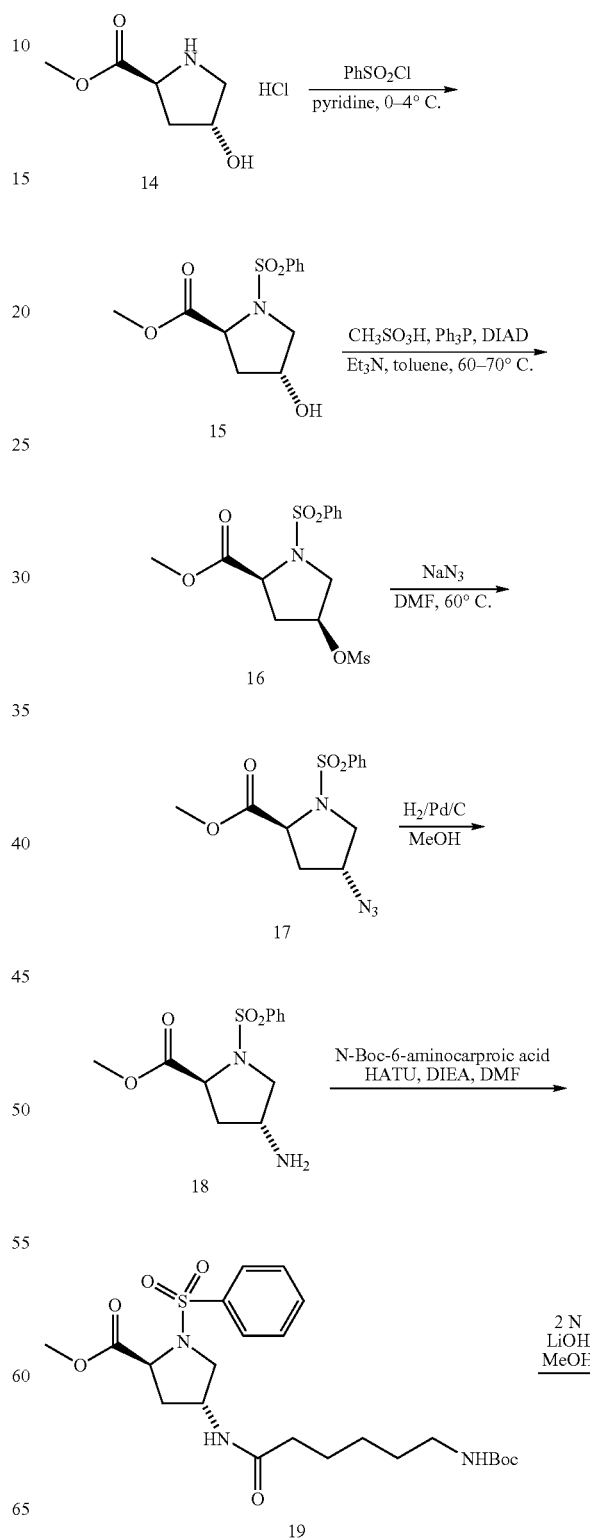

-continued

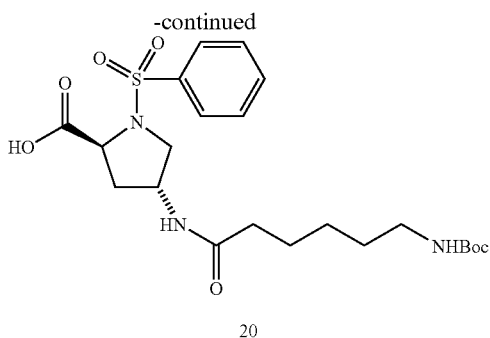

20

N-(benzenesulfonyl)-trans-4-hydroxyproline methyl ester (15): In a 250 mL round bottom flask was dissolved 10.0 g (55 mmol) of trans-4-hydroxyproline methyl ester hydrochloride 14 (Bachem) in 100 mL anhydrous pyridine at 0° C. with stirring to give a cloudy white mixture. To this was added 7.9 mL (62 mmol, 1.1 equiv.) of benzenesulfonyl chloride in four portions over 15 minutes to give a bright yellow mixture. This reaction mixture was stirred under a $CaCl_2$ drying tube at 4° C. (cold room) overnight, then concentrated in vacuo, and the residue dissolved in ethyl acetate (~200 mL.) The solution was washed with 1 N HCl (three times), with $H_2O$, 1 N NaOH (three times), then brine, and the organic solution was dried ($MgSO_4$), filtered, and concentrated to give a yellow oil. This was dissolved in ethyl acetate, loaded onto silica, and eluted with 3:2 ethyl acetate/hexanes to give 11.5 g (40.3 mmol, 73%) of compound 15 as a white crystalline solid. $^1$H-NMR (400 MHz, CDCl$_3$, δ ppm) 7.85 (dt, J=2 Hz, 7 Hz, 2H), 7.57 (tt, J=1 Hz, 8 Hz, 1H), 7.49 (td, J=2 Hz, 7 Hz, 2H), 4.41 (br s, 1H), 4.37 (t, J=8 Hz, 1H), 3.70 (s, 3H), 3.57 (dd, J=4 Hz, 11 Hz, 1H), 3.37 (dt, J=2 Hz, 11 Hz, 1H), 2.17 (m, 2H), 2.06 (m, 1H); $^{13}$C-NMR (400 MHz, CDCl$_3$, δ ppm) 173.01, 138.05, 133.43, 129.42, 128.05, 70.37, 59.85, 56.83, 52.99, 39.81; m/z: 286 (M+1)$^+$. See, for example, DiCesare, P., et al.; *J. Med. Chem.*; 35(22), pp. 4205–4213 (1992), which is incorporated by reference in its entirety.

N-(benzenesulfonyl)-cis-4-(methanesulfonyloxy)-proline, methyl ester (16): In a two-neck 50 mL flask was combined 0.55 mL (8.42 mmol, 1.2 equiv.) of methanesulfonic acid and 20 mL of anhydrous toluene under $N_2$ and a Dean-Stark trap. The solution was heated to reflux for 90 minutes, then cooled, and the trap removed. Triphenylphosphine (2.21 g, 8.42 mmol, 1.2 equiv.) was added with stirring, the solution was cooled to 0° C. (ice water bath), and 1.93 mL (9.83 mmol, 1.4 equiv.) of diisopropyl azidodicarboxylate was added slowly via syringe over 15 minutes. The bright yellow slurry was warmed to RT, compound 15 added (2.0 g, 7.02 mmol), then triethylamine (0.39 mL, 2.81 mmol, 0.4 equiv.), and the resulting yellow slurry was heated to ~70° C. for two hours. The mixture was then cooled to room temperature, diluted with ~25 mL EtOAc, and a white precipitate filtered off. The filtrate was concentrated, redissolved in EtOAc, loaded onto silica, and eluted with 2:1 EtOAc/hexanes to give 0.63 g (1.73 mmol, 59% yield based on 1.16 g of recovered starting material) of 16 as a colorless glass which crystallized on standing. $^1$H-NMR (400 MHz, CDCl$_3$, δ ppm) 7.89 (dt, J=2 Hz, 7 Hz, 2H), 7.60 (tt, J=1 Hz, 8 Hz, 1H), 7.53 (td, J=2 Hz, 7 Hz, 2H), 5.14 (m, 1H), 4.57 (dd, J=3 Hz, 10 Hz, 1H), 3.71 (m, 1H), 3.69 (s, 3H), 3.62 (dq, J=1 Hz, 12 Hz, 1H), 2.94 (s, 3H), 2.52 (dq, J=1 Hz, 15 Hz, 1H), 2.32 (m, 1H); $^{13}$C-NMR (400 MHz, CDCl$_3$, δ ppm) 171.47, 138.42, 133.67, 129.61, 127.94, 78.23, 59.33, 53.88, 53.07, 39.30, 37.41; m/z: 364 (M+1)$^+$. See, for example, Anderson, N. G., et al.; *J. Org. Chem.*; 61(22), pp. 7955–7958 (1996), which is incorporated by reference in its entirety.

N-(benzenesulfonyl)-trans-4-azidoproline, methyl ester (17): In a 50 mL flask were combined 16 (0.60 g, 1.65 mmol) and 1.07 g (16.5 mmol, 10 equiv.) of sodium azide (Aldrich) in 10 mL of anhydrous DMF. The colorless solution was heated at ~60° C. under a $CaCl_2$ drying tube overnight, then allowed to cool and filtered. The flask and filter solids were washed with EtOAc, and the filtrate concentrated to dryness. The white residue was dissolved in EtOAc, washed twice with water, then brine, dried ($MgSO_4$), filtered, and concentrated to give a pale yellow, waxy solid. This was recrystallized from EtOAc/hexanes to give 0.43 g (1.39 mmol, 85%) of 17 as fine white needles. $^1$H-NMR (400 MHz, CDCl$_3$, δ ppm) 7.86 (dt, J=1 Hz, 8 Hz, 2H), 7.61 (tt, J=1 Hz, 8 Hz, 1H), 7.54 (tt, J=1Hz, 8 Hz, 2 H), 4.29 (t, J=8 Hz, 1H), 4.18 (m, 1H), 3.74 (s, 3H), 3.69 (q, J=5 Hz, 1H), 3.41 (dd, J=3 Hz, 11 Hz, 1H), 2.17 (m, 2H); $^{13}$C-NMR (400 MHz, CDCl$_3$, δ ppm) 179.46, 145.01, 140.85, 136.81, 135.14, 67.03, 66.97, 60.71, 60.37, 44.03; m/z: 311 (M+1)$^+$. The trans-stereochemistry was confirmed by X-ray crystal structure.

N-(benzenesulfonyl)-trans-4-aminoproline, methyl ester (18): A solution of 0.35 g (1.13 mmol) of 17 and 10% Pd/C (ca 50 mg) in 5 mL of methanol stirred under hydrogen (60 psi) overnight. The resulting mixture was filtered through a Celite plug and the filtrate concentrated to give 0.32 g (1.13 mmol, 100%) of 18 as a pale yellow syrup. Compound 18 was used without further purification. $^1$H-NMR (400 MHz, CDCl$_3$, δ ppm) 7.86 (d, J=8 Hz, 2H), 7.57 (t, J=7 Hz, 1H), 7.51 (t, J=8 Hz, 2H), 4.40 (t, J=8 Hz, 1H), 3.68 (s, 3H), 3.63 (m, 1H), 3.69 (q, J=5 Hz, 1H), 3.05 (m, 1H), 2.13 (m, 1H), 1.91 (m, 1H), 1.59 (br s, 2H); $^{13}$C-NMR (400 MHz, CDCl$_3$, δ ppm) 172.79, 138.30, 133.35, 129.44, 127.94, 59.85, 56.26, 52.90, 51.01, 40.02; m/z: 285 (M+1)$^+$.

N-(benzenesulfonyl)-trans-4-(6-(Boc-amino)caproyl) aminoproline methyl ester (19): To a mixture of 300 mg of 18 (1.06 mmol), 244 mg (1.06 mmol) of 6-(Boc-amino)-caproic acid (Bachem), and 485 mg (1.27 mmol, 1.2 equiv.) of HATU in 4 mL of DMF was added 525 μL (3.0 mmol, ~3 equiv.) of diisopropylethylamine. The resulting mixture was stirred at room temperature overnight, then diluted with ~100 mL EtOAc and washed with 1 N HCl (three times), 1 N NaOH (twice), then brine, and dried (MgSO$_4$), filtered, and concentrated to an orange oil. This was dissolved in CH$_2$Cl$_2$, loaded onto silica, and eluted with 3:2 CH$_2$Cl$_2$/CH$_3$CN to give 308 mg (0.62 mmol, 58%) of 19 as a foamy white solid. $^1$H-NMR (400 MHz, CDCl$_3$, δ ppm) 7.90 (dd, J=1 Hz, 8 Hz, 2H), 7.60 (tt, J=1 Hz, 8 Hz, 1H), 7.53 (tt, J=1 Hz, 8 Hz, 2H), 5.71 (d, J=6 Hz, 1H), 4.58 (br s, 1H), 4.53

(t, J=8Hz, 1H), 4.47 (m, 1H), 3.66 (s, 3H), 3.54 (q, J=5 Hz, 1H), 3.39 (dd, J=3 Hz, 11 Hz, 1H), 3.08 (m, 2H), 2.24 (m, 2H), 2.02 (t, J=8 Hz, 2H), 1.56 (m, 2H), 1.45 (m, 2H), 1.41 (s, 9H), 1.28 (m, 2H); $^{13}$C-NMR (400 MHz, CDCl$_3$, δ ppm) 173.21, 172.19, 164.53, 138.83, 133.62, 129.58, 128.04, 123.12, 59.13, 53.70, 52.97, 49.68, 40.68, 37.47, 36.59, 30.08, 28.82, 26.64, 25.38; m/z: 498 (M+1)$^+$.

concentrated to dry to give desired acid as white foam, 1.77 g (quantitative), which was used without further purification. $^1$H-NMR (400 MHz, CDCl$_3$, δ ppm), 7.86 (d, J=7.4 Hz, 2H), 7.56–7.45 (m, 3H), 7.30 (s, 5H), 6.49 (br s, 1H), 5.40 (s, 1H), 5.13 (s, 1H), 5.05 (s, 2H), 4.48 (s, 1H), 4.37 (s, 1H), 3.62 (br s, 2H), 3.30 (br s, 1H), 3.10 (m, 2H), 2.20 (br s, 2H), 1.93 (s, 2H), 1.43 (m, 4H), 1.24 (m, 2H). m/z: 484 (M+1)$^+$.

Compound G synthesis

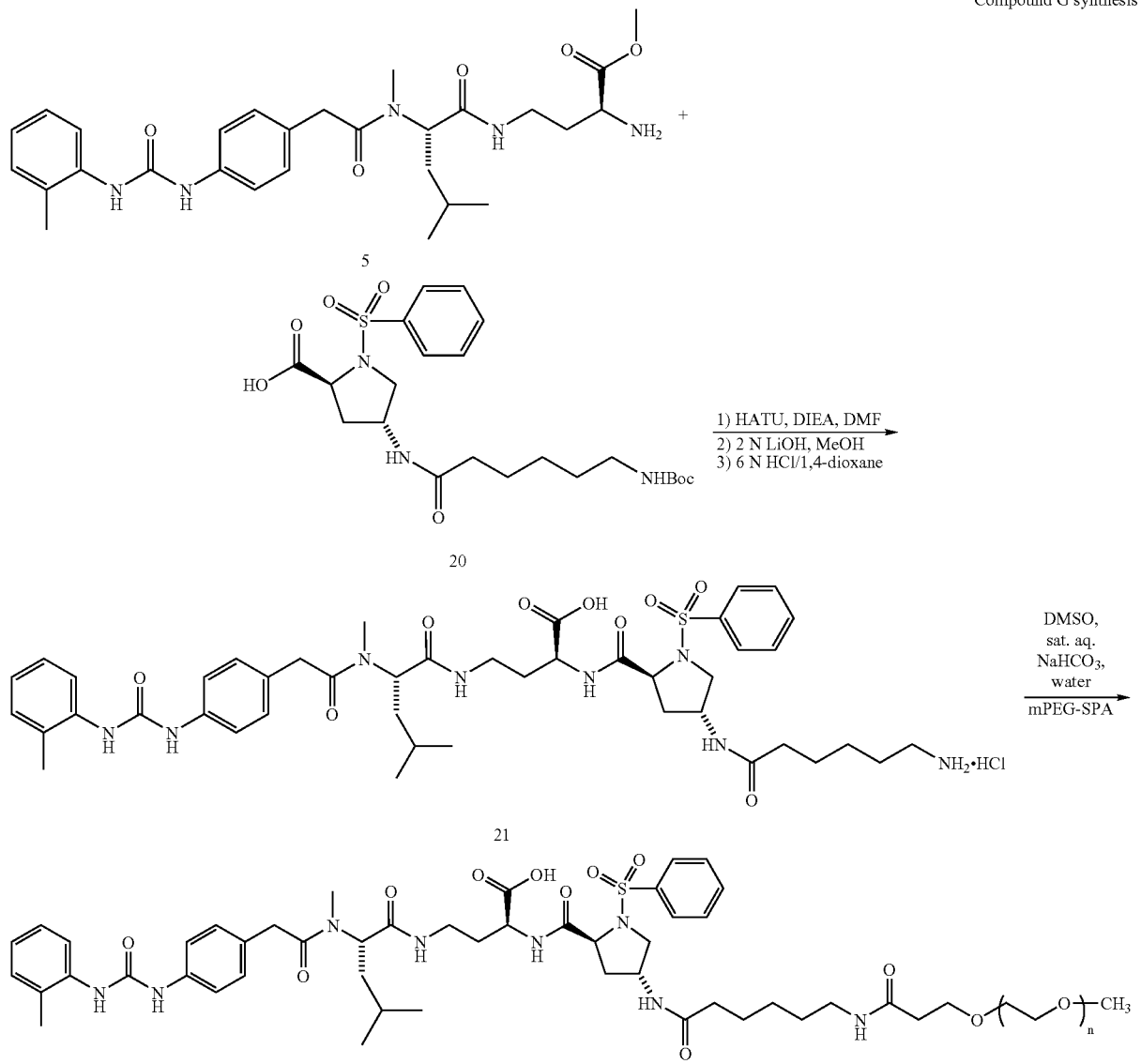

Compound 20: A mixture methyl ester 19 (1.75 g, 3.52 mmol) and 2 N LiOH (3 mL) in methanol (20 mL) was stirred at room temperature for 3 hours. The reaction mixture was cooled to 0° C. (ice water bath), 1 N HCl aqueous solution was added until the pH was approximately 3. The resulting mixture was diluted with EtOAc (ca. 100 mL), washed with water (twice), brine (twice), dried, filtered, Compound 21: To the mixture of acid (20, 750 mg, 1.55 mmol) and amine (5, 958 mg, 1.7 mmol) in DMF was added HATU (710 mg) followed by diisopropylethylamine (ca. 1.5 mL). The mixture was stirred at room temperature overnight, diluted with EtOAc, washed with water (three times), 1 N NaOH (twice), water, 1 N HCl (twice), water, saturated aqueous NaHCO$_3$, brine (twice), dried, filtered, and concentrated to give 1.60 g of crude product as white foam. Flash column chromatography gave 1.06 g of product (69%). ¹H-NMR (400 MHz, CDCl₃, δ ppm) 7.95 (d, J=7.6 Hz, 2H), 7.72 (s, 1H), 7.66 (d, J=8.0 Hz, 2H), 7.57 (t, J=7.5 Hz, 1H), 7.48 (d, J=7.9 Hz, 1H), 7.46 (d, J=7.4 Hz, 1H), 7.30 (d, J=8.5 Hz, 2H), 7.17–7.10 (m, 5H), 7.00 (t, J=6.7 Hz, 1H), 6.89 (br s, 1H), 5.75 (br s, 1H), 5.06 (br t, 1H), 4.70 (br t, 1H), 4.59 (br t, 1H), 4.50 (t, J=8 Hz, 1H), 4.24 (m, 1H), 3.73 (s, 3H), 3.71 (dd, 1H), 3.32 (m, 1H), 3.16 (m, 2H), 3.03 (m, 2H), 3.00 (s, 3H), 2.20 (s, 3H), 2.15 (m, 2H), 1.93 (m, 1H), 1.77–1.55 (m, 4H), 1.45–1.40 (m), 1.15 (m, 2H (d, H=6.6 Hz, 3H), 0.82 (d, J=6.5 Hz, 3H). m/e: 991 (M+1)⁺.

A solution of methyl ester (470 mg, 0.54 mmol) and 2 N LiOH (2 mL) in methanol was stirred at room temperature overnight, methanol was removed by rotary evaporator, cooled to 0° C. (ice water bath), and 1 N HCl was added until the pH was approximately 3. The resulting mixture was diluted with EtOAc washed with water (twice), brine (twice), dried, filtered, and concentrated to give the carboxylic acid 21. To the solution of acid in EtOAc was added 4 N HCl/dioxane (6 mL) and stirred at room temperature for ca. 3 hours and then concentrated. To the resulting solid was added EtOAc and then heated for ca. 30 minutes, cooled to room temperature, filtered, washed with EtOAc, and dried to give the product as a white solid (397 mg, 95%). ¹H-NMR (400 MHz, CDCl₃, δ ppm) 9.50 (s, 1H), 8.40 (d, J=7.9 Hz, 1H), 8.22 (s, 1H), 7.84 (m, 7H), 7.71 (m, 1H), 7.62 (m, 2H), 7.39 (d, J=8.0 Hz, 2H), 7.13 (m, 5H), 6.91 (t, J=7.2 Hz, 1H), 5.02 (br t, 1H), 4.0–4.15 (m, 3H), 3.80–3.55 (m, 3H), 3.35 (m, 1H), 3.18 (m, 1H), 3.05 (m, 1H), 2.90 (m, 1H), 2.85 (s, 3H), 2.71 (br s, 2H), 2.25 (s, 3H), 1.95–1.70 (m, 6H), 1.61–1.31 (m, 6H), 0.83 m/e=878.4 (M+1)⁺.

Compound G: To a solution of amine 21 (28 mg, 0.032 mmol) in DMSO (1 mL), was added 0.2 mL of saturated aqueous NaHCO₃ followed by water (2 mL), and then mPEG-SPA 30 k (903 mg, 0.029 mmol; see below) was added in portions. The mixture was stirred at room temperature overnight, diluted with anhydrous ethanol (25 mL) and then filtered. To the filtrate, anhydrous diethyl ether (ca. 70 mL) was added slowly to precipitated out the product. The resulting precipitate was filtered, the filter cake was washed with ether, dried to give 884 mg of white powder. The crude product was dissolved in boiling ethanol (ca 15 mL), cooled to room temperature, the precipitate was filtered, filter cake washed with anhydrous ethanol to give 789 mg (87%) of compound G as a white flake. ¹H-NMR (400 MHz, CDCl₃, δ) 3.60 ppm (ethylene-H).

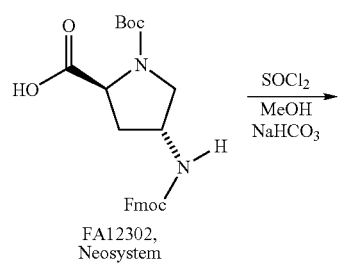

FA12302, Neosystem

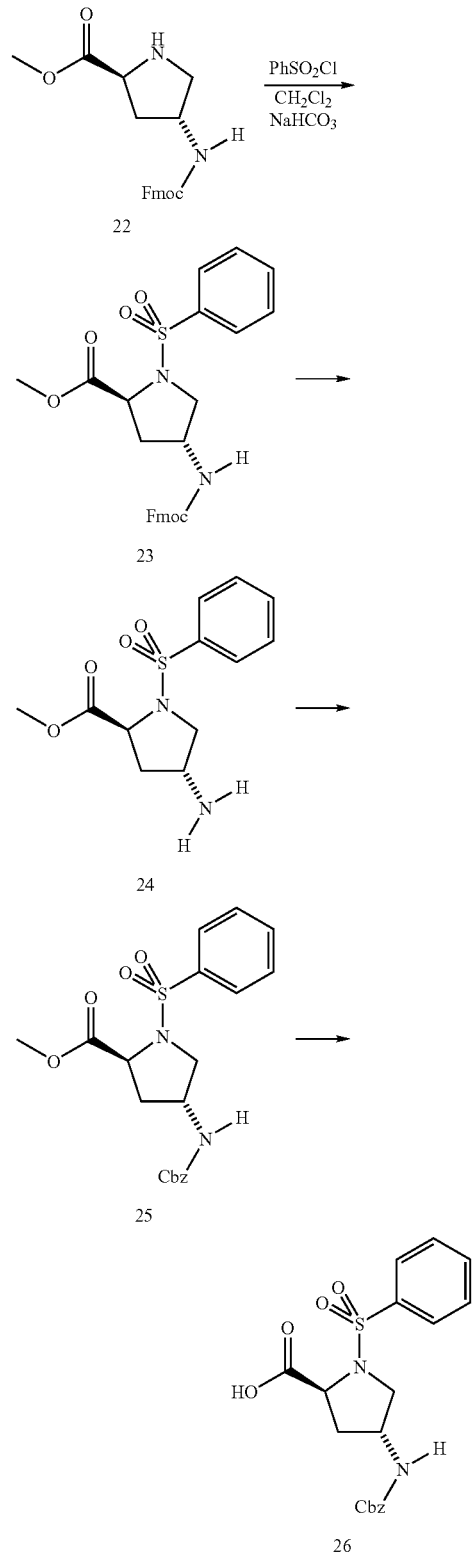

To a solution of protected proline (Neosystem, FA12302, 1.37 g, 3.0 mmol) in methanol (ca. 15 mL) SOCl₂ was added dropwise (ca. 3 mL). The mixture was stirred at room temperature for 3 hours, concentrated to dry under rotary evaporation. The resulting mixture was dissolved in methanol, saturated aqueous NaHCO$_3$ and solid NaHCO$_3$ were added until the pH was greater than 7. The resulting mixture was concentrated to dryness, suspended in EtOAc, dried with anhydrous Na$_2$SO$_4$, filtered through a Celite plug. The filtrate was concentrated and further dried to crude amine 22 as a brown solid. The crude product was used without purification.

To the solution of above mentioned amine in CH$_2$Cl$_2$ was added saturated aqueous NaHCO$_3$ (ca 1 mL) followed by benzene sulfonyl chloride. The mixture was stirred at room temperature overnight, diluted with EtOAc, washed with saturated aqueous NaHCO$_3$ (twice), water (twice), 5% aqueous citric acid (twice), water, and brine. The resulting organic solution was dried, filtered, concentrated to give a colorless oil 23. The crude product was used without purification.

The solution of above mentioned crude product 23 in CH$_2$Cl$_2$ was added Et$_2$NH, and stirred at room temperature over night and then concentrated to dry, then suspended in EtOAc, filtered through a plug of Celite, and concentrated to give a crude amine 24 as brown oil.

To the solution of crude amine 24 in CH$_2$Cl$_2$ was added CbzOSu followed by Et$_3$N, the mixture was stirred at room temperature for 2 hours, diluted with EtOAc, washed with water (twice), water (twice), 5% citric acid (three times), water, brine, dried and concentrated to give a crude product. Purification by flash column chromatography gave 702 mg (56% yield from FA12302) of 25. $^1$H-NMR (400 MHz, CDCl$_3$, δ ppm) 7.86 (s, 1H), 7.83 (s, 1H), 7.55–7.43 (m, 3H), 7.37–7.26 (m, 5H), 5.00 (s, 2H), 4.81 (br d, J=6.4 Hz, 1J=7.2 Hz, 1H), 4.26 (m, 1H), 3.66 (s, 3H), 3.59 (dd, J=10.7, 5.6 Hz, 1H), 3.35 (dd, J=10.6, 3.2 Hz, 1H), 2.18 (m, 2H).

Compound H synthesis

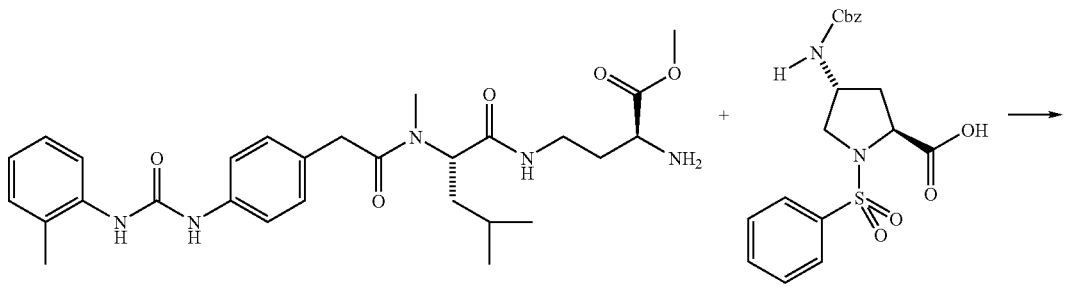

5 + 26

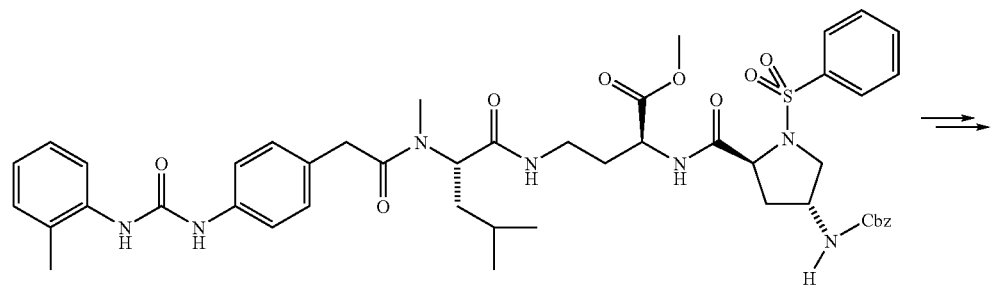

27

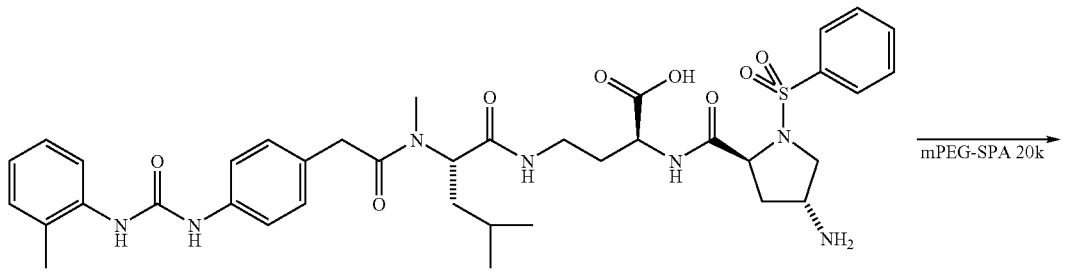

28

-continued

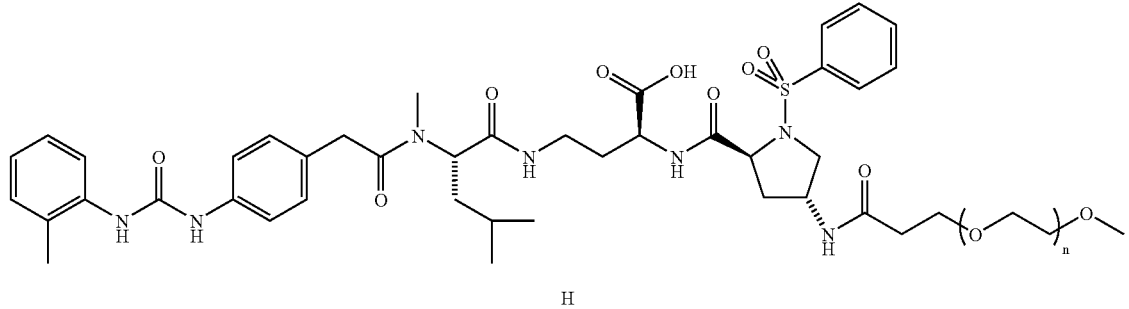

H

The methyl ester 25 solution (318 mg, 0.76 mmol) in methanol with 2 N LiOH (2 mL) was stirred at room temperature for 2 hours, methanol was removed by rotary evaporator, cooled to 0° C. (ice water bath) and 1 N HCl was added until the pH was less than 6. Diluted with EtOAc, washed with water (twice), brine (twice), dried, concentrated to give the acid 26. To the mixture of the crude acid 26, amine (5, 431 mg), and HATU (364 mg) in DMF was added diisopropylethylamine (ca. 1 mL) and stirred at room temperature overnight. The reaction mixture was diluted with EtOAc, washed with water (twice), 1 N NaOH (twice), water, brine (twice), dried, filtered, concentrated to give a brown foam, which was then purified by flash column chromatography to give 620 mg (89%) of 27 as a white foam. The crude product was used without purification.

Compound 28: A mixture of methyl ester (27, 523 mg, 0.57 mmol) and 2 N LiOH (1.5 mL) in methanol (5 mL) was stirred at room temperature for 3 hours. The reaction mixture was cooled to 0° C. (ice water bath), 1 N HCl was added until pH ~3, diluted with EtOAc, washed with water (twice), brine (twice), dried, filtered, concentrated to give 473 mg of white foam as crude product and was used without purification. $^1$H-NMR (400 MHz, CDCl$_3$, δ ppm) 8.95 (s, 1H), 8.39 (d, J=7.9 Hz, 1H), 7.83 (m, 4H), 7.66 (d, J=7.4 Hz, 1H), 7.60 (m, 2H), 7.40–7.28 (m, 4H), 7.13 (m, 4H), 6.92 (t, J=7.4 Hz, 1H), 5.04 (dd, J=9.7, 6.0 Hz, 1H), 4.93 (dd, J=17.3, 12.4 Hz, 2H), 4.27 (m, 1H), 4.19 (m, 1H), 4.13 (m, 1H), 3.65 (m, 1H), 3.60 (m, 3H), 3.20 (m, 1H), 3.05 (m, 2H), 2.85 (s, 3H), 2.22 (s, 3H), 1.97 (m, 1H), 1.89 (m, 1H), 1.78 (m, 2H), 1.55 (m, 2H), 1.26 (m, 1H), 0.84 (d, J=6.7 Hz, 3H), 0.81 (d, J=6.5 Hz, 3H). m/e=899.1 (M+1)$^+$.

The mixture of the crude acid, and 53 mg of Pd/C in methanol/water was stirred under 60 psi of H$_2$ for 4 hours. The resulting reaction mixture was filtered through a Celite plug, and concentrated to give 337 mg. The product was precipitated from mixture of methanol/CH$_2$Cl$_2$/EtOAc solution to give 235 mg, 98.7% pure by HPLC. HPLC of the remaining mixture gave additional 46 mg. Total of 281 mg of 28 (64% from 26). m/e=765.2 (M+1)$^+$.

Compound H: To a mixture of amine 28 (40 mg, 0.053 mmol), saturated aqueous NaHCO$_3$ (0.2 mL), DMSO (0.8 mL), and water (1.6 mL) was added mPEG-SPA (938 mg, 0.044 mmol, 20K PEG from Shearwater). The mixture was stirred at room temperature overnight and then diluted with ethanol (13 mL). Water (80 mL) was added slowly to precipitate out the product. The white solid was filtered, washed with ether and dried to give 940 mg of crude product. The crude product was dissolved in 4 mL of water, filtered, diluted with 25 mL of ethanol, 70 mL of ether was added slowly to precipitate. The solid was filtered, the filtrate cake was washed with mixture of ether/ethanol (2:1), and dried to give a white powder (785 mg). This process was repeated one more time to give 746 mg (77%) of final product as white powder. $^1$H-NMR (400 MHz, CDCl$_3$, δ) 3.60 ppm (ethylene-H).

Scheme 1

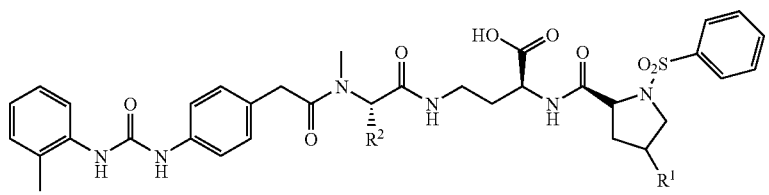

| Compound | R$^1$ | R$^2$ |
|---|---|---|
| B | Hydrogen | 2-methylpropyl |
| A | Hydrogen | 4-(6-aminohexanoyl)amino-n-butyl |
| C | anti-amino | 2-methylpropyl |
| H | anti-amino-mPEG 20k | 2-methylpropyl |
| D | syn-(6-aminohexanoyl)amino | 2-methylpropyl |
| I | syn-(6-arninohexanoyl)amino-mPEG 20k | 2-methylpropyl |

-continued

Scheme 1

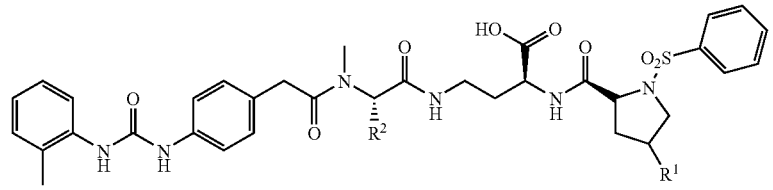

| Compound | R¹ | R² |
|---|---|---|
| E | anti-(6-aminohexanoyl)amino | 2-methylpropyl |
| L | anti-(6-aminohexanoyl)amino-mPEG 20k | 2-methylpropyl |
| F | syn-amino | 2-methylpropyl |
| J | syn-amino-mPEG 20k | 2-methylpropyl |
| G | anti-(6-aminohexanoyl)amno-mPEG 30k | 2-methylpropyl |
| K | anti-(6-aminohexanoyl)amino-mPEG 50k | 2-methylpropyl |
| M | anti-(6-aminohexanoyl)amino-mPEG 5k | 2-methylpropyl |
| N | anti-(6-aminohexanoyl)amino-mPEG 2k | 2-methylpropyl |
| O | anti-(6-aminohexanoyl)amino-nPEG 0.4 k | 2-methylpropyl |

In general, an amine containing compound can be PEGylated according to the following procedure:

To a solution of 0.21 mmol of amine in a mixture of 4 mL DMSO, 2 mL saturated aqueous NaHCO₃, and 6 mL of H₂O, was added 0.17 mmol of mPEG-SPA. The reaction mixture was stirred at room temperature for several hours, and monitored by HPLC using a gel filtration column. The reaction mixture was diluted with 80 mL ethanol, and optionally filtered. Ethyl ether (ca. 300 mL) was added to precipitate out the product, which was then filtered, washed with ethanol, ethyl ether, and dried. The crude product was then heated in boiling ethanol (ca. 100 mL) until clear, and allowed to precipitate upon cooling to room temperature. The product was filtered, washed with ethanol, ethyl ether, and dried. This process was repeated until the product was free of un-PEGylated starting material. The typical yield was >80%. For PEGs larger than 20 kDa, a more pure product can be produced if PEG is attached to a linker (for example, a linker derived from 6-aminocaproic acid) on the inhibitor.

For the generation of A-PEG, compound A (50 mM in dimethylsulfoxide) was diluted 10-fold into a freshly prepared solution containing 50 mM HEPES, pH 8.0, 150 mM NaCl, and 5 mM 20 kDa-methoxyPEG-succinimidyl propionate (Nektar Molecular

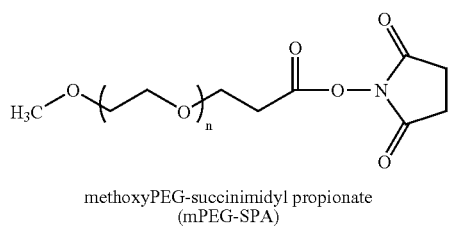

methoxyPEG-succinimidyl propionate
(mPEG-SPA)

Engineering, Huntsville, Ala.) and incubated at room temperature for 1 h. PEG groups having different molecular weights (i.e., different number of ethylene glycol repeats) can be added using a PEG-succinimidyl propionate of the desired size. For example, a PEG group having a molecular weight of less than 2,000, 2,000, 3,400, 5,000, 20,000, 30,000, 40,000, 50,000, 60,000, 70,000 or more can be attached to a compound. 50 mM ethanolamine was added to quench unreacted PEG and the sample was desalted on a P6DG (BioRAD) desalting column to remove unreacted compound A. A-PEG was formulated in phosphate buffered saline (PBS). Compounds H, I, L, and J were generated as follows. 0.097 mmol of 20 kDa-methoxyPEG-succinimidyl propionate was added to 0.11 mmol of each compound in 2 mL dimethylsulfoxide, 0.5 mL saturated NaHCO₃, 4 mL water, and stirred overnight at room temperature. The reactions were diluted with vigorous stirring with 30 mL ethanol and then with 100 mL ethyl ether. The suspension was filtered and the resulting white solid was washed three times with ethyl ether, and dried under vacuum. The crude product was dissolved in hot ethanol, and the PEGylated product was precipitated out of the mixture by the addition of ethyl ether. The precipitate was collected by filtration, washed, and dried. This process was repeated one more time to provide PEGylated product as a white power that was >99% pure when analyzed by high pressure liquid chromatography. For efficacy studies in EAE and for lymphocytosis studies, an inactive control PEG was used that was synthesized by reacting 20-kDa-methoxyPEGsuccinimidyl propionate with isobutylamine.

Multifunctional compounds having more than one cell adhesion inhibitory group, and a PEG moiety can be produced with a multifunctional PEG compound. A PEG compound can have more than one reactive group to link to a cell adhesion inhibitor. For example, a PEG compound can have a reactive group at two ends. When such a PEG compound is allowed to react with an inhibitor having a complementary reactive group, a compound with two cell adhesion inhibitory groups linked by a PEG moiety can result. Compound P, shown below, is an example of such an inhibitor. Cell adhesion inhibitors can also be linked by alkylene linkers, such as shown below for compound Q.

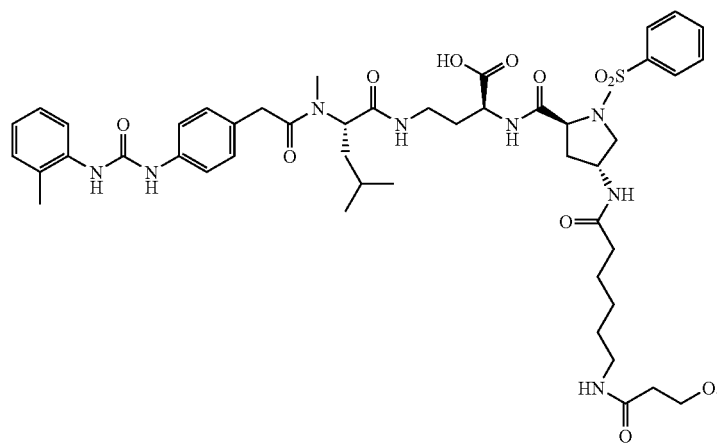
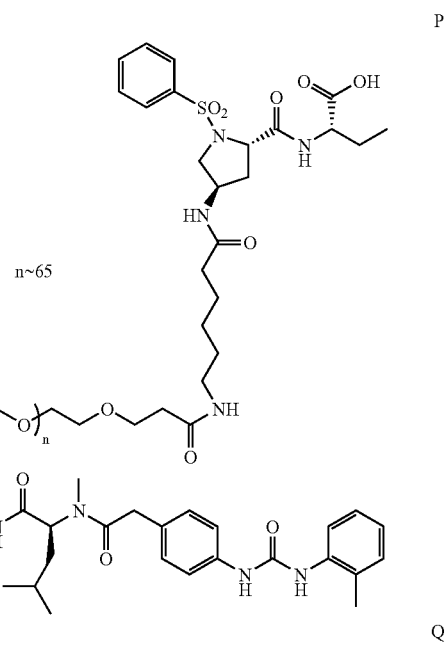

P

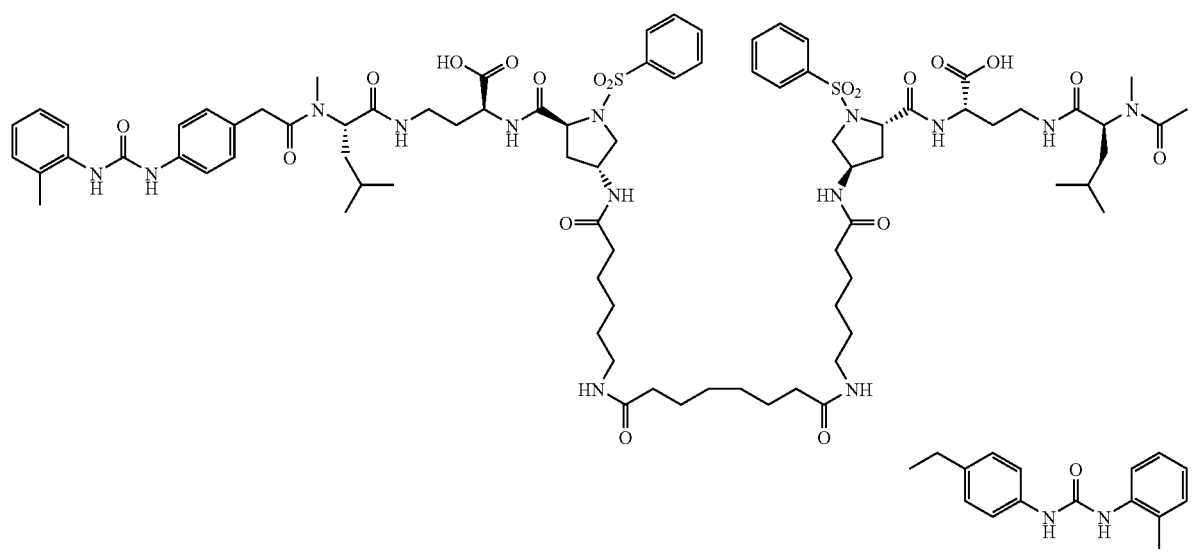

Q

Cell Binding and Adhesion Assays

The α4β1-expressing Jurkat human T-cell line (a gift from S. Burakoff, Dana Farber Cancer Institute, Boston, Mass.), and the α4β7-expressing human B-cell line, JY (American Type Tissue Collection, Rockville, Md.) were maintained in culture at 37° C. in RPMI-1640 medium supplemented with 10% fetal bovine serum (FBS). K562 cell lines transfected with either the human α1-integrin chain (Phil Gotwells, Biogen, Inc) or with the human α2 integrin chain (a gift from M. Hemler, Dana Farber Cancer Institute, Boston, Mass.) were maintained in RPMI-1640 medium supplemented with 10% FBS and 1 mg/mL G418. All cells were periodically monitored for high integrin surface expression by FACS analysis. The binding of the various inhibitors to α4β1 were assessed on Jurkat cells by competition using radioactive $^{35}$S-B as a reporter for a 1 occupancy. Jurkat cells were pelleted by centrifugation, washed two times with TBS (50 mM Tris HCl, 150 mM NaCl, 0.1% bovine serum albumin, 2 mM glucose, 10 mM HEPES pH 7.4), suspended at approximately 2×10$^6$ cells/mL in TBS, and counted using a Neubauer hemocytometer. The cells were further diluted 2×10$^6$ cells/mL with TBS containing 1 mM CaCl$_2$ and 1 mM MgCl$_2$ and treated with serial dilutions of test compound for 1 hour, and then 5 nM $^{35}$S-B, an amount sufficient to bind all unoccupied receptors, was added for 10 minutes before measuring the bound counts. The cells were then pelleted by centrifugation, resuspended in 100 μL of TBS plus Mn$^{2+}$, and transferred to a scintillation vial containing 2.9 mL of ScintiVerse II (Fisher Scientific). Cell-associated radioactivity was quantified by scintillation counting. All studies were performed in siliconized 1.5 mL eppendorf tubes with a standard 1 mL sample volume. Each condition was tested in at least two independent studies. Non-specific binding of $^{35}$S-B to cells was assessed at each cell density and $^{35}$S-B concentration in TBS but in the absence of added metal ion. Specific counts bound were calculated by subtracting non specific counts from total counts bound. Counts bound under these conditions measures integrin that is not occupied by the test compound and is therefore free to bind the $^{35}$S-B. The competition format was also used for kinetic binding studies. Binding and dissociation constants were calculated from α4β1 that remained free to bind the $^{35}$S-B after treatment with test compound.

The ability of test compounds to block α2β1/collagen I and α1β1/collagen IV interactions were evaluated in cell adhesion assays. Collagen I and collagen IV were immobilized onto a 96-well Corning Easy Wash plate (Corning Cat. No. 25801). Human integrin-expressing cell lines (2×10$^5$/well) were labeled with a fluorescent compound, 2 μM BCECF-AM (Molecular Probes, Eugene, Oreg., Cat# B1150), and added with or without test compounds. After 30 minutes, the plates were washed, and bound cells quantified in a Cytofluor fluorescence plate reader. The assay buffer was TRIS-buffered saline (TBS: 24 mM TRIS, 137 mM NaCl, 2.7 mM KCl, 2 mM glucose, 0.1% BSA, pH 7.4), containing 1 mM MnCl$_2$. The specificity of binding was controlled for using integrin specific neutralizing monoclonal antibodies. The antibodies were run at 10 μg/mL on each day of the assay and were as follows: anti-α4β1, mAb HP1/2 (Biogen); anti-α2β1, mAb 26G8 (Biogen); and α1β1, mAb AJH10 (Biogen).

Samples were also evaluated for function using the VCAM-Ig direct binding assay. Details for the construction of the VCAM-Ig animal cell expression vector, the generation of a Chinese hamster ovary (CHO) cell line expressing VCAM-Ig, conjugation of the VCAM-Ig to alkaline phosphatase, and the development of a direct binding assay for characterizing α4β1 and α4β7 binding to VCAM-Ig were as previously described (see Lobb, R. R., et al. (1995) *Cell Adhes. Commun.* 3:385–397).

Female Lewis rats, four per route of administration, received compound R (see below) at either 30 mg/kg subcutaneously, or 1 mg/kg intravenously, or compound H at 1 mg/kg, intravenously or subcutaneously. Blood samples (250 μL/bleed) were obtained at specific timepoints after administration. For compound H, blood samples were drawn at 0, 8 minutes, 15 minutes, 30 minutes, and after 1 hour, 2, 4, 6, 8, 24, 32, 48, 72 and 168 hours following i.v. administration, and 1, 2, 4, 6, 8, 24, 32, 48, and 72 hours following s.c. administration. Serum samples were analyzed for compound H levels using an electrochemiluminescence assay. PK parameters were calculated from the mass spectrometry data by noncompartmental analysis. PK parameters include $C_{MAX}$ (maximum serum concentration), $t_{MAX}$ (time to achieve maximum serum concentration), CL (systemic clearance), Vss (volume of distribution at steady state), $t_{1/2}$ (terminal phase half-life), and bioavailability. Area under the curve (AUC) was calculated using the trapezoidal rule. Percent bioavailability was calculated from the following equation: $(AUC_{extravascular}/AUC_{IV}) \times (Dose_{IV}/Dose_{extravascular}) \times 100$. For compound R[1], blood samples were drawn and analyzed as previously described (see Leone, D. R., et al. (2003) *J. Pharmacol. Exp. Ther.* 305: 1150–1162).

Levels of compound H in rat plasma were measured by electrochemiluminescence in a competition assay format with compound A-biotin as a probe using a modified version of the assay previously described (see Weinreb, P. H., et al. (2002) *Anal. Biochem.* 306:305–313, and Leone, D. R., et al. (2003) *J. Pharmacol. Exp. Ther.* 305:1150–1162, each of which is incorporated by reference in its entirety). Dilutions of test samples in 50 mM HEPES pH 7.5, 100 mM NaCl, 0.1% Triton X-100, 1 mM MnCl$_2$, 1% rat plasma, 50 ng/mL α4β1 and 0.1 μg/mL ruthenium labeled mAb B5G10 were incubated at room temperature for 20 min. 0.5 nM A-biotin was added and samples were incubated for 60 minutes at room temperature. 50 μL of a 0.5 mg/mL solution of Dynabeads M-280 Streptavidin beads (Cat No. 402–175-02, Igen, Inc., Gaithersburg, Md.) that have been prepared in assay buffer containing 8% rat plasma was added and the samples were incubated for 30 minutes at room temperature with constant mixing. 150 μL of Origen assay buffer was added and samples were analyzed in a model 1100–1000 Origen analyzer (Igen, Inc) following the manufacturer's instructions. Concentrations of compound H were interpolated from a standard curve generated with compound H that had been diluted with plasma.

Assessing Lymphocyte Counts and Subtypes Following Inhibitor Treatments

Female Lewis rats were injected with a single dose of either compound H (1 mg/kg, s.c in PBS), or compound R (30 mg/kg, s.c., in TRIS/lactose) or with their respective vehicles at time 0. At each timepoint, 0.3 mL blood from triplicate animals was drawn from the jugular vein without anesthesia and collected into Capiject purple-top microtainer tubes containing EDTA (Terumo Medical Corporation #T-MQK). Plasma samples were analyzed for lymphocyte count using an Abbott CellDyn 3500 cell analyzer. Blood samples from the compound H-treated animals were drawn at 4 hours, 8 hours, 12 hours, and on days 1, 2, 3, 4, 5, 6, 7, 8, and 9 and for the compound R-treated animals after 2, 6, 24, and 48 h.

Assessing Inhibitor Function in a Rat EAE Model

Female Lewis rats obtained from Harlan Sprague Dawley were housed in ventilated cage racks and allowed food and water ad libitum. At approximately 9 weeks of age animals were immunized with an emulsion of Guinea pig Mylein Basic Protein (MBP) peptide in complete Freund's adjuvant. MBP peptide sequence of GPMBPYGSLPQKSQRS-DENPV (amino acid residues 68–86), 100 μg/mL in PBS, was diluted with an equal volume of incomplete Freund's adjuvant. Before emulsification, ground *mycobacterium tuberculosis* was added to 4 mg/mL. Animals were anesthetized with isoflurane and immunized with a single footpad injection of 100 μL of the emulsion. Animals were weighed and observed for signs of paralysis starting on day 7 post immunization and daily thereafter. Each treatment group contained 13 animals. Compound R was administered at 30 mg/kg, s.c., QD, during days 5–14. Untreated rats and TRIS/Lactose vehicle-treated controls were also monitored. For compound H treatment, rats were injected i.v. on day 7 with compound H (1 mg/kg) or with control PEG (1 mg/kg)

in the same buffer. The following grading system was used to quantify disease severity: 0.5=half of tail limp; 1.0=whole tail limp; 1.5=whole tail limp with a small amount of gait disruption; 2.0=hind limb weakness (waddling gait or one dragging leg); 2.5=hind limb weakness (one dragging leg with a small amount of loss of motile function in opposite leg); 3.0=hind limb paralysis (both legs dragging; some slight hind limb movement); 3.5=hind limb paralysis (both legs dragging with a small amount of forelimb weakness); 4.0=hind limb and front limb paralysis (sufficient to prevent movement); 5.0=moribund or death. All procedures using animals were conducted in accordance with the NIH Guide for the Care and Use of Laboratory Animals and approved by the Institutional Animal Care and Use Committee.

In vitro and in vivo properties of PEGylated inhibitors

Compound R (2S-{[1-(3,5-dichloro-benzenesulfonyl)-pyrrolidine-2S-carbonyl]-amino}-4-[4-methyl-2S-(methyl-{2-[4-(3-o-tolyl-ureido)-phenyl]-acetyl}-amino)-pentanoylamino]-butyric acid) is a small molecule inhibitor with extraordinary potency and selectivity for α4β1. Despite its high affinity for α4β1 ($K_D$ of 9 pM), when compound R was tested in vivo in EAE, a daily, 30 mg/kg s.c. treatment regimen was needed to achieve efficacy. The high dose requirement for efficacy was largely driven by its short circulating half-life. In an attempt to improve the pharmacokinetic (PK) properties of this class of VLA-4 inhibitors, methoxy-polyethylene glycol (MPEG) was attached using a targeted approach where amino groups were engineered into the inhibitor as sites for attachment. Compound B was selected as the framework for the modifications. Compound B is indistinguishable from compound R in its integrin binding properties (see below). Scheme 1 shows a schematic illustrating the positions of the attachment sites within B (see above). Two target sites were chosen based on previous experience generating functional conjugates of α4β1 inhibitors (see Pepinsky, R. B., et al. (2002) *Biochemistry* 41:7125–7141). PEGylated inhibitors were generated by reacting each inhibitor with mPEG-succinimidyl propionate and purifying the PEGylated product.

The affinities of the PEGylated inhibitors for α4β1 were calculated from association and disassociation rate constants using a kinetic analysis. For these studies, Jurkat cells expressing α4β1 (75,000 copies/cell) were treated with the inhibitors and then $^{35}$S-B was added as a probe to detect free α4β1. The levels of bound inhibitor were calculated from a measure of total $^{35}$S-B bound in the absence of added inhibitor and counts bound following inhibitor treatment. Results from these analyses are summarized in FIG. 1 and Table 1. On-rates for all the samples were similar, ranging from $4.0 \times 10^6$ M$^{-1}$sec$^{-1}$ for compound B to $2.4$–$3.2 \times 10^6$ M$^{-1}$sec$^{-1}$ for the five PEGylated compounds (see FIG. 1a and Tables 1 and 2). Off-rates varied by 10-fold from unmodified compound B, which was the tightest binder, to compound J, which dissociated somewhat faster than the other PEGylated compounds (FIG. 2a). Rate constants that were calculated from the binding data are summarized in Table 1. From on- and off-rate constants, the $K_D$ of compound B for α4β1 was calculated to be 5 pM, while $K_D$ values for compounds A-PEG, H, I, L, and J were 50, 19, 72, 31, and 61 pM, respectively. Compound H was selected as the lead candidate from this analysis because of its slightly higher affinity for α4β1. IC$_{50}$ values were calculated from equilibrium binding studies on Jurkat cells through competition using $^{35}$S-B as a reporter in buffer containing 1 mM Ca$^{2+}$ and 1 mM Mg$^{2+}$.

TABLE 1

| Compound | $k_{on}/10^6$ (M$^{-1}$s$^{-1}$) | $k_{off}/10^{-4}$ (s$^{-1}$) | $K_D$ (pM) | IC$_{50}$ (nM) | IC$_{50}$(HP) (nM) |
|---|---|---|---|---|---|
| R | 1.5 | 0.12 | 9 | 0.15 | 0.8 |
| B | 4.0 | 0.19 | 5 | 0.21 | 1.5 |
| A-PEG | 2.4 | 1.2 | 50 | 0.78 | 2.2 |
| H | 3.2 | 0.61 | 19 | 0.64 | 1.2 |
| I | 2.5 | 1.8 | 72 | 0.65 | 2.5 |
| L | 2.4 | 0.76 | 31 | 0.46 | 1.5 |
| J | 3.1 | 1.9 | 61 | 2.4 | 2.5 |
| A | 2.0 | 5.3 | 250 | 0.35 | 2.1 |
| A-Ac | 2.2 | 1.0 | 45 | 0.73 | 2.2 |
| C | 3.0 | 1.2 | 40 | 1.2 | 2.1 |
| D | 3.3 | 2.0 | 61 | 1.5 | 7.9 |
| E | 2.5 | 1.1 | 44 | 1.4 | 2.3 |
| F | 3.4 | 2.4 | 70 | 3.5 | 8.7 |

TABLE 2

| | DBA IC$_{50}$ (nM) | | | % bound | | PK (s.c.) | |
| compound | Mn$^{2+}$ | Ca$^{2+}$Mg$^{2+}$ | 100% rat plasma | Mn$^{2+}$ 60 min | Ca$^{2+}$Mg$^{2+}$ 30 min | F % | T$_{1/2}$ |
|---|---|---|---|---|---|---|---|
| B | 1.2 | 2 | 13 | >95 | >90 | 21 | 2.5 (i.v.) |
| I | 7 | 28 | 11 | 84 | 49 | 100 | 19 |
| J | 6 | 4 | 11 | 87 | 50 | 52 | — |
| L | 4 | 14 | 13 | 90 | 63 | 100 | 34 |
| G | 3 | 8 | 9 | 96 | 60 | 46 | 28 |
| H | 4 | 5 | 15 | 94 | 64 | 30 | 18 |
| P | 1.6 | 1.6 | 3.4 | 100 | 80 | — | — |
| Q | 4.3 | 74 | (0% @ 50 nM) | 93 | 0.1 | — | — |

The following studies were performed to further characterize the properties of PEGylated inhibitors. First, their selectivity for α4β1 was evaluated by assessing the binding of PEGylated inhibitors to cells expressing α4β7, α1β1, and α2β1 (Table 3). The PEGylated compounds were highly selective for α4β1. Like compound R, the affinities of the PEGylated inhibitors were >2,000 fold higher for α4β1 than for the related integrin, α4β7, which shares many of the same ligands as α4β1. No binding of the inhibitors to α1β1 and α2β1 was detected at 10 μM of compound, the highest dose tested (Table 3). The PEGylated inhibitors were active on human, rat, and mouse α4β1 with no apparent differences in affinity.

The results presented in Table 3 summarize the integrin selectivity for PEGylated inhibitors. The selectivity of the PEGylated inhibitors for the four integrins indicated were tested in adhesion formats for α1β1 and α2β1, and by direct binding for α4β7. Serial dilutions of each compound were tested and $IC_{50}$ values calculated from the concentration dependence of the inhibition curves. $K_D$ values derived from kinetic data are shown for binding to α4β1.

TABLE 3

| Integrin | compound B | compound A-PEG | compound H | compound I |
|---|---|---|---|---|
| α4β1 | 5 pM | 50 pM | 19 pM | 72 pM |
| α4β7 | >1 μM | >1 μM | >1 μM | 0.5 μM |
| α2β1 | 5 μM | >10 μM | >10 μM | >10 μM |
| α1β1 | >10 μM | >10 μM | >10 μM | >10 μM |

Second, the effect of protein binding on the affinity of the PEGylated inhibitors for α4β1 on Jurkat cells was evaluated from equilibrium binding measurements. A slight shift in $IC_{50}$ values was observed for all the inhibitors in the presence of added human plasma as compared to values generated in the absence of plasma. An $IC_{50}$ value of 1.2 nM was measured for compound H in 100% plasma versus values of 2.2, 2.5, 1.5, and 2.5 nM for compounds A-PEG, I, L, and J, respectively (Table 1). The large discrepancy in the binding constants calculated from the adhesion assay shown in Table 1 ($IC_{50}$=0.64 nM for compound H) and from the kinetic data ($K_D$=19 pM) arises because the affinity constants of the hybrid inhibitors for α4β1 are lower than the concentration of α4β1 in the binding assay. Consequently, $IC_{50}$ values in the adhesion assay of <1 nM reflect the concentration of α4β1 and not the affinity for α4β1, as discussed elsewhere (see Pepinsky, R. B., et al. (2002) *Biochemistry* 41:7125–7141).

Third, the effect of PEG chain length on binding was evaluated. For these studies, a series of compounds based on compound E containing 0.35, 2, 5, 20, 30, and 50 kDa-mPEG was synthesized and tested for binding to α4β1 on Jurkat cells with VCAM-Ig as a reporter (see methods). $IC_{50}$ values of <1.0, 0.8, 1.7, 3.7, 3.0, and 3.2 nM were measured for the six PEGylated compounds, respectively (see Table 4). Although there clearly was a dependence of PEG size on the $IC_{50}$ for binding of the compounds to α4β1, the effect was small.

TABLE 4

| compound | PEG size (kDa) | $IC_{50}$ (nM) |
|---|---|---|
| O | 0.35 | <1.0 |
| N | 2 | 0.8 |
| M | 5 | 1.7 |
| L | 20 | 3.7 |
| G | 30 | 3.0 |
| K | 50 | 3.2 |

Compound H was selected for in vivo studies based on other considerations. First, based on extensive published PK profiling studies (see, for example, Knauf, M. J., et al. (1988) *J. Biol. Chem.* 263: 15064–15070, which is incorporated by reference in its entirety), compounds with PEGs of 5 kDa or smaller attached are not expected to produce an acceptable increase in systemic exposure. Second, the attachment of a large PEG can impact a compound's bioavailability and tissue penetration. Based on such considerations, both the 20 kDa and 30 kDa PEGylated inhibitors were tested in vivo. The 30 kDa version was less effective at eliciting a lymphocytosis response than the corresponding product with a 20 kDa-PEG attached and no further in vivo studies on the 30 kDa version were performed.

Figure 2:
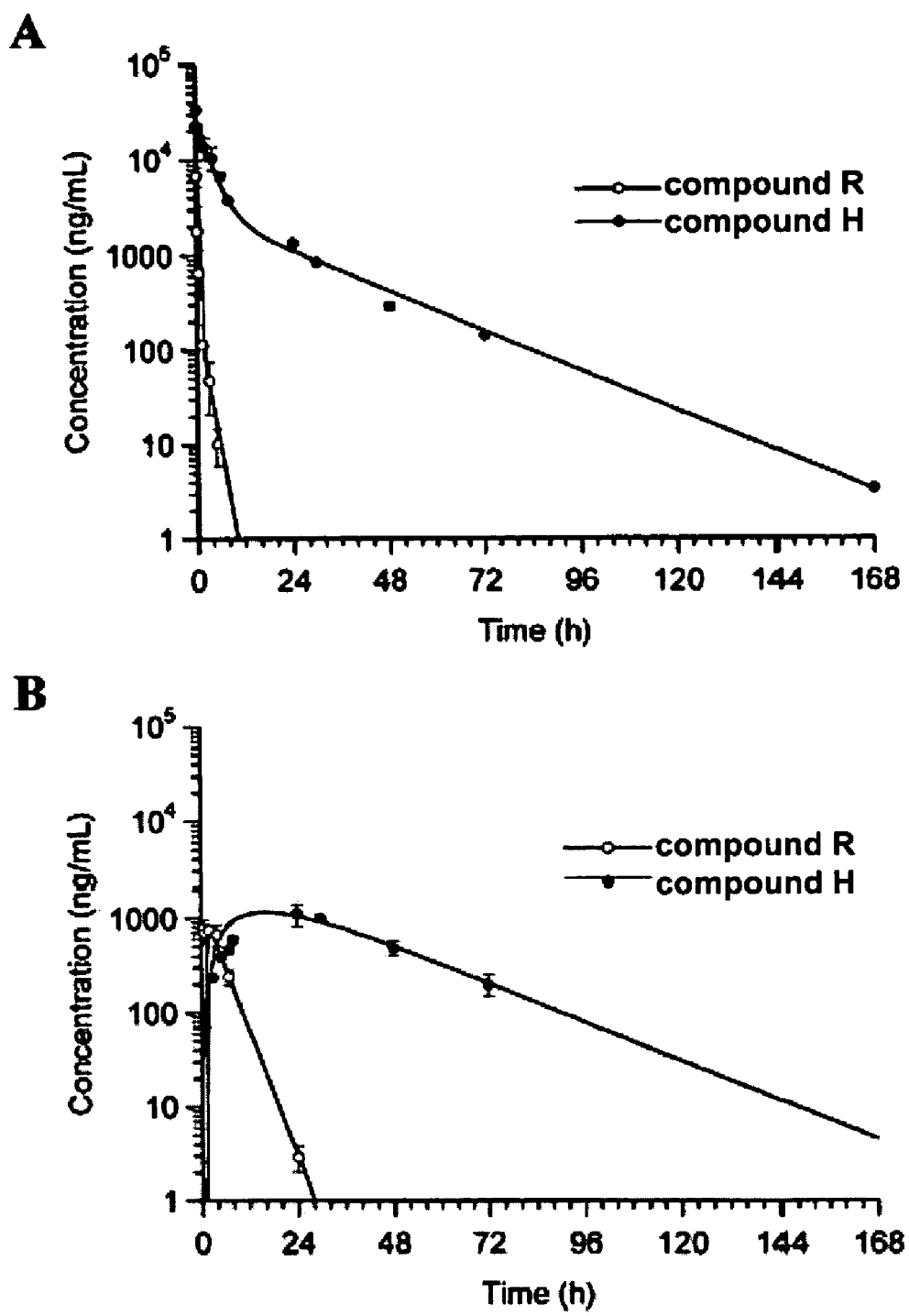
FIGS. 2a and 2b are graphs depicting the pharmacokinetic properties of compounds.

The pharmacokinetic properties of compounds H and R were evaluated by noncompartmental analysis following i.v. and s.c. administration in female Lewis rats (FIG. 2). PK parameters calculated from the data are summarized in Table 5. When administered i.v. (FIG. 2a), both compounds showed a multi-exponential disposition with a rapid initial decline followed by a less steep terminal phase. Compound R was rapidly cleared from circulation. The rate of clearance was 426 mL/h/kg and the terminal half-life of compound R was 1.1 h. In contrast, compound H had a 70-fold slower clearance rate, 6.2 mL/h/kg, and a longer terminal half-life, 17.9 hours, than the unmodified inhibitor. PK data for compound H and compound R following s.c. dosing are shown in FIG. 2b. Again PEGylation had a profound effect on the PK parameters as evident from the large increase in the AUC of the PEGylated compound compared to unmodified compound R. Following 1 mg/kg s.c. dosing for compound H, an AUC of 48.9 μg×h/mL was observed and >100 ng/mL blood levels were maintained for over 72 h. In contrast, following a 10-fold higher dose for compound R, 10 mg/kg s.c., an AUC of only 6.1 μg×h/mL was observed and >100 ng/mL blood levels were maintained for only 12 h. The bioavailability of compounds H and R were similar, 30% and 20%, respectively.

TABLE 5

| Parameter | compound R | compound H | compound R | compound H |
|---|---|---|---|---|
| Route | i.v. | i.v. | s.c. | s.c. |
| Dose (mg/kg) | 1 | 1 | 10 | 1 |
| $T_{max}$ (h) | 0 | 0 | 0.5 | 24 |
| $C_{max}$ (μg/mL) | 13.1 | 33.8 | 0.78 | 1.1 |
| CL (mL/h/kg) | 426 | 6.2 | 1630 | 20 |
| $V_{ss}$ (mL/kg) | 168 | 81.6 | NA | NA |
| AUC (μg × h/mL) | 2.3 | 161 | 6.1 | 48.9 |
| $T_{1/2}$ (h) | 1.1 | 17.9 | 2.7 | 18.1 |
| F (%) | NA | NA | 20 | 30.4 |

Figure 3:
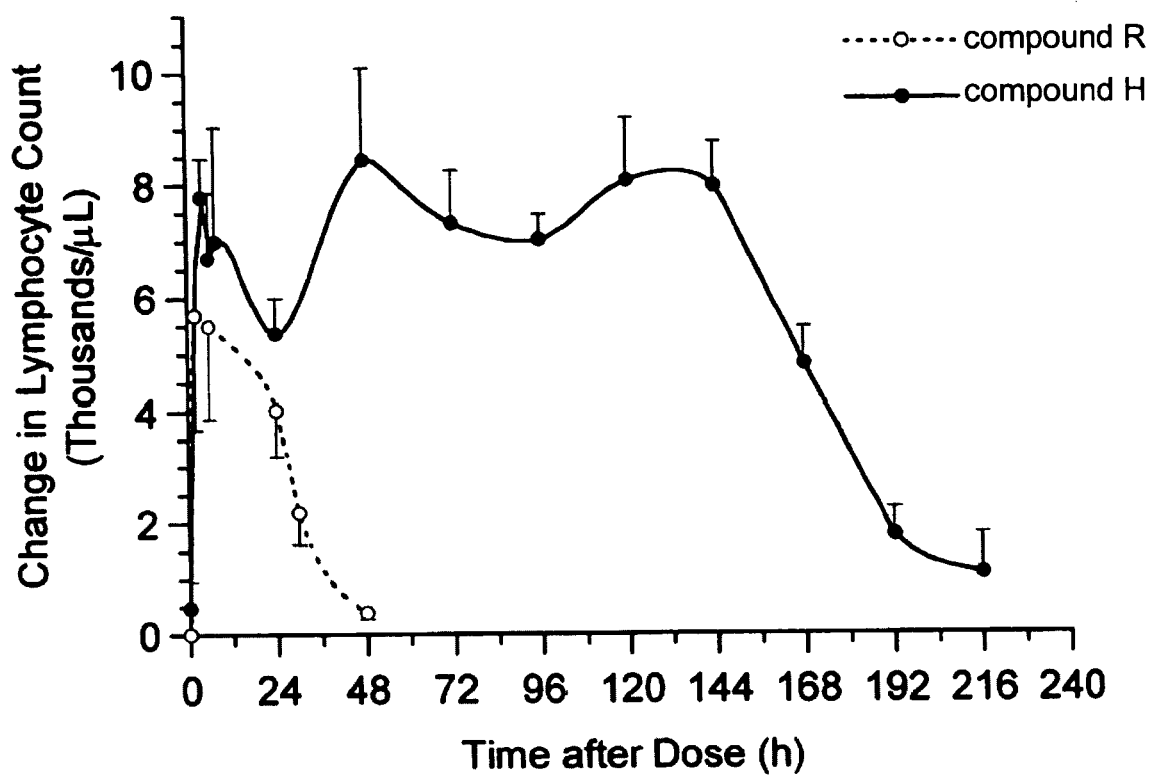
FIG. 3 is a graph depicting change in lymphocyte count in rats after administration of compounds.

Administration of compounds R and H to rats produced an α4β1-integrin dependent lymphocytosis that was sustained as long as sufficient concentrations of the inhibitors were maintained in circulation. From previous studies >90% of α4β1 receptors are estimated to be occupied to maintain lymphocytosis and therefore a target concentration of greater than or equal to 10 ng/mL compound needs to be maintained (see Leone, D. R., et al. (2003) *J. Pharmacol. Exp. Ther.* 305:1150–1162). FIG. 3 shows lymphocytosis induced in vivo by compound H treatment. A 2–3 fold increase in lymphocyte levels was observed. The maximal level of induction was reached at the earliest time point tested, after 4 h. Elevated lymphocyte levels were maintained for 6 days. By day 9 lymphocyte levels had returned to normal. No change in lymphocyte counts was observed following treatment of rats with 2 mg/kg of the PEG control.

Compound R treatment produced a lymphocytosis that lasted one day and lymphocyte levels returned to normal by day 2. The biological effects of compounds R and H were clearly associated with their PK. From these data it appears that a once a week treatment with 1 mg/kg compound H is sufficient to maintain efficacious doses in blood.

Figure 4:
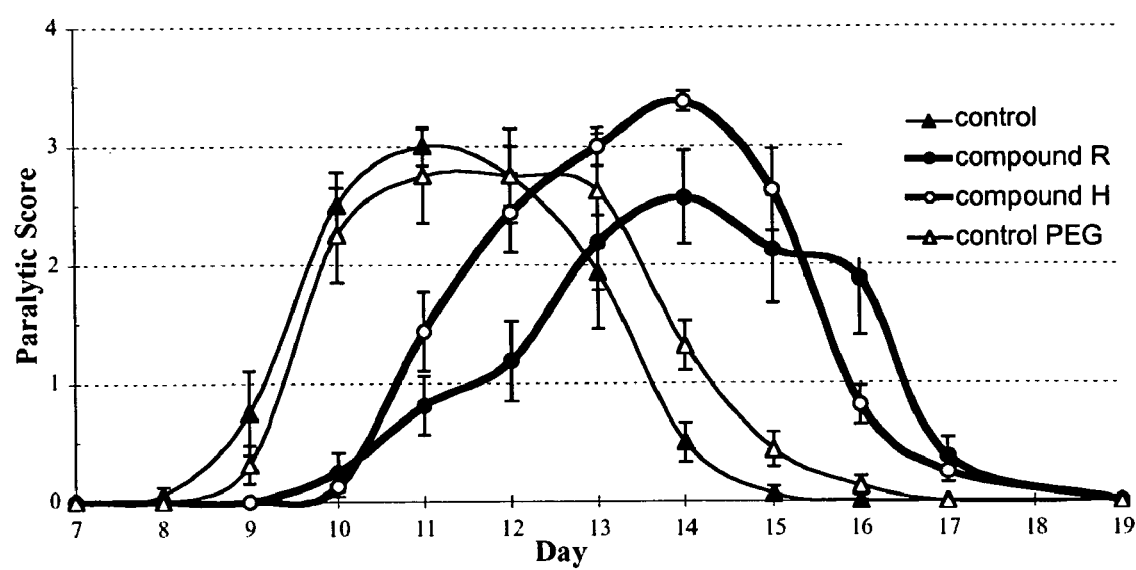
FIG. 4 is a graph depicting the time course of EAE progression in rats.

EAE was induced in female Lewis rats with myelin basic protein peptide. The time course for EAE is shown in FIG. 4. The effects of the myelin basic protein peptide treatment on the paralytic score were monitored from day 7 to day 19. The earliest onset of paralysis in the no treatment control group occurred on day 9 followed by a peak of disease between days 10–12 with a mean paralytic score of 3. The disease resolved to a baseline paralysis score of 0 by day 15. Compound H treatment following injection on day 7 (1 mg/kg, s.c.) resulted in a 2–3 day delay in onset of the disease. No delay in onset of the disease was observed following treatment of rats with 1 mg/kg, s.c. of the PEG control. Daily 30 mg/kg s.c. dosing with compound R produced a similar 2–3 day shift in onset of the disease. The disease in rats from both the compounds H and R treatment groups reached a mean paralytic score of 3.0, indicating that with both inhibitors there was no significant effect on the severity of the disease under the conditions tested.

A number of embodiments have been described. Nevertheless, it will be understood that various modifications may be made. Accordingly, other embodiments are within the scope of the following claims.

What is claimed is:

1. A compound of formula:

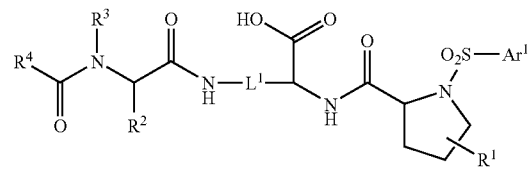

or a stereoisomer thereof wherein $Ar^1$ is a substituted or unsubstituted carbocyclic aryl group, $L^1$ is a $C_1$–$C_4$ alkylene group, $R^1$ is hydrogen or a moiety having the formula —$R^5$-$L^2$-(O-$L^3$-)$_n$OR$^6$, $R^2$ is a $C_1$–$C_{10}$ alkyl, aminoalkyl, thioalkyl, arylalkyl, or hydroxyalkyl group, or a moiety having the formula —$R^5$-$L^2$-(O-$L^3$-)$_n$OR$^6$, $R^3$ is hydrogen or a $C_1$–$C_6$ alkyl group, $R^4$ is an optionally substituted aralkyl group, and at least one of $R^1$ or $R^2$ includes a moiety having the formula —$R^5$-$L^2$-(O-$L^3$-)$_n$OR$^6$, wherein:

each $R^5$, independently, is a bond, —C(O)—, —C(O)—O—, —O—C(O)—, —S(O)$_p$—O—, —O—S(O)$_p$—, —C(O)—N(R$^a$)—, —O—C(O)—N(R$^a$)—, —N(R$^a$)—C(O)—, —N(R$^a$)—C(O)—O—, —O—S(O)$_p$—N(R$^a$)—, —N(R$^a$)—S(O)$_p$—O—, —N(R$^a$)—C(O)—N(R$^b$)—, —N(R$^a$)—S(O)$_p$—N(R$^b$)—, —C(O)—N(R$^a$)—S(O)$_p$—, —S(O)$_p$—N(R$^a$)—C(O)—, —C(O)—N(R$^a$)—S(O)$_p$—N(R$^b$)—, —C(O)—O—S(O)$_p$—N(R$^a$)—, —N(R$^a$)—S(O)$_p$—N(R$^b$)—C(O)—, —N(R$^a$)—S(O)$_p$—O—C(O)—, —S(O)$_p$—N(R$^a$)—, —N(R$^a$)—S(O)$_p$—, —N(R$^a$)—, —S(O)$_p$—, —O—, —S—, or —(C(R$^a$)(R$^b$))$_q$—, wherein each of R$^a$ and R$^b$, independently, is hydrogen, hydroxy, alkyl, alkoxy, amino, aryl, or aralkyl, p is 1 or 2; and q is 1, 2, 3, or 4;

each $L^2$, independently, is a bond, aryl, cycloalkyl, or a $C_{1-C20}$ alkylene group, wherein $L^2$ is optionally interrupted or terminated by one or more of —C(O)—, —C(O)—O—, —O—C(O)—, —S(O)$_p$—O—, —O—S(O)$_p$—, —C(O)—N(R$^a$)—, —C(O)—N (R$^a$)—, —N(R$^a$)—C(O)—, —N(R$^a$)—C(O)—O—, —O—S(O)$_p$—N(R$^a$)—, —N(R$^a$)—S(O)$_p$—O—, —N(R$^a$)—C(O)—N(R$^b$)—, —N(R$^a$)—S(O)$_p$—N (R$^b$)—, —C(O)—N(R$^a$)—S(O)$_p$—, —S(O)$_p$—N (R$^a$)—C(O)—, —C(O)—N(R$^a$)—S(O)$_p$—N(R$^b$)—, —C(O)—O—S(O)$_p$—N(R$^a$)—, —N(R$^a$)—S(O)$_p$—N (R$^b$)—C(O)—, —N(R$^a$)—S(O)$_p$—O—C(O)—, —S(O)$_p$—N(R$^a$)—, —N(R$^a$)—S(O)$_p$—, —N(R$^a$)—, —S(O)$_p$—, —O—, —S—, or —(C(R$^a$)(R$^b$))$_q$—, wherein each of R$^a$ and R$^b$, independently, is hydrogen, hydroxy, alkyl, alkoxy, amino, aryl, or aralkyl, p is 1 or 2; and q is 1, 2, 3, or 4;

each $L^3$, independently, is a $C_1$–$C_6$ alkylene group;

each $R^6$, independently, is hydrogen, a $C_1$–$C_6$ alkyl group, a carbocyclic aryl group, a moiety having the formula:

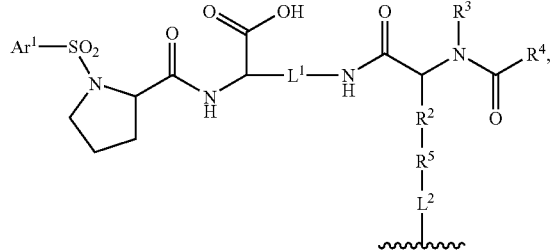

or a moiety having the formula:

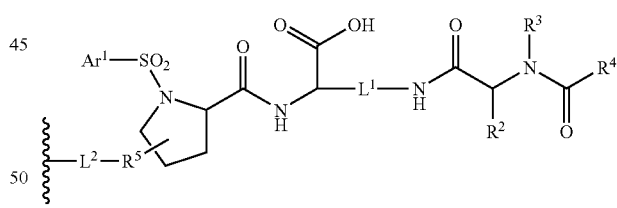

wherein $R^2$ is a $C_1$–$C_{10}$ alkyl, aminoalkyl, thioalkyl, arylalkyl, or hydroxyalkyl group; and n is an integer chosen such that the compound has a molecular weight between 400 and 70,000;

provided that when $Ar^1$ is phenyl, $L^1$ is —CH$_2$CH$_2$—, $R^2$ is 2-methylpropyl, $R^3$ is methyl, and $R^4$ is 4-((N'-2-methylphenyl)ureido)benzyl, $R^1$ is not —N(H)—C(O)—CH$_2$CH$_2$—(OCH$_2$CH$_2$)$_n$—OCH$_3$ where n is selected such that $R^1$ has a molecular weight of approximately 20,000, and $R^1$ is not —N(H)—C(O)—(CH$_2$)$_5$—N(H)—C(O)—CH$_2$CH$_2$—(OCH$_2$CH$_2$)$_n$—OCH$_3$, where n is selected such that $R^1$ has a molecular weight of approximately 20,000, 30,000 or 50,000.

2. The compound of claim 1, wherein $R^4$ is a N-arylurea-substituted aralkyl group.

3. The compound of claim 1, wherein $R^4$ has the formula:

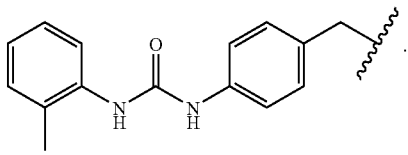

4. The compound of claim 3, wherein $L^1$ is a $C_1$, $C_2$ or $C_3$ alkylene group.

5. The compound of claim 4, wherein $Ar^1$ is phenyl optionally substituted by 1, 2, 3, 4 or 5 halo groups.

6. The compound of claim 1, wherein $R^1$ is a moiety having the formula $-R^5-L^2-(O-L^3-)_nOR^6$.

7. The compound of claim 6, wherein $R^1$ is in an anti configuration.

8. The compound of claim 6, wherein $R^1$ is in an syn configuration.

9. The compound of claim 6, wherein each $L^3$ is $-CH_2-CH_2-$.

10. The compound of claim 6, wherein $R^5$ is $-N(R^a)-C(O)-$.

11. The compound of claim 1, wherein $R^6$ is $C_1-C_6$ alkyl.

12. The compound of claim 1, wherein $R^2$ is 2-methyl-propyl.

13. The compound of claim 12, wherein $L^1$ is $-CH_2-CH_2-$.

14. The compound of claim 12, wherein $R^1$ is a moiety having the formula $-R^5-L^2-(O-L^3-)_nOR^6$.

15. The compound of claim 12, wherein $R^1$ is in an anti configuration.

16. The compound of claim 12, wherein $R^1$ is in a syn configuration.

17. The compound of claim 14, wherein each $L^3$ is $-CH_2-CH_2-$.

18. The compound of claim 17, wherein $R^6$ is $-CH_3$.

19. The compound of claim 1, wherein $R^1$ is hydrogen and $R^2$ is a moiety having the formula $-R^5-L^2-(O-L^3-)_nOR^6$.

20. The compound of claim 19, wherein $-R^5-L^2-$ is $-(CH_2)_4-N(H)-C(O)-(CH_2)_5-N(H)-C(O)-(CH_2)_2-$.

21. The compound of claim 20, wherein each $L^3$ is $-CH_2-CH_2-$.

22. The compound of claim 20, wherein $R^6$ is $-CH_3$.

23. A compound of formula:

or a stereoisomer thereof where $Ar^1$ is a substituted or unsubstituted carbocyclic aryl group, and $R^1$ is a moiety having the formula $-R^5-L^2-(O-L^3-)_nOR^6$; wherein:

$R^5$ is a bond, $-C(O)-$, $-C(O)-O-$, $-O-C(O)-$, $-S(O)_p-O-$, $-O-S(O)_p-$, $-C(O)-O-C(O)-N(R^a)-$, $-N(R^a)-C(O)-$, $-N(R^a)-C(O)-O-$, $-O-S(O)_p-N(R^a)-$, $-N(R^a)-S(O)_p-O-$, $-N(R^a)-C(O)-N(R^b)-$, $-N(R^a)-S(O)_p-N(R^b)-$, $-C(O)-N(R^a)-S(O)_p-$, $-S(O)_p-N(R^a)-C(O)-$, $-C(O)-N(R^a)-S(O)_p-N(R^b)-$, $-C(O)-O-S(O)_p-N(R^a)-$, $-N(R^a)-S(O)_p-N(R^b)-C(O)-$, $-N(R^a)-S(O)_p-O-C(O)-$, $-S(O)_p-N(R^a)-$, $-N(R^a)-S(O)_p-$, $-N(R^a)-$, $-S(O)_p-$, $-O-$, $-S-$, or $-(C(R^a)(R^b))_q-$, wherein each of $R^a$ and $R^b$, independently, is hydrogen, hydroxy, alkyl, alkoxy, amino, aryl, or aralkyl; p is 1 or 2; and q is 1, 2, 3, or 4;

$L^2$ is a bond, aryl, cycloalkyl, or a $C_1-C_{20}$ alkylene group, wherein $L^2$ is optionally interrupted or terminated by one or more of $-C(O)-$, $-C(O)-O-$, $-O-C(O)-$, $-S(O)_p-O-$, $-O-S(O)_p-$, $-C(O)-N(R^a)-$, $-O-C(O)-N(R^a)-$, $-N(R^a)-C(O)-$, $-N(R^a)-C(O)-O-$, $-O-S(O)_p-N(R^a)-$, $-N(R^a)-S(O)_p-O-$, $-N(R^a)-C(O)-N(R^b)-$, $-N(R^a)-S(O)_p-N(R^b)-$, $-C(O)-N(R^a)-S(O)_p-$, $-S(O)_p-N(R^a)-C(O)-$, $-C(O)-N(R^a)-S(O)_p-N(R^a)-$, $-C(O)-O-S(O)_p-N(R^a)-$, $-N(R^a)-S(O)_p-N(R^b)-C(O)-$, $-N(R^a)-S(O)_p-O-C(O)-$, $-S(O)_p-N(R^a)-$, $-N(R^a)-$, $-S(O)_p-$, $-N(R^a)-$, $-S(O)_p-$, $-O-$, $-S-$, or $-(C(R^a)(R^b))_q-$, wherein each of $R^a$ and $R^b$, independently, is hydrogen, hydroxy, alkyl, alkoxy, amino, aryl, or aralkyl, p is 1 or 2; and q is 1, 2, 3, or 4;

each $L^3$, independently, is a $C_1-C_6$ alkylene group;

$R^6$ is hydrogen, a $C_1-C_6$ alkyl group, a carbocyclic aryl group, or a moiety having the formula:

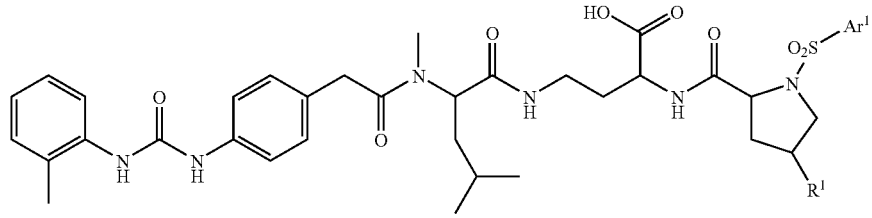

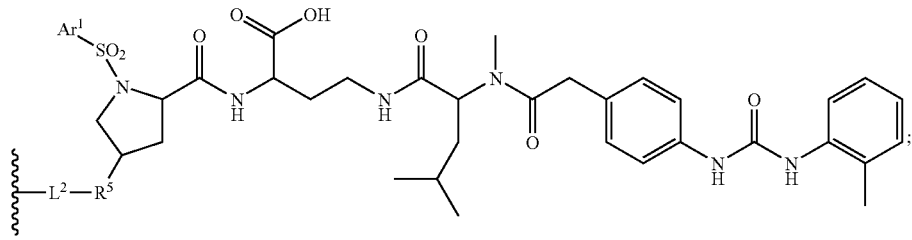

n is an integer chosen such that the compound has a molecular weight between 400 and 70,000;

provided that when $Ar^1$ is phenyl, $R^1$ is not —N(H)—C(O)—$CH_2CH_2$—$(OCH_2CH_2)_n$—$OCH_3$ where n is selected such that $R^1$ has a molecular weight of approximately 20,000, and $R^1$ is not —N(H)—C(O)—$(CH_2)_5$—N(H)—C(O)—$CH_2CH_2$—$(OCH_2CH_2)_n$—$OCH_3$, where n is selected such that $R^1$ has a molecular weight of approximately 20,000, 30,000 or 50,000.

24. The compound of claim 23, wherein $Ar^1$ is phenyl optionally substituted by 1, 2, 3, 4 or 5 halo groups.

25. The compound of claim 23, wherein $R^5$ is —$N(R^a)$—C(O)—.

26. The compound of claim 23, wherein each $L^3$ is —$CH_2$—$CH_2$—.

27. The compound of claim 26, wherein $R^6$ is $C_1$–$C_6$ alkyl.

28. The compound of claim 26, wherein $R^6$ is —$CH_3$.

29. The compound of claim 23, wherein $R^1$ is in an anti configuration.

30. The compound of claim 23, wherein $R^1$ is in a syn configuration.

31. The compound of claim 23, wherein the compound has a molecular weight between 1,000 and 60,000.

32. The compound of claim 23, wherein the compound has a molecular weight between 10,000 and 30,000.

33. A compound of formula:

$L^2$ is a bond, aryl, cycloalkyl, or a $C_1$–$C_{20}$ alkylene group, wherein $L^2$ is optionally interrupted or terminated by one or more of —C(O)—, —C(O)—O—, —O—C(O)—, —S(O)$_p$—O—, —O—S(O)$_p$—, —C(O)—$N(R^a)$—, —O—C(O)—$N(R^a)$—, —$N(R^a)$—C(O)—, —$N(R^a)$—C(O)—O—, —O—S(O)$_p$—$N(R^a)$—, —$N(R^a)$—S(O)$_p$—O—, —$N(R^a)$—C(O)—$N(R^b)$—, —S(O)$_p$—$N(R^a)$—, —$N(R^a)$—S(O)$_p$—, —$N(R^a)$—, —S(O)$_p$—, —O—, —S—, or —$(C(R^a)(R^b))_q$—, wherein each of $R^a$ and $R^b$, independently, is hydrogen, hydroxy, alkyl, alkoxy, amino, aryl, or aralkyl, p is 1 or 2; and q is 1, 2, 3, or 4;

each $L^3$, independently, is a $C_1$–$C_6$ alkylene group;

$R^6$ is hydrogen, a $C_1$–$C_6$ alkyl group, or a carbocyclic aryl group; and n is an integer chosen such that the compound has a molecular weight between 400 and 70,000;

provided that $R^1$ is not —N(H)—C(O)—$CH_2CH_2$—$(OCH_2CH_2)_n$—$OCH_3$ where n is selected such that $R^1$ has a molecular weight of approximately 20,000, and $R^1$ is not —N(H)—C(O)—$(CH_2)_5$—N(H)—C(O)—$CH_2CH_2$—$(OCH_2CH_2)_n$—$OCH_3$, where n is selected such that $R^1$ has a molecular weight of approximately 20,000, 30,000 or 50,000.

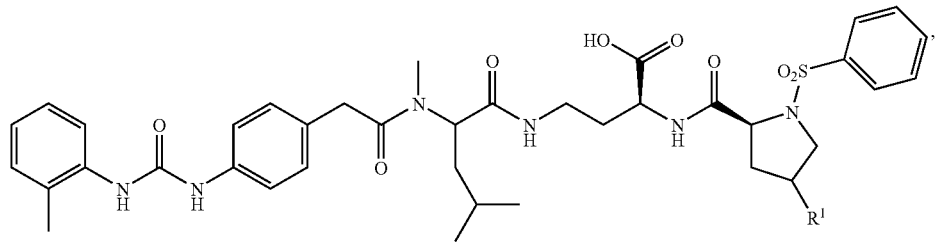

where $R^1$ is a moiety having the formula —$R^5$-$L^2$-(O-$L^3$-)$_n$O$R^6$; wherein:

$R^5$ is a bond, —C(O)—, —C(O)—O—, —O—C(O)—, —S(O)$_p$—O—, —O—S(O)$_p$—, —C(O)—$N(R^a)$—, —O—C(O)—$N(R^a)$—, —$N(R^a)$—C(O)—, —$N(R^a)$—C(O)—O—, —O—S(O)$_p$—$N(R^a)$—, —$N(R^a)$—S(O)$_p$—O—, —$N(R^a)$—C(O)—$N(R^b)$—, —S(O)$_p$—$N(R^a)$—, —$N(R^a)$—S(O)$_p$—, —$N(R^a)$—, —S(O)$_p$—, —O—, —S—, or —$(C(R^a)(R^b))_q$—, wherein each of $R^a$ and $R^b$, independently, is hydrogen, hydroxy, alkyl, alkoxy, amino, aryl, or aralkyl, p is 1 or 2; and q is 1, 2, 3, or 4;

34. A compound of formula:

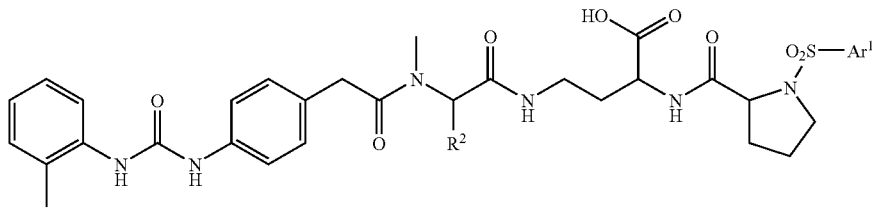

where Ar¹ is a substituted or unsubstituted carbocyclic aryl group, and R² is a moiety having the formula —R⁵-L²-(O-L³-)$_n$OR⁶; wherein:

R⁵ is a bond, —C(O)—, —C(O)—O—, —O—C(O)—, —S(O)$_p$—O—, —O—S(O)$_p$—, —C(O)—N(R$^a$)—, —O—C(O)—N(R$^a$)—, —N(R$^a$)—C(O)—, —N(R$^a$)—C(O)—O—, —O—S(O)$_p$—N(R$^a$)—, —N(R$^a$)—S(O)$_p$—, —N(R$^a$)—C(O)—N(R$^b$)—, —N(R$^a$)—S(O)$_p$—N(R$^b$)—, —C(O)—N(R$^a$) —S(O)$_p$—, —S(O)$_p$—N(R$^a$)—C(O)—, —C(O)—N (R$^a$)—S(O)$_p$—N(R$^b$)—, —C(O)—O—S(O)$_p$—N (R$^a$)—, —N(R$^a$)—S(O)$_p$—N(R$^b$)—C(O)—, —N(R$^a$)—S(O)$_p$—O—C(O)—, —S(O)$_p$—N(R$^a$)— —N(R$^a$) —S(O)$_p$—, —N(R$^a$)—, —S(O)$_p$—, —O—, —S—, or —(C(R$^a$)(R$^b$))$_q$—, wherein each of R$^a$ and R$^b$, independently, is hydrogen, hydroxy, alkyl, alkoxy, amino, aryl, or aralkyl, p is 1 or 2; and q is 1, 2, 3, or 4;

L² is a bond, aryl, cycloalkyl, or a C₁–C₂₀ alkylene group, wherein L is optionally interrupted or terminated by one or more of —C(O)—, —C(O)—O—, —O—C (O)—, —S(O)$_p$—O—, —O—S(O)$_p$—, —C(O)—N (R$^a$)—, —O—C(O)—N(R$^a$)—, —N(R$^a$)—C(O)—, —N(R$^a$)—C(O)—O—, —O—S(O)$_p$—N(R$^a$)—, —N(R$^a$)—S(O)$_p$—O—, —N(R$^a$)—C(O)—N(R$^b$)—, —N(R$^a$)—S(O)$_p$—N(R$^b$)—, —C(O)—N(R$^a$) —S(O)$_p$—, —S(O)$_p$—N(R$^a$)—C(O)—, —C(O)—N (R$^a$)—S(O)$_p$—N(R$^b$)—, —C(O)—O—S(O)$_p$—N (R$^a$)—, —N(R$^a$)—S(O)$_p$—N(R$^b$)—C(O)—, —N(R$^a$)—S(O)$_p$ —O—C(O)—, —S(O)$_p$—N(R$^a$)—, —N(R$^a$) —S(O)$_p$—, —N(R$^a$)—, —S(O)$_p$—, —O—, —S—, or —(C(R$^a$)(R$^b$))$_q$—, wherein each of R$^a$ and R$^b$, independently, is hydrogen, hydroxy, alkyl, alkoxy, amino, aryl, or aralkyl, p is 1 or 2; and q is 1, 2, 3, or 4;

each L³, independently, is a C₁–C₆ alkylene group;

R⁶ is hydrogen, a C₁–C₆ alkyl group, or a carbocyclic aryl group; and n is an integer chosen such that the compound has a molecular weight between 400 and 70,000.

35. The compound of claim 34, wherein Ar¹ is phenyl optionally substituted by 1, 2, 3, 4 or 5 halo groups.

36. The compound of claim 34, wherein R⁵ is —N(R$^a$)—C(O)—.

37. The compound of claim 34, wherein each L³ is —CH₂—CH₂—.

38. The compound of claim 37, wherein R⁶ is C₁–C₆ alkyl.

39. The compound of claim 34, wherein R⁶ is —CH₃.

40. The compound of claim 39, wherein R² has the formula:

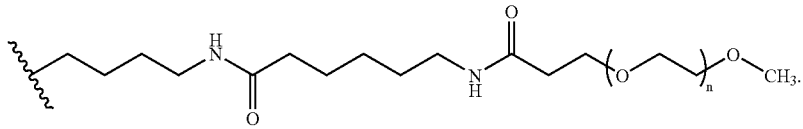

41. The compound of claim 34, wherein the compound has a molecular weight between 1,000 and 60,000.

42. The compound of claim 34, wherein the compound has a molecular weight between 10,000 and 30,000.

43. A compound of formula:

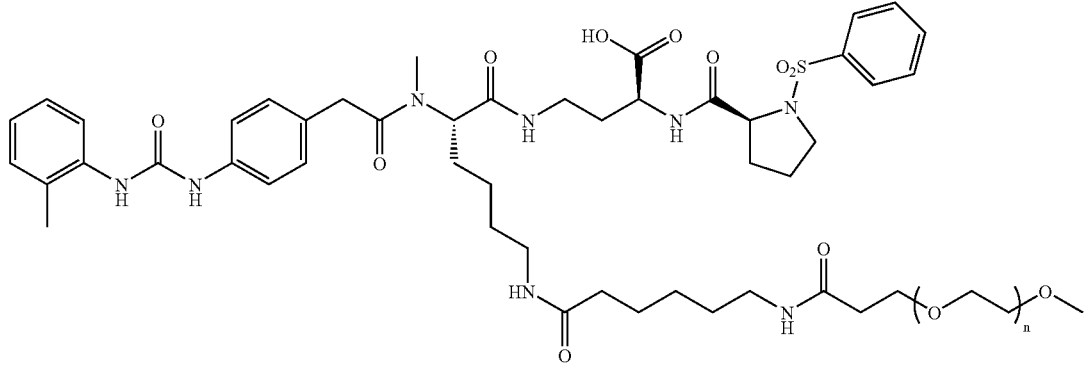

where n is an integer selected so that the compound has a molecular weight between 400 and 70,000.

44. A pharmaceutical composition comprising a pharmaceutical carrier and a compound of formula:

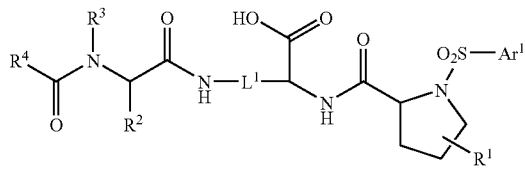

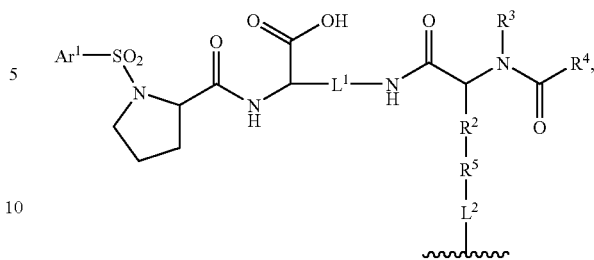

or a moiety having the formula:

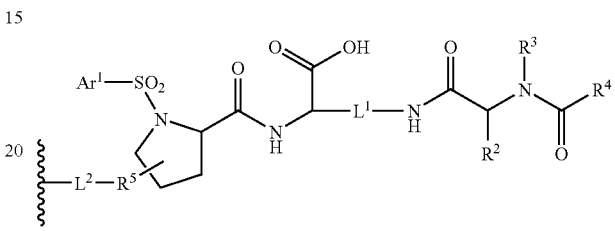

or a stereoisomer thereof wherein $Ar^1$ is a substituted or unsubstituted carbocyclic aryl group, $L^1$ is a $C_1$–$C_4$ alkylene group, $R^1$ is hydrogen or a moiety having the formula —$R^5$-$L^2$-(O-$L^3$-)$_n$O$R^6$, $R^2$ is a $C_1$–$C_{10}$ alkyl, aminoalkyl, thioalkyl, arylalkyl, or hydroxyalkyl group, or a moiety having the formula —$R^5$-$L^2$-(O-$L^3$-)$_n$O$R^6$, $R^3$ is hydrogen or a $C_1$–$C_6$ alkyl group, $R^4$ is an optionally substituted aralkyl group, and at least one of $R^1$ or $R^2$ includes a moiety having the formula —$R^5$-$L^2$-(O-$L^3$-)$_n$O$R^6$, wherein:

each $R^5$, independently, is a bond, —C(O)—, —C(O)—O—, —O—C(O)—, —S(O)$_p$—O—, —O—S(O)$_p$—, —C(O)—N($R^a$)—, —O—C(O)—N($R^a$)—, —N($R^a$)—C(O)—, —N($R^a$)—C(O)—O—, —O—S(O)$_p$—N($R^a$)—, —N($R^a$)—S(O)$_p$—O—, —N($R^a$)—C(O)—N($R^b$)—, —N($R^a$)—S(O)$_p$—N($R^b$)—, —C(O)—N($R^a$)—S(O)$_p$—, —S(O)$_p$—N($R^a$)—C(O)—, —C(O)—N($R^a$)—S(O)$_p$—N($R^b$)—, —C(O)—O—S(O)$_p$—N($R^a$)—, —N($R^a$)—S(O)$_p$—N($R^b$)—C(O)—, —N($R^a$)—S(O)$_p$—O—C(O)—, —S(O)$_p$—N($R^a$)—, —N($R^a$)—S(O)$_p$—, —N($R^a$)—, —S(O)$_p$—, —O—, —S—, or —(C($R^a$)($R^b$))$_q$—, wherein each of $R^a$ and $R^b$, independently, is hydrogen, is hydroxy, alkyl, alkoxy, amino, aryl, or aralkyl, p is 1 or 2; and q is 1, 2, 3, or 4;

each $L^2$, independently, is a bond, aryl, cycloalkyl, or a $C_1$–$C_{20}$ alkylene group, wherein $L^2$ is optionally interrupted or terminated by one or more of —C(O)—, —C(O)—O—, —O—C(O)—, —S(O)$_p$—O—, —O—S(O)$_p$—, —C(O)—N($R^a$)—, —O—C(O)—N($R^a$)—, —N($R^a$)—C(O)—, —N($R^a$)—C(O)—O—, —O—S(O)$_p$—N($R^a$)—, —N($R^a$)—S(O)$_p$—O—, —N($R^a$)—C(O)—N($R^b$)—, —N($R^a$)—S(O)$_p$—N($R^b$)—, —C(O)—N($R^a$)—S(O)$_p$—, —S(O)$_p$—N($R^a$)—C(O)—, —C(O)—N($R^a$)—S(O)$_p$—N($R^b$)—, —C(O)—O—S(O)$_p$—N($R^a$)—, —N($R^a$)—S(O)$_p$—N($R^b$)—C(O)—, —N($R^a$)—S(O)$_p$—O—C(O)—, —S(O)$_p$—N($R^a$)—, —N($R^a$)—S(O)$_p$—, —N($R^a$)—, —S(O)$_p$—, —O—, —S—, or —(C($R^a$)($R^b$))$_q$—, wherein each of $R^a$ and $R^b$, independently, is hydrogen, hydroxy, alkyl, alkoxy, amino, aryl, or aralkyl, p is 1 or 2; and q is 1, 2, 3, or 4;

each $L^3$, independently, is a $C_1$–$C_6$ alkylene group;

each $R^6$, independently, is hydrogen, a $C_1$–$C_6$ alkyl group, a carbocyclic aryl group, a moiety having the formula:

wherein $R^2$ is a $C_1$–$C_{10}$ alkyl, aminoalkyl, thioalkyl, arylalkyl, or hydroxyalkyl group; and n is an integer chosen such that the compound has a molecular weight between 400 and 70,000;

or a pharmaceutically acceptable salt thereof;

provided that when $Ar^1$ is phenyl, $L^1$ is —CH$_2$CH$_2$—, $R^2$ is 2-methylpropyl, $R^3$ is methyl, and $R^4$ is 4-((N'-2-methylphenyl)ureido)benzyl, $R^1$ is not —N(H)—C(O)—CH$_2$CH$_2$—(OCH$_2$CH$_2$)$_n$—OCH$_3$ where n is selected such that $R^1$ has a molecular weight of approximately 20,000, and $R^1$ is not —N(H)—C(O)—(CH$_2$)$_5$—N(H)—C(O)—CH$_2$CH$_2$—(OCH$_2$CH$_2$)$_n$—OCH$_3$, where n is selected such that $R^1$ has a molecular weight of approximately 20,000, 30,000 or 50,000.

45. The composition of claim 44, wherein $R^4$ is a N-arylurea-substituted aralkyl group.

46. The composition of claim 44, wherein $R^4$ has the formula:

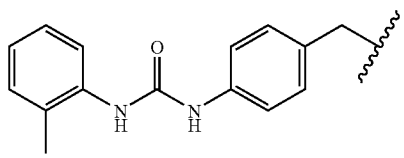

47. The composition of claim 46, wherein $L^1$ is a $C_1$, $C_2$ or $C_3$ alkylene group.

48. The composition of claim 47, wherein $Ar^1$ is phenyl optionally substituted by 1, 2, 3, 4 or 5 halo groups.

49. The composition of claim 44, wherein $R^1$ is a moiety having the formula —$R^5$-$L^2$-(O-$L^3$-)$_n$O$R^6$.

50. The composition of claim 49, wherein $R^1$ is in an anti configuration.

51. The composition of claim 49, wherein $R^1$ is in a syn configuration.

52. The composition of claim 49, wherein each $L^3$ is —CH$_2$—CH$_2$—.

53. The composition of claim 44, wherein $R^5$ is —N($R^a$)—C(O)—.

54. The composition of claim 44, wherein $R^6$ is $C_1$–$C_6$ alkyl.

55. The composition of claim 44, wherein $R^2$ is 2-methylpropyl.

56. The composition of claim 55, wherein $L^1$ is —$CH_2$—$CH_2$—.

57. The composition of claim 55, wherein $R^1$ has the formula —$R^5$-$L^2$-(O-$L^3$-)$_n$OR$^6$.

58. The composition of claim 57, wherein $R^1$ is in an anti configuration.

59. The composition of claim 57, wherein $R^1$ is in a syn configuration.

60. The composition of claim 57, wherein each $L^3$ is —$CH_2$—$CH_2$—.

61. The composition of claim 60, wherein $R^6$ is —$CH_3$.

62. The composition of claim 44, wherein $R^1$ is hydrogen and $R^2$ has the formula —$R^5$-$L^2$-(O-$L^3$-)$_n$OR$^6$.

63. The composition of claim 62, wherein —$R^5$-$L^2$- is —$(CH_2)_4$—N(H)—C(O)—$(CH_2)_5$—N(H)—C(O)—$(CH_2)_2$—.

64. The composition of claim 63, wherein $L_3$ is —$CH_2$—$CH_2$—.

65. The composition of claim 63, wherein $R^6$ is —$CH_3$.

66. A pharmaceutical composition comprising a pharmaceutical carrier and a compound of formula:

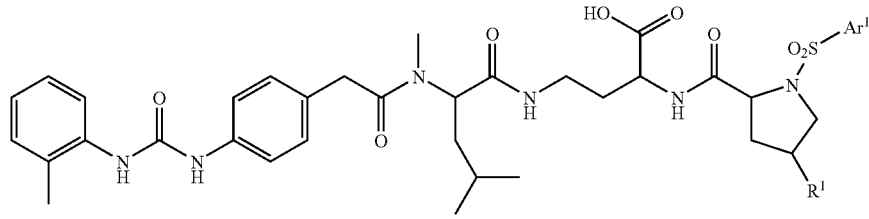

where $Ar^1$ is a substituted or unsubstituted carbocyclic aryl group, and $R^1$ is a moiety having the formula —$R^5$-$L^2$-(O-$L^3$-)$_n$OR$^6$; wherein:

$R^5$ is a bond, —C(O)—, —C(O)—O—, —O—C(O)—, —S(O)$_p$—O—, —O—S(O)$_p$—, —C(O)—N(R$^a$)—, —O—C(O)—N(R$^a$)—, —N(R$^a$)—C(O)—, —N(R$^a$)—C(O)—O—, O—S(O)$_p$—N(R$^a$)—, —N(R$^a$)—S(O)$_p$—O—, —N(R$^a$)—C(O)—N(R$^b$)—, —N(R$^a$)—S(O)$_p$—N(R$^b$)—, —C(O)—N(R$^a$) —S(O)$_p$—, —S(O)$_p$—N(R$^a$)—C(O)—, —C(O)—N (R$^a$)—S(O)$_p$—N(R$^b$)—, —C(O)—O—S(O)$_p$—N (R$^a$)—, —N(R$^a$)—S(O)$_p$—N(R$^b$)—C(O)—, —N(R$^a$)—S(O)$_p$ —O—C(O)—, —S(O)$_p$—N(R$^a$)—, —N(R$^a$)— —S(O)$_p$—, —N(R$^a$)—, —S(O)$_p$—, —O—, —S—, or —(C(R$^a$)(R$^b$))$_q$—, wherein each of R$^a$ and R$^b$, independently, is hydrogen, hydroxy, alkyl, alkoxy, amino, aryl, aralkyl, heterocycloalkyl, heteroaryl, or heteroaralkyl; p is 1 or 2; and q is 1, 2, 3, or 4;

$L^2$ is a bond, aryl, cycloalkyl, or a $C_1$–$C_{20}$ alkylene group, wherein $L^2$ is optionally interrupted or terminated by one or more of —C(O)—, —C(O)—O—, —O—C(O)—, —S(O)$_p$—O—, —O—S(O)$_p$—, —C(O)—N(R$^a$)—, O—C(O)—N(R$^a$)—, —N(R$^a$)—C(O)—, —N(R$^a$)—C(O)—O—, —O—S(O)$_p$—N(R$^a$)—, —N(R$^a$)—S(O)$_p$—O—, —N(R$^a$)—C(O)—N(R$^b$)—, —N(R$^a$)—S(O)$_p$—N(R$^a$)—, —C(O)—N(R$^a$) —S(O)$_p$—, —S(O)$_p$—N(R$^a$)—C(O)—, —C(O)—N (R$^a$)—S(O)$_p$—N(R$^b$)—, —C(O)—O—S(O)$_p$—N (R$^a$)—, —N(R$^a$)—S(O)$_p$—N(R$^b$)—C(O)—, —N(R$^a$)—S(O)$_p$ —O—C(O)—, —S(O)$_p$—N(R$^a$)—, —N(R$^a$)— —S(O)$_p$—, —N(R$^a$)—, —S(O)$_p$—, —O—, —S—, or —(C(R$^a$)(R$^b$))$_q$—, wherein each of R$^1$ and R$^b$, independently, is hydrogen, hydroxy, alkyl, alkoxy, amino, aryl, or aralkyl, p is 1 or 2; and q is 1, 2, 3, or 4;

each $L^3$, independently, is a $C_1$–$C_6$ alkylene group;

$R^6$ is hydrogen, a $C_1$–$C_6$ alkyl group, a carbocyclic aryl group, or a moiety having the formula:

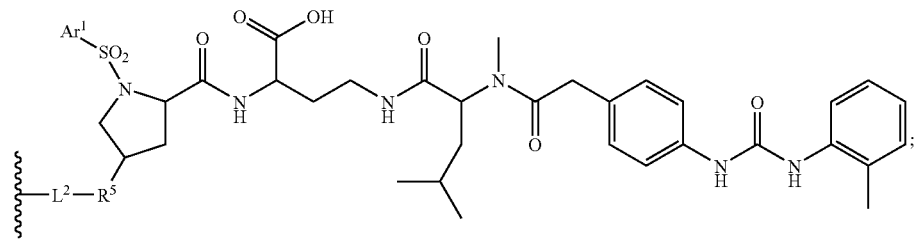

n is an integer chosen such that the compound has a molecular weight between 400 and 70,000;

or a pharmaceutically acceptable salt thereof;

provided that when $Ar^1$ is phenyl, $R^1$ is not —N(H)—C(O)—$CH_2CH_2$—(OCH$_2$CH$_2$)$_n$—OCH$_3$ where n is selected such that $R^1$ has a molecular weight of approximately 20,000, and $R^1$ is not —N(H)—C(O)—(CH$_2$)$_5$—N(H)—C(O)—CH$_2$CH$_2$—(OCH$_2$CH$_2$)$_n$—OCH$_3$, where n is selected such that $R^1$ has a molecular weight of approximately 20,000, 30,000 or 50,000.

67. The composition of claim 66, wherein $Ar^1$ is phenyl optionally substituted by 1, 2, 3, 4 or 5 halo groups.

68. The composition of claim 66, wherein $R^5$ is —N($R^a$)—C(O)—.

69. The composition of claim 66, wherein each $L^3$ is —CH$_2$—CH$_2$—.

70. The composition of claim 69, wherein $R^6$ is $C_1$–$C_6$ alkyl.

71. The composition of claim 69, wherein $R^6$ is —CH$_3$.

72. The composition of claim 66, wherein $R^1$ is in an anti configuration.

73. The composition of claim 66, wherein $R^1$ is in a syn configuration.

74. The composition of claim 66, wherein the compound has a molecular weight between 1,000 and 60,000.

75. The composition of claim 66, wherein the compound has a molecular weight between 10,000 and 30,000.

76. A pharmaceutical composition comprising a pharmaceutical carrier and a compound of formula:

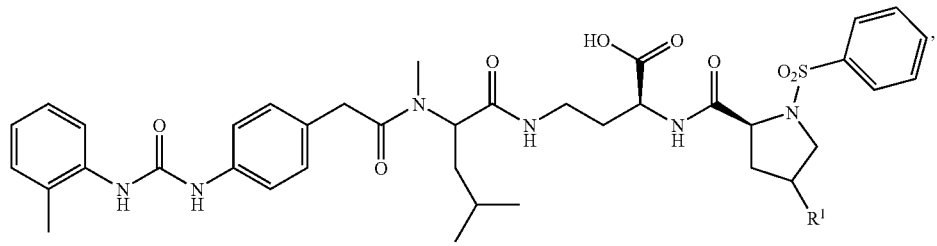

where $R^1$ is a moiety having the formula —$R^5$-$L^2$-(O-$L^3$-)$_n$ OR$^6$; wherein:

$R^5$ is a bond, —C(O)—, —C(O)—O—, —O—C(O)—, —S(O)$_p$—O—, —O—S(O)$_p$—, —C(O)—N($R^a$)—, —O—C(O)—N($R^a$)—, —N($R^a$)—C(O)—, —N($R^a$)—C(O)—O—, —O—S(O)$_p$—N($R^a$)—, —N($R^a$)—S(O)$_p$—O—, —N($R^a$)—C(O)—N($R^b$)—, —S(O)$_p$—N($R^a$)—, —N($R^a$)—S(O)$_p$—, —N($R^a$)—, —S(O)$_p$—, —O—, —S—, or —(C($R^a$)($R^b$))$_q$—, wherein each of $R^a$ and $R^b$, independently, is hydrogen, hydroxy, alkyl, alkoxy, amino, aryl, or aralkyl, p is 1 or 2; and q is 1, 2, 3, or 4;

$L^2$ is a bond, aryl, heteroaryl, cycloalkyl, heterocyclyl, or a $C_1$–$C_{20}$ alkylene group, wherein $L^2$ is optionally interrupted or terminated by one or more of —C(O)—, —C(O)—O—, —O—C(O)—, —S(O)$_p$—O—, —O—S(O)$_p$—, —C(O)—N($R^a$)—, —O—C(O)—N($R^a$)—, —N($R^a$)—C(O)—, —N($R^a$)—C(O)—O—, —S(O)$_p$—N($R^a$)—, —N($R^a$)—S(O)$_p$—O—, —N($R^a$)—C(O)—N($R^b$)—, —S(O)$_p$—N($R^a$)—, —N($R^a$)—S(O)$_p$—, —N($R^a$)—, —S(O)$_p$—, —O—, —S—, or —(C($R^a$)($R^b$))$_q$—, wherein each of $R^a$ and $R^b$, independently, is hydrogen, hydroxy, alkyl, alkoxy, amino, aryl, or aralkyl, p is 1 or 2; and q is 1, 2, 3, or 4;

each $L^3$, independently, is a $C_1$–$C_6$ alkylene group;

$R^6$ is hydrogen, a $C_1$–$C_6$ alkyl group, or substituted or unsubstituted a carbocyclic aryl group; and n is an integer chosen such that the compound has a molecular weight between 400 and 70,000;

or a pharmaceutically acceptable salt thereof;

provided that $R^1$ is not —N(H)—C(O)—CH$_2$CH$_2$—(OCH$_2$CH$_2$)$_n$—OCH$_3$ where n is selected such that $R^1$ has a molecular weight of approximately 20,000, and $R^1$ is not —N(H)—C(O)—(CH$_2$)$_5$—N(H)—C(O)—CH$_2$CH$_2$—(OCH$_2$CH$_2$)$_n$—OCH$_3$, where n is selected such that $R^1$ has a molecular weight of approximately 20,000, 30,000 or 50,000.

77. A pharmaceutical composition comprising a pharmaceutical carrier and a compound of formula:

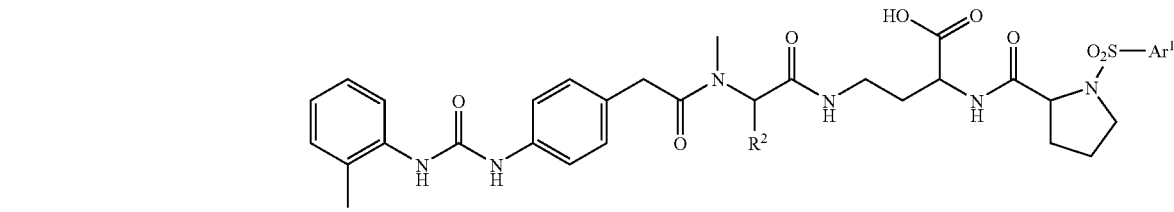

where $Ar^1$ is a substituted or unsubstituted carbocyclic aryl group, and $R^2$ is a moiety having the formula —$R^5$-$L^2$-(O-$L^3$-)$_n$OR$^6$; wherein:

$R^5$ is a bond, —C(O)—, —C(O)—O—, —O—C(O)—, —S(O)$_p$—O—, —O—S(O)$_p$—, —C(O)—N($R^a$)—, —O—C(O)—N($R^a$)—, —N($R^a$)—C(O)—, —N($R^a$)—C(O)—O—, —S(O)$_p$—N($R^a$)—, —N($R^a$)—S(O)$_p$—O—, —N($R^a$)—C(O)—N($R^b$)—, —N($R^a$)—S(O)$_p$—N($R^b$)—, —C(O)—N($R^a$)—S(O)$_p$—, —S(O)$_p$—N($R^a$)—C(O)—, —C(O)—N($R^a$)—S(O)—N($R^b$)—, —C(O)—O—S(O)$_p$—N($R^a$)—, —N($R^a$)—S(O)$_p$—N($R^b$)—C(O)—, —N($R^a$)—S(O)$_p$—O—C(O)—, —S(O)$_p$—N($R^a$)—, —N($R^a$)—S(O)$_p$—, —N($R^a$)—, —S(O)$_p$—, —O—, —S—, or —(C(R$^a$)(R$^b$))$_q$—, wherein each of R$^a$ and R$^b$, independently, is hydrogen, hydroxy, alkyl, alkoxy, amino, aryl, or aralkyl, p is 1 or 2; and q is 1, 2, 3, or 4;

L$^2$ is a bond, aryl, cycloalkyl, or a C$_1$–C$_{20}$ alkylene group, wherein L$^2$ is optionally interrupted or terminated by one or more of —C(O)—, —C(O)—O—, —O—C(O)—, —S(O)$_p$—O—, —O—S(O)$_p$—, —C(O)—N(R$^a$)—, —O—C(O)—N(R$^a$)—, —N(R$^a$)—C(O)—, —N(R$^a$)—C(O)—O—, —O—S(O)$_p$—N(R$^a$)—, —N(R$^a$)—S(O)$_p$—O—, —N(R$^a$)—C(O)—N(R$^b$)—, —N(R$^a$)—S(O)$_p$—N(R$^b$)—, —C(O)—N(R$^a$)—S(O)$_p$—, —S(O)$_p$—N(R$^a$)—C(O)—, —C(O)—N(R$^a$)—S(O)$_p$—N(R$^b$)—, —C(O)—O—S(O)$_p$—N(R$^a$)—, —N(R$^a$)—S(O)$_p$—N(R$^b$)—C(O)—, —N(R$^a$)—S(O)$_p$—O—C(O)—, —S(O)$_p$—N(R$^a$)—N(R$^a$)—S(O)$_p$—, —N(R$^a$)—, —S(O)$_p$—, —O—, —S—, or —(C(R$^a$)(R$^b$))$_q$—, wherein each of R$^a$ and R$^b$, independently, is hydrogen, hydroxy, alkyl, alkoxy, amino, aryl, or aralkyl, heterocycloalkyl, heteroaryl, or heteroaralkyl; p is 1 or 2; and q is 1, 2, 3, or 4;

each L$^3$, independently, is a C$_1$–C$_6$ alkylene group;

R$^6$ is hydrogen, a C$_1$–C$_6$ alkyl group, or an aryl group; and n is an integer chosen such that the compound has a molecular weight between 400 and 70,000;

or a pharmaceutically acceptable salt thereof.

78. The composition of claim 77, wherein Ar$^1$ is phenyl optionally substituted by 1, 2, 3, 4 or 5 halo groups.

79. The composition of claim 77, wherein R$^5$ is —N(R$^a$)—C(O)—.

80. The composition of claim 77, wherein each L$^3$ is —CH$_2$—CH$_2$—.

81. The composition of claim 80, wherein R$^6$ is C$_1$–C$_6$ alkyl.

82. The composition of claim 80, wherein R$^6$ is —CH$_3$.

83. The composition of claim 82, wherein R$^2$ has the formula:

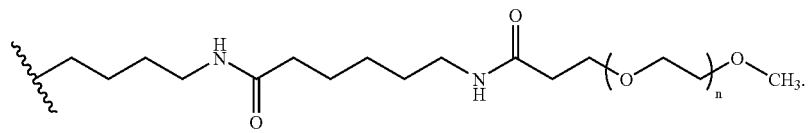

84. The composition of claim 77, wherein the compound has a molecular weight between 1,000 and 60,000.

85. The composition of claim 77, wherein the compound has a molecular weight between 10,000 and 30,000.

86. A compound of formula:

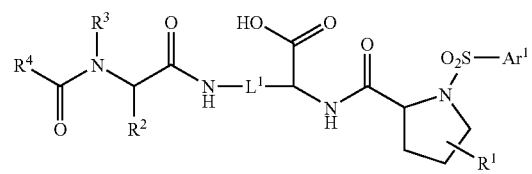

wherein Ar$^1$ is a substituted or unsubstituted carbocyclic aryl group, L$^1$ is a C$_1$–C$_4$ alkylene group, R$^1$ is hydrogen or a moiety having the formula —R$^5$-L$^2$-(O-L$^3$-)$_n$OR$^6$, R$^2$ is a C$_1$–C$_{10}$ alkyl, aminoalkyl, thioalkyl, arylalkyl, or hydroxyalkyl group, or a moiety having the formula —R$^5$-L$^2$-(O-L$^3$-)$_n$OR$^6$, R$^3$ is hydrogen or a C$_1$–C$_6$ alkyl group, R$^4$ is an optionally substituted aralkyl group, and at least one of R$^1$ or R$^2$ includes a moiety having the formula —R$^5$-L$^2$-(O-L$^3$-)$_n$OR$^6$, wherein:

each R$^5$, independently, is a bond, —C(O)—, —C(O)—O—, —O—C(O)—, —S(O)$_p$—O—, —O—S(O)$_p$—, —C(O)—N(R$^a$)—, —O—C(O)—N(R$^a$)—, —N(R$^a$)—C(O)—, —N(R$^a$)—C(O)—O—, —S(O)$_p$—N(R$^a$)—, —N(R$^a$)—S(O)$_p$—O—, —N(R$^a$)—C(O)—N(R$^b$)—, —N(R$^a$)—S(O)$_p$—N(R$^b$)—, —C(O)—N(R$^a$)—S(O)$_p$—, —S(O)$_p$—N(R$^a$)—C(O)—, —C(O)—N(R$^a$)—S(O)$_p$—N(R$^b$)—, —C(O)—O—S(O)$_p$—N(R$^a$)—, —N(R$^a$)—S(O)$_p$—N(R$^b$)—C(O)—, —N(R$^a$)—S(O)$_p$—O—C(O)—, —S(O)$_p$—N(R$^a$)—, —N(R$^a$)—S(O)$_p$—, —N(R$^a$)—, —S(O)$_p$—, —O—, —S—, or —(C(R$^a$)(R$^b$))$_q$—, wherein each of R$^a$ and R$^b$, independently, is hydrogen, hydroxy, alkyl, alkoxy, amino, aryl, or aralkyl; p is 1 or 2; and q is 1, 2, 3, or 4;

each L$^2$, independently, is a bond, aryl, cycloalkyl, or a C$_1$–C$_{20}$ alkylene group, wherein L$^2$ is optionally interrupted or terminated by one or more of —C(O)—, —C(O)—O—, —O—C(O)—, —S(O)$_p$—O—, —O—S(O)$_p$—, —C(O)—N(R$^a$)—, —O—C(O)—N(R$^a$)—, —N(R$^a$)—C(O)—, —N(R$^a$)—C(O)—O—, —O—S(O)$_p$—N(R$^a$)—, —N(R$^a$)—S(O)$_p$—O—, —N(R$^a$)—C(O)—N(R$^b$)—, —N(R$^a$)—S(O)$_p$—N(R$^b$)—, —C(O)—N(R$^a$)—S(O)$_p$—, —S(O)$_p$—N(R$^a$)—C(O)—, —C(O)—N(R$^a$)—S(O)$_p$—N(R$^b$)—, —C(O)—O—S(O)$_p$—N(R$^a$)—, —N(R$^a$)—S(O)$_p$—N(R$^b$)—C(O)—, —N(R$^a$)—S(O)$_p$—O—C(O)—, —S(O)$_p$—N(R$^a$)—, —N(R$^a$)—S(O)$_p$—, —N(R$^a$)—, —S(O)$_p$—, —O—, —S—, or —(C(R$^a$)(R$^b$))$_q$—, wherein each of R$^a$ and R$^b$, independently, is hydrogen, hydroxy, alkyl, alkoxy, amino, aryl, or aralkyl; p is 1 or 2; and q is 1, 2, 3, or 4; and provided that when R$^5$ is —N(R$^a$)—C(O)—, L$^2$ is not a C$_1$–C$_{20}$ alkylene group;

each L$^3$, independently, is a C$_1$–C$_6$ alkylene group;

each R$^6$, independently, is hydrogen, a C$_1$–C$_6$ alkyl group, a carbocyclic aryl group, a moiety having the formula:

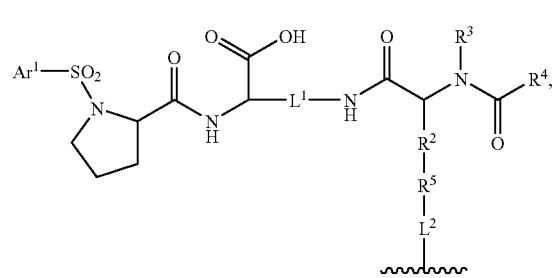

or a moiety having the formula:

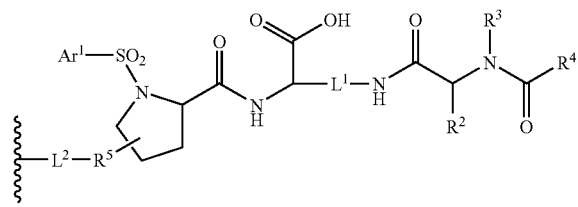

wherein $R^2$ is a $C_1$–$C_{10}$ alkyl, aminoalkyl, thioalkyl, aralkyl, or hydroxyalkyl group; and n is an integer chosen such that the compound has a molecular weight between 400 and 70,000.

87. A pharmaceutical composition comprising a pharmaceutical carrier and a compound of formula:

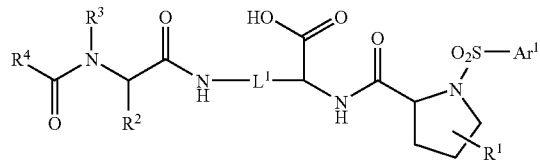

wherein $Ar^1$ is a carbocyclic aryl group, $L^1$ is a $C_1$–$C_4$ alkylene group, $R^1$ is hydrogen or a moiety having the formula —$R^5$-$L^2$-(O-$L^3$-)$_n$O$R^6$, $R^2$ is a $C_1$–$C_{10}$ alkyl, aminoalkyl, thioalkyl, arylalkyl, or hydroxyalkyl group, or a moiety having the formula —$R^5$-$L^2$-(O-$L^3$-)$_n$O$R^6$, $R^3$ is hydrogen or a $C_1$–$C_6$ alkyl group, $R^4$ is an optionally substituted aralkyl group, and at least one of $R^1$ or $R^2$ includes a moiety having the formula —$R^5$-$L^2$-(O-$L^3$-)$_n$O$R^6$, wherein:

each $R^5$, independently, is a bond, —C(O)—, —C(O)—O—, —O—C(O)—, —S(O)$_p$—O—, —O—S(O)$_p$—, —C(O)—N($R^a$)—, —O—C(O)—N($R^a$)—, —N($R^a$)—C(O)—, —N($R^a$)—C(O)—O—, —S(O)$_p$—N($R^a$)—, —N($R^a$)—S(O)$_p$—O—, —N($R^a$)—C(O)—N($R^b$)—, —N($R^a$)—S(O)$_p$—N($R^b$)—, —C(O)—N($R^a$)—S(O)$_p$—, —S(O)$_p$—N($R^a$)—C(O)—, —C(O)—N($R^a$)—S(O)$_p$—N($R^b$)—, —C(O)—O—S(O)$_p$—N($R^a$)—, —N($R^a$)—S(O)$_p$—N($R^b$)—C(O)—, —N($R^a$)—S(O)$_p$—O—C(O)—, —S(O)$_p$—N($R^a$)—, —N($R^a$)—S(O)$_p$—, —N($R^a$)—, —S(O)$_p$—, —O—, —S—, or —(C($R^a$)($R^b$))$_q$—, wherein each of $R^a$ and $R^b$, independently, is hydrogen, hydroxy, alkyl, alkoxy, amino, aryl, or aralkyl; p is 1 or 2; and q is 1, 2, 3, or 4;

each $L^2$, independently, is a bond, aryl, cycloalkyl, or a $C_1$–$C_{20}$ alkylene group, wherein $L^2$ is optionally interrupted or terminated by one or more of —C(O)—, —C(O)—O—, —O—C(O)—, —S(O)$_p$—O—, —O—S(O)$_p$—, —C(O)—N($R^a$)—, —O—C(O)—N($R^a$)—, —N($R^a$)—C(O)—, —N($R^a$)—C(O)—O—, —O—S(O)$_p$—N($R^a$)—, —N($R^a$)—S(O)$_p$—O—, —N($R^a$)—C(O)—N($R^b$)—, —N($R^a$)—S(O)$_p$—N($R^b$)—, —C(O)—N($R^a$)—S(O)$_p$—, —S(O)$_p$—N($R^a$)—C(O)—, —C(O)—N($R^a$)—S(O)$_p$—N($R^b$)—, —C(O)—O—S(O)$_p$—N($R^a$)—, —N($R^a$)—S(O)$_p$—N($R^b$)—C(O)—, —N($R^a$)—S(O)$_p$—O—C(O)—, —S(O)$_p$—N($R^a$)—, —N($R^a$)—S(O)$_p$—, —N($R^a$)—, —S(O)$_p$—, —O—, —S—, or —(C($R^a$)($R^b$))$_q$—, wherein each of $R^a$ and $R^b$, independently, is hydrogen, hydroxy, alkyl, alkoxy, amino, aryl, aralkyl; p is 1 or 2; and q is 1, 2, 3, or 4;

each $L^3$, independently, is a $C_1$–$C_6$ alkylene group;

each $R^6$, independently, is hydrogen, a $C_1$–$C_6$ alkyl group, a carbocyclic aryl group, a moiety having the formula:

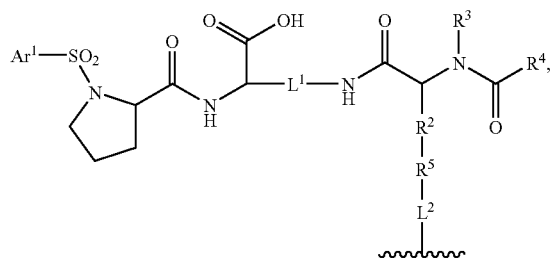

or a moiety having the formula:

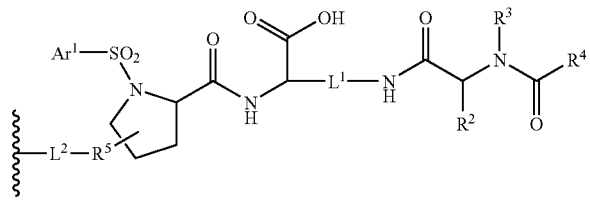

wherein $R^2$ is a $C_1$–$C_{10}$ alkyl, aminoalkyl, thioalkyl, aralkyl, or hydroxyalkyl group; and n is an integer chosen such that the compound has a molecular weight between 400 and 70,000;

or a pharmaceutically acceptable salt thereof.

* * * * *